(12) United States Patent
Sallin et al.

(10) Patent No.: US 10,221,439 B2
(45) Date of Patent: Mar. 5, 2019

(54) SENSORS, METHODS AND KITS FOR DETECTING NICOTINAMIDE ADENINE DINUCLEOTIDES

(71) Applicant: Max-Planck-Gesellschaft zur Förderung der Wissenschaften e.V., München (DE)

(72) Inventors: Olivier Sallin, Lussy (CH); Luc Reymond, Morges (CH); Kai Peter Johnsson, Neuchatel (CH)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 0 days.

(21) Appl. No.: 15/550,239

(22) PCT Filed: Feb. 16, 2016

(86) PCT No.: PCT/EP2016/053280
§ 371 (c)(1),
(2) Date: Aug. 10, 2017

(87) PCT Pub. No.: WO2016/131833
PCT Pub. Date: Aug. 25, 2016

(65) Prior Publication Data
US 2018/0087083 A1    Mar. 29, 2018

(30) Foreign Application Priority Data

Feb. 16, 2015 (EP) ..................... 15155272

(51) Int. Cl.
*C12Q 1/00* (2006.01)
*C12Q 1/26* (2006.01)
*G01N 33/573* (2006.01)
*G01N 33/542* (2006.01)

(52) U.S. Cl.
CPC ............. *C12Q 1/008* (2013.01); *C12Q 1/26* (2013.01); *C12Y 101/01153* (2013.01); *G01N 33/542* (2013.01); *G01N 33/5735* (2013.01); *G01N 2333/902* (2013.01)

(58) Field of Classification Search
CPC .. C12Q 1/008; C12Q 1/26; C12Y 101/01153; G01N 33/542; G01N 33/5735; G01N 2333/902
See application file for complete search history.

(56) References Cited

FOREIGN PATENT DOCUMENTS

WO    2015007317 A1    1/2015

OTHER PUBLICATIONS

Broun et al., Catalytic plasticity of fatty acid modification enzymes underlying chemical diversity of plant lipids. Science, 1998, vol. 282: 1315-1317. (Year: 1998).*

Chica et al., Semi-rational approaches to engineering enzyme activity: combining the benefits of directedevolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol.,2007, vol. 143: 212-223. (Year: 2007).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Zhao et al. Genetically Encoded Fluorescent Sensors for Intracellular NADH Detection. Cell Metabolism 14, 555-556, Oct. 2011.
Brun et al. Semisynthesis of Fluorescent Metabolite Sensors on Cell Surfaces. J. Am. Chem. Soc. 2011, 133, 16235-16242.
Brun et al. Semisynthetic Fluorescent Sensor Proteins Based on Self-Labeling Protein Tags. J. Am. Chem. Soc. 2009, 131, 5873-5884.
Masharina et al. A Fluorescent Sensor for GABA and Synthetic GABA B Receptor Ligands. J. Am. Chem. Soc. 2012, 134, 19026-19034.
Griss et al. Bioluminescent Sensor Proteins for Point-of-Care Therapeutic Drug Monitoring. Nature Chemical Biology. vol. 10, Jul. 2014, pp. 598-604.
Haruki et al. Tetrahydrobiopterin Biosynthesis as an Off-Target of Sulfa Drugs. Science, vol. 340, May 24, 2013, pp. 987-991.
Haruki et al. Exploiting Ligand-Protein Conjugates to Monitor Ligand-Receptor Interactions. PLoS One, May 2012, vol. 7, Issue 5, e37598.

(Continued)

*Primary Examiner* — Ganapathirama Raghu
(74) *Attorney, Agent, or Firm* — Arent Fox LLP

(57) ABSTRACT

The invention relates to the in vitro and in cellulo detection of the cofactors nicotinamide adenine dinucleotide (NAD) and nicotinamide adenine dinucleotide phosphate (NADP). Provided is a sensor molecule for fluorescence- or luminescence-based detection of a nicotinamide adenine dinucleotide analyte, in particular for detecting the concentrations of $NAD^+$, $NADP^+$ and/or the ratios of the concentrations of $NAD^+/NADH$ and $NADP^+/NADPH$, the sensor comprising (i) a binding protein (BP) for the nicotinamide adenine dinucleotide analyte, the BP being derived from sepiapterin reductase (SPR; EC 1.1.1.153) (ii) an SPR ligand (SPR-L) capable of intramolecular binding to said BP in the presence of the oxidized form of said analyte; and (iii) at least one fluorophore.

Figure 1A:
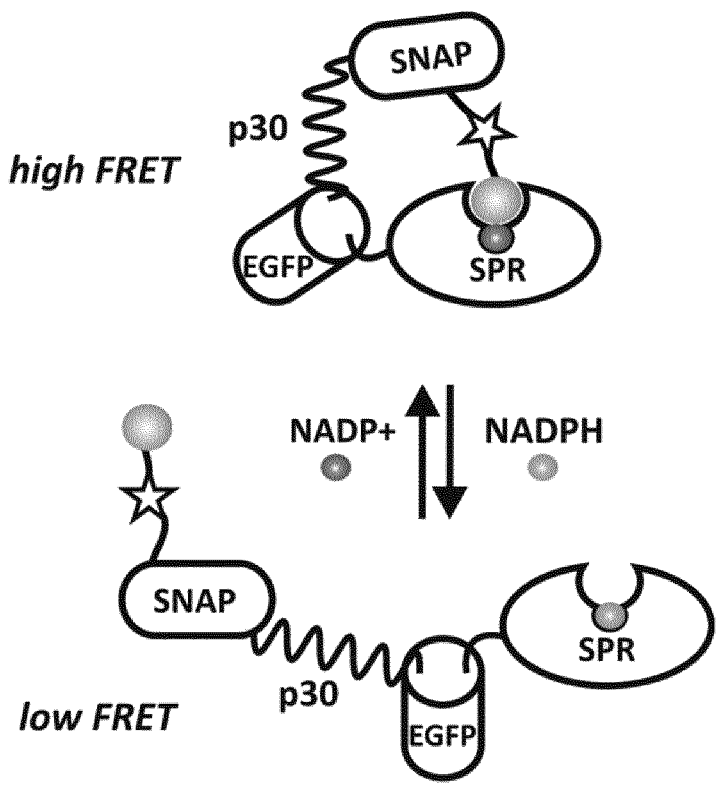

22 Claims, 24 Drawing Sheets
Specification includes a Sequence Listing.

(56) References Cited

OTHER PUBLICATIONS

Yang et al. Sulfa Drugs Inhibit Sepiapterin Reduction and Chemical Redox Cycling by Sepiapterin Reductase. J. Pharmacol. Exp. Ther. 352:529-540, Mar. 2015.

Yang et al. Sepiapterin Reductase Mediates Chemical Redox Cycling in Lung Epithelial Cells. J. Biol. Chem. Jun. 2013, vol. 288, No. 26, pp. 19221-19237.

Stein et al. Synthetic Protein Switches: Design, Principles and Applications. Trends in Biotechnology, Feb. 2015, vol. 33, No. 2, pp. 101-110.

* cited by examiner

SEQUENCE LISTING

<160> NUMBER OF SEQ ID NOS: 7

<210> SEQ ID NO 1
<211> LENGTH: 261
<212> TYPE: PRT
<213> ORGANISM: Homo sapiens

<400> SEQUENCE: 1

```
Met Glu Gly Gly Leu Gly Arg Ala Val Cys Leu Leu Thr Gly Ala Ser
1               5                   10                  15

Arg Gly Phe Gly Arg Thr Leu Ala Pro Leu Leu Ala Ser Leu Leu Ser
            20                  25                  30

Pro Gly Ser Val Leu Val Leu Ser Ala Arg Asn Asp Glu Ala Leu Arg
        35                  40                  45

Gln Leu Glu Ala Glu Leu Gly Ala Glu Arg Ser Gly Leu Arg Val Val
    50                  55                  60

Arg Val Pro Ala Asp Leu Gly Ala Glu Ala Gly Leu Gln Gln Leu Leu
65                  70                  75                  80

Gly Ala Leu Arg Glu Leu Pro Arg Pro Lys Gly Leu Gln Arg Leu Leu
                85                  90                  95
```

Leu Ile Asn Asn Ala Gly Ser Leu Gly Asp Val Ser Lys Gly Phe Val
            100                 105                 110

Asp Leu Ser Asp Ser Thr Gln Val Asn Asn Tyr Trp Ala Leu Asn Leu
            115                 120                 125

Thr Ser Met Leu Cys Leu Thr Ser Ser Val Leu Lys Ala Phe Pro Asp
            130                 135                 140

Ser Pro Gly Leu Asn Arg Thr Val Val Asn Ile Ser Ser Leu Cys Ala
145                 150                 155                 160

Leu Gln Pro Phe Lys Gly Trp Ala Leu Tyr Cys Ala Gly Lys Ala Ala
            165                 170                 175

Arg Asp Met Leu Phe Gln Val Leu Ala Leu Glu Glu Pro Asn Val Arg
            180                 185                 190

Val Leu Asn Tyr Ala Pro Gly Pro Leu Asp Thr Asp Met Gln Gln Leu
            195                 200                 205

Ala Arg Glu Thr Ser Val Asp Pro Asp Met Arg Lys Gly Leu Gln Glu
            210                 215                 220

Leu Lys Ala Lys Gly Lys Leu Val Asp Cys Lys Val Ser Ala Gln Lys
225                 230                 235                 240

Leu Leu Ser Leu Leu Glu Lys Asp Glu Phe Lys Ser Gly Ala His Val
            245                 250                 255

Asp Phe Tyr Asp Lys
            260

<210> SEQ ID NO 2
<211> LENGTH: 261
<212> TYPE: PRT
<213> ORGANISM: Mus musculus

<400> SEQUENCE: 2

Met Glu Ala Asp Gly Leu Gly Cys Ala Val Cys Val Leu Thr Gly Ala
1               5                   10                  15

Ser Arg Gly Phe Gly Arg Ala Leu Ala Pro Gln Leu Ala Arg Leu Leu
            20                  25                  30

Ser Pro Gly Ser Val Met Leu Val Ser Ala Arg Ser Glu Ser Met Leu
            35                  40                  45

Arg Gln Leu Lys Glu Glu Leu Gly Ala Gln Gln Pro Asp Leu Lys Val
    50                  55                  60

Val Leu Ala Ala Ala Asp Leu Gly Thr Glu Ala Gly Val Gln Arg Leu
65                  70                  75                  80

Leu Ser Ala Val Arg Glu Leu Pro Arg Pro Glu Gly Leu Gln Arg Leu
                85                  90                  95

Leu Leu Ile Asn Asn Ala Ala Thr Leu Gly Asp Val Ser Lys Gly Phe
            100                 105                 110

Leu Asn Val Asn Asp Leu Ala Glu Val Asn Asn Tyr Trp Ala Leu Asn
            115                 120                 125

Leu Thr Ser Met Leu Cys Leu Thr Ser Gly Thr Leu Asn Ala Phe Gln
            130                 135                 140

Asp Ser Pro Gly Leu Ser Lys Thr Val Val Asn Ile Ser Ser Leu Cys
145                 150                 155                 160

Ala Leu Gln Pro Tyr Lys Gly Trp Gly Leu Tyr Cys Ala Gly Lys Ala
            165                 170                 175

Ala Arg Asp Met Leu Tyr Gln Val Leu Ala Ala Glu Glu Pro Ser Val
            180                 185                 190

Arg Val Leu Ser Tyr Ala Pro Gly Pro Leu Asp Asn Asp Met Gln Gln

```
                195                 200                 205
Leu Ala Arg Glu Thr Ser Lys Asp Pro Glu Leu Arg Ser Lys Leu Gln
210                 215                 220

Lys Leu Lys Ser Asp Gly Ala Leu Val Asp Cys Gly Thr Ser Ala Gln
225                 230                 235                 240

Lys Leu Leu Gly Leu Gln Lys Asp Thr Phe Gln Ser Gly Ala His
                245                 250                 255

Val Asp Phe Tyr Asp
            260

<210> SEQ ID NO 3
<211> LENGTH: 262
<212> TYPE: PRT
<213> ORGANISM: Rattus norvegicus

<400> SEQUENCE: 3

Met Glu Gly Gly Arg Leu Gly Cys Ala Val Cys Val Leu Thr Gly Ala
1               5                   10                  15

Ser Arg Gly Phe Gly Arg Ala Leu Ala Pro Gln Leu Ala Gly Leu Leu
                20                  25                  30

Ser Pro Gly Ser Val Leu Leu Leu Ser Ala Arg Ser Asp Ser Met Leu
            35                  40                  45

Arg Gln Leu Lys Glu Glu Leu Cys Thr Gln Pro Gly Leu Gln Val
50                  55                  60

Val Leu Ala Ala Ala Asp Leu Gly Thr Glu Ser Gly Val Gln Gln Leu
65                  70                  75                  80

Leu Ser Ala Val Arg Glu Leu Pro Arg Pro Glu Arg Leu Gln Arg Leu
                85                  90                  95

Leu Leu Ile Asn Asn Ala Gly Thr Leu Gly Asp Val Ser Lys Gly Phe
            100                 105                 110

Leu Asn Ile Asn Asp Leu Ala Glu Val Asn Asn Tyr Trp Ala Leu Asn
        115                 120                 125

Leu Thr Ser Met Leu Cys Leu Thr Thr Gly Thr Leu Asn Ala Phe Ser
    130                 135                 140

Asn Ser Pro Gly Leu Ser Lys Thr Val Val Asn Ile Ser Ser Leu Cys
145                 150                 155                 160

Ala Leu Gln Pro Phe Lys Gly Trp Gly Leu Tyr Cys Ala Gly Lys Ala
                165                 170                 175

Ala Arg Asp Met Leu Tyr Gln Val Leu Ala Val Glu Glu Pro Ser Val
            180                 185                 190

Arg Val Leu Ser Tyr Ala Pro Gly Pro Leu Asp Thr Asn Met Gln Gln
        195                 200                 205

Leu Ala Arg Glu Thr Ser Met Asp Pro Glu Leu Arg Ser Arg Leu Gln
    210                 215                 220

Lys Leu Asn Ser Glu Gly Glu Leu Val Asp Cys Gly Thr Ser Ala Gln
225                 230                 235                 240

Lys Leu Leu Gly Leu Gln Arg Asp Thr Phe Gln Ser Gly Ala His
                245                 250                 255

Val Asp Phe Tyr Asp Ile
            260

<210> SEQ ID NO 4
<211> LENGTH: 261
<212> TYPE: PRT
<213> ORGANISM: Artificial Sequence
<220> FEATURE:
```

<223> OTHER INFORMATION: SPR homologue

<400> SEQUENCE: 4

Met Glu Gly Gly Leu Gly Arg Ala Val Cys Leu Leu Thr Gly Ala Ser
1               5                   10                  15

Arg Gly Phe Gly Arg Thr Leu Ala Pro Leu Leu Ala Ser Leu Leu Ser
            20                  25                  30

Pro Gly Ser Val Leu Val Leu Ser Ala Arg Asn Asp Glu Ala Leu Arg
        35                  40                  45

Gln Leu Glu Ala Glu Leu Gly Ala Glu Arg Ser Gly Leu Arg Val Val
    50                  55                  60

Arg Val Pro Ala Asp Leu Gly Ala Glu Ala Gly Leu Gln Gln Leu Leu
65                  70                  75                  80

Gly Ala Leu Arg Glu Leu Pro Arg Pro Lys Gly Leu Gln Arg Leu Leu
                85                  90                  95

Leu Ile Asn Asn Ala Gly Ser Leu Gly Asp Val Ser Lys Gly Phe Val
            100                 105                 110

Asp Leu Ser Asp Ser Thr Gln Val Asn Asn Tyr Trp Ala Leu Asn Leu
        115                 120                 125

Thr Ser Met Leu Cys Leu Thr Ser Ser Val Leu Lys Ala Phe Pro Asp
    130                 135                 140

Ser Pro Gly Leu Asn Arg Thr Val Val Asn Ile Ser Ser Leu Cys Ala
145                 150                 155                 160

Leu Gln Pro Phe Lys Gly Trp Ala Leu Tyr Cys Ala Gly Lys Ala Ala
                165                 170                 175

Arg Asp Met Leu Phe Gln Val Leu Ala Leu Glu Glu Pro Asn Val Arg
            180                 185                 190

Val Leu Asn Tyr Ala Pro Gly Pro Leu Asp Thr Asp Met Gln Gln Leu
        195                 200                 205

Ala Arg Glu Thr Ser Val Asp Pro Asp Met Arg Lys Gly Leu Gln Glu
    210                 215                 220

Leu Lys Ala Lys Gly Lys Leu Val Asp Cys Lys Val Ser Ala Gln Lys
225                 230                 235                 240

Leu Leu Ser Leu Leu Glu Lys Asp Glu Phe Lys Ser Gly Ala His Val
                245                 250                 255

Asp Phe Tyr Asp Lys
            260

<210> SEQ ID NO 5
<211> LENGTH: 16
<212> TYPE: PRT
<213> ORGANISM: Artificial Sequence
<220> FEATURE:
<223> OTHER INFORMATION: signal sequence

<400> SEQUENCE: 5

Lys Arg Pro Ala Ala Thr Lys Lys Ala Gly Gln Ala Lys Lys Lys Lys
1               5                   10                  15

<210> SEQ ID NO 6
<211> LENGTH: 4
<212> TYPE: PRT
<213> ORGANISM: Artificial Sequence
<220> FEATURE:
<223> OTHER INFORMATION: monopartite NLS
<220> FEATURE:
<221> NAME/KEY: VARIANT
<222> LOCATION: (2)..(2)
<223> OTHER INFORMATION: May also be R

```
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: May also be R

<400> SEQUENCE: 6

Lys Lys Xaa Lys
1

<210> SEQ ID NO 7
<211> LENGTH: 4
<212> TYPE: PRT
<213> ORGANISM: Artificial Sequence
<220> FEATURE:
<223> OTHER INFORMATION: ER retention peptide

<400> SEQUENCE: 7

Lys Asp Glu Leu
1
```

SENSORS, METHODS AND KITS FOR DETECTING NICOTINAMIDE ADENINE DINUCLEOTIDES

The invention relates generally to the field of metabolomics, molecular biology, cell biology and biosensors. More specifically, the invention relates to in vitro and in cellulo detection of the cofactors nicotinamide adenine dinucleotide (NAD) and nicotinamide adenine dinucleotide phosphate (NADP).

Nicotinamide adenine dinucleotide (reduced, NADH; oxidized, $NAD^+$) and nicotinamide adenine dinucleotide phosphate (reduced, NADPH; oxidized, $NADP^+$) are key ubiquitous cofactors participating in a multitude of redox reactions regulating the cell metabolism. Although NAD(H) and NADP(H) possess similar high redox potential, their structural difference allow the formation of two separated pools of redox carriers within the same cell compartment and the development of specific functions. The ratios of free $[NADH]/[NAD^+]$ and $[NADPH]/[NADP^+]$ are low (<1) and high (>10), respectively. These free ratios have high physiological importance as they regulate cellular redox homeostasis and thus can be considered as cellular metabolic readout (Lin et al. Curr Opin Cell Biol. 2003 Apr.; 15(2): 241-6). These opposite ratios explain why $NAD^+$ is mostly used for oxidative biosynthesis involved in glycolysis and in linking the citric acid cycle to oxidative phosphorylation. Accordingly, NADPH is involved in reductive biosynthesis (lipid, amino acids and DNA synthesis) and in the supply of the cellular oxidative defense systems. Beside their roles in enzymatic conversions, these cofactors were more recently described as important signaling molecules and gene expression regulators. It is also to note that an imbalance of the ratio $NADPH/NADP^+$ and $NADH/NAD^+$ has been correlated with multiple pathologies such as cancers, diabetes, cardiovascular and neurodegenerative diseases. See Ying et al. Antioxid Redox Signal. 2008 Feb.; 10(2):179-206 and Berger et al. Trends Biochem Sci. 2004 Mar.; 29(3):111-8.

Since NAD(P) is a cofactor for many important enzymes, its consumption is also often monitored in in vitro enzymatic assays with the goal of quantifying enzyme activity or to quantify the concentrations of selected metabolites. Different methods exist to measure NAD(P) concentrations and ratios. One method often used for the quantification of pyridine nucleotides relies on the specific absorbance property of the reduced cofactors NADH, NADPH ($\lambda$=340 nm). However, such assays are not very sensitive due to the low extinction coefficient of the cofactor and are also sensitive to the presence of other molecules absorbing at this wavelength. The cofactors can also be quantified by first separating them by HPLC and identification by mass spectrometry (LC/MS). See Sporty et al. J Sep Sci. 2008 Oct.; 31(18):3202-11. Another possibility is to use an enzyme cycling assay, where the oxidized cofactor is reduced by a specific dehydrogenase in presence of its substrate (Veech et al. Biochem J. 1969 December; 115(4):609-19). However, such assays are not a direct measurement of cofactor concentrations and ratios. As stated for the simple absorbance assays, the cycling assays are also prone to interference by molecules that absorb light or that fluoresce, leading to measurement errors. Recently, an assay was developed using this principle coupled with a luminescence assay (Vidugiriene et al. Assay Drug Dev Technol. Dec. 1, 2014; 12(9-10): 514-526). In this assay, the reduced cofactor (NADH or NADPH) is used to convert a proluciferin substrate into luciferin through the action of a reductase and the reduced cofactor is regenerated through the action of another enzyme. The generated luciferin will produce photons by the reaction catalyzed by a luciferase. While this method reduces the problem of interference of absorbing molecules, it suffers from another shortcoming: only total NAD or NADP concentrations are measured. Measurements of the ratio of cofactors, or concentrations of only the reduced or oxidized species require additional steps. These steps usually involve heating of the sample under basic or acidic conditions and are prone to yield unreliable results. Also, these methods cannot be used to measure directly the enzyme activity of NAD/NADP-dependent dehydrogenases as often done in clinical tests e.g. lactate dehydrogenase, or glucose-6-phosphate dehydrogenase.

US2014/329718 discloses a genetically encoded fluorescent sensor for NADH, comprising a polypeptide sensitive to environmental NADH, and a segment that exhibits the environmental NADH by change in its spectral characteristics, wherein the polypeptide sensitive to NADH is:

(1) a polypeptide comprising Rossman domain with NADH binding feature, and/or
(2) a polypeptide derived from an NADH sensitive protein of transcription regulatory factor Rex family, or its functional fragment or NADH binding domain; and wherein the segment that exhibits the environmental NADH by change in the spectral characteristic is a fluorescent protein sequence or a derivative thereof. However, this sensor only measures NADH and does not permit measuring NADP(H) or $NAD(P)^+$ concentrations. It also shows slow kinetics.

The present inventors therefore aimed at providing a sensor that can be used in simple, one-step assay to reliably measure the concentration of $NAD^+$, $NADP^+$ and/or the ratios of the concentrations of $NAD^+/NADH$ and $NADP^+/NADPH$ in complex samples, like biological samples.

It was surprisingly found that a sensor based on the enzyme sepiapterin reductase (SPR) is advantageously used for detecting the co-factors $NAD^+$, and $NADP^+$ and the ratios of the concentrations of $NAD^+/NADH$ and $NADP^+/NADPH$ in complex samples. More in particular, a sensor was developed comprising SPR and a ligand for SPR, the ligand being capable of intramolecular binding to the active site of the SPR. Importantly, ligand binding showed a high co-factor dependency/specificity in the sense that it binds essentially only in the presence of the oxidized redox form of the nicotinamide adenine dinucleotide. The ligand does not bind in the presence of the other redox form, or in the absence of cofactor. Furthermore, binding of the ligand to SPR changes the spectroscopic properties of the sensor molecule, which change can be readily detected, e.g. by a change in fluorescence anisotropy, or a change in RET (FRET, BRET).

Wild-type SPR is specific for NADP(H), but it was found that several mutations of the cofactor binding site permitted to switch its specificity to NAD(H) and to further increase its affinity for this cofactor. This permitted the generation of sensors for both $NADPH/NADP^+$ and $NADH/NAD^+$ ratios.

Several rounds of optimizations yielded sensors for NADP(H) and NAD(H) which are highly sensitive, highly specific, pH-independent, compatible for high-throughput screening and with good kinetics. Among others, these sensors can be used in multiple applications, such as the measurement of the cofactor ratios or changes in light-absorbing samples (e.g. lysate, serum), enzymatic assays, clinical tests and in living cells.

Accordingly, in one embodiment the invention provides a sensor molecule for fluorescence or luminescence-based detection of a nicotinamide adenine dinucleotide analyte, in particular for detecting the concentrations of NAD+, NADP+ and the ratios of the concentrations of NAD+/NADH and NADP+/NADPH, the sensor comprising (i) a binding protein (BP) for the nicotinamide adenine dinucleotide analyte, the BP being derived from sepiapterin reductase (SPR; EC 1.1.1.153); (ii) a SPR ligand (SPR-L) capable of intramolecular binding to said BP in the presence of the oxidized form of said analyte; and
(iii) at least one fluorophore.

For example, there is provided a sensor molecule for fluorescence or luminescence-based detection of the concentration of NADP+ and/or the ratios of the concentrations NADP+/NADPH, the sensor comprising
(i) a binding protein (BP) for NADP+, the BP being a wild-type sepiapterin reductase (SPR; EC 1.1.1.153) or a functional homolog, fragment, derivative or variant thereof, showing the desired cofactor-binding properties
(ii) a SPR ligand (SPR-L) capable of intramolecular binding to said BP in the presence of the oxidized form of said analyte; and
(iii) at least one fluorophore.

As another example, there is provided is a sensor molecule for fluorescence or luminescence-based detection of the concentration of NAD+, and/or the ratios of the concentrations of NAD+/NADH, the sensor comprising
(i) a binding protein (BP) for NAD+, the BP being a mutant sepiapterin reductase (SPR; EC 1.1.1.153) or a functional homolog, fragment, derivative or variant thereof, showing the desired cofactor-binding properties
(ii) a SPR ligand (SPR-L) capable of intramolecular binding to said BP in the presence of the oxidized form of said analyte; and
(iii) at least one fluorophore.

WO2015/007317 discloses a sensor molecule for detecting an analyte of interest in a sample using BRET, the sensor comprising a proteinaceous moiety tethered to a synthetic regulatory molecule, wherein (i) the proteinaceous moiety comprises a luciferase enzyme (Luc) attached to binding protein (BP) capable of binding the analyte of interest; (ii) the synthetic regulatory molecule comprises a ligand (L) capable of intramolecular binding to BP, and a fluorescent acceptor that can accept the energy from the Luc through resonance energy transfer in the presence of the appropriate Luc substrate, and (iii) wherein the binding of analyte to BP changes the degree of intramolecular binding of L to BP of the BRET sensor molecule, thereby resulting in a change in BRET efficiency. Several specific L-BP pairs are described, but the art is silent about the use of SPR-L and/or SPR.

A sensor of the invention is among others characterized in that it comprises a polypeptide derived from or based on the enzyme sepiapterin reductase (SPR; EC 1.1.1.153) or a mutant thereof as binding protein for the nicotinamide adenine dinucleotide analyte. SPR is a homodimeric NADPH-dependent oxidoreductase of 261 residues belonging to the short-chain dehydrogenases/reductases (SDR) family and catalyzes the reduction of 6-pyruvoyltetrahydropterin in the final step of the de novo biosynthesis of the cofactor tetrahydrobiopterin (BH4). SPR possesses a characteristic Rossmann dinucleotide-binding domain. Wild-type human SPR has a KD of 1 μM for NADPH and a KD of 10 μM for NADP+. The specificity of NADP(H) over NAD(H) is due to specific interactions with conserved basic residues (Arg42, Arg17) for the additional 2'-phosphate found in NADP(H). See Tanaka et al. Structure. 1996 Jan. 15; 4(1):33-45.

Sulfa drugs have been shown to inhibit SPR, namely by binding to the substrate binding site of SPR through specific interactions with active sites residues (Ser157, Tyr170, Asp257). See Haruki et al. Science 2013 May 24; 340 (6135):987-91. Haruki et al. (supplementary material (pp. 1-20) to Science 2013 May 24; 340 6135) disclose a SNAP-based competition assay based on a FRET-pair formed by the FRET donor molecule SPR-labeled with terbium cryptate and the FRET acceptor SPR-ligand sulfasalazine conjugated via SNAP-tag to EGFP. The crystal structures of SPR with bound sulfa drugs as described in the art do not predict the degree of specificity for NADP+ in any manner nor is there any mention of lack of binding of drug in the presence of NADPH. Also, the lack of affinity of the ligand in the absence of cofactor was neither reported nor could it be predicted. Furthermore, Haruki et al. does not relate to measuring NAD(P)+ and NAD(P)+/NAD(P)H. The sensor proposed by Haruki et al. is solely discussed in relation to the screening for new SPR inhibitors by determining the capacity of candidate inhibitors to compete with sulfalazine for binding to SPR. Although such binding is performed in the presence of known concentrations of NADPH and NADP+ as cofactor, this does not imply in any way the use of the FRET pair to detect concentrations of (free) NADP+.

Only the surprising selectivity of the (tethered) ligands for NADP+ over NADPH or no cofactor enables the generation of a sensor for NADP+ or NADP+/NADPH ratios. Accordingly, the current finding that tethered derivatives of sulfa drugs exclusively bind intramolecularly to SPR bound with oxidized nicotinamide adenine dinucleotide (NAD(P)+) but do not bind to free SPR or SPR bound to reduced cofactor was totally unexpected.

In one embodiment, the biosensor comprises as BP a human sepiapterin reductase (hSPR; UniprotKB accession number P35270) or a functional homolog, fragment, derivative or variant thereof, e.g. an ortholog or a mutant SPR sequence showing the desired cofactor-binding properties. SPR from various organisms are described in the literature with a close overall structure and conserved substrate binding and catalytic mechanism (e.g. for hSPR Ser157, Tyr170, Lys 174, Asp257).

Suitable mammalian orthologs include SPR from mouse (mSPR; UniprotKB accession number Q64105) and rat (rSPR; UniprotKB accession number P18297), both with 74% sequence identity compared to the hSPR (EMBO J. 1997 Dec. 15; 16(24):7219-30). Indeed, it was found that both mouse and rat SPR specifically bind tethered sulfonamides intramoleculary only in the NADP+ bound state.

A sequence comparison of the human (SEQ ID NO:1), mouse (SEQ ID NO:2) and rat SPR (SEQ ID NO:3) sequences results in the following sequence alignment, wherein the functionally conserved (black highlight) and semi-conserved (gray highlight) amino acid residues are indicated. The three residues marked with an asterisk indicate the so-called catalytic triad.

| SPR_Human | -MEGGLGRAVCLLTGASRGFGRTLAPLASLLSPGSVILSARNEEALRQIEAELGAELGQQLIGEIERELPRPEGLQRLLLIN |
| SPR_Mouse | MEADGLGCAVCVLTGASRGFGRALAPQLARLLSPGSMLVSARSESMLRQLKEELGAQQPDLIVLAAADLGIEAGVQRLLSAVRELPRPEGLQRLLLIN |
| SPR_Rat   | MECERLGCAVCVLTGASRGFGRALAPQLACLLSPGSVILLSARSDSMLRQLKEELCTQQPGLIVLAAADLGIEEGVQQLLSAVRELPRPERLQRLLLIN |

| SPR_Human | NAGSLGDVSKGFLNEDLSTQVNNYWALNITSMLCLTSSVIKAEPDSPGLNETVVNISSLCALQPEKGFALYCALGGWGLYCAGKAARDMLYQVLAEEPSVRVLIYAPG |
| SPR_Mouse | NAATLGDVSKGFLNENDLAEVNNYWALNITSMLCLTSGTLNAFQDSPGLSKTVVNISSLCALQEEKGWGLYCAGKAARDMLYQVLAEEPSVRVLSYAPG |
| SPR_Rat   | NAGTLGDVSKGFLNENDLAEVNNYWALNITSMLCLTTGTLNAFSESPGLSKTVVNISSLCALQPPKGWGLYCAGKAARDMLYQVLAEEPSVRVLSYAPG |

| SPR_Human | PLDTDMQQIARETSEDTRKGELKELAKGLVDCKVSAQKLLSLIEKDEFSGAHVDFYDK |
| SPR_Mouse | PLNDMQQLARETSKDPELRSKLQKLKSEGALVDCGTSAQKLLIECLLQKDTFQSGAHVDFYD- |
| SPR_Rat   | PLDTMQQLARETSEDPELRSKLQKINSEGLVDCGTSAQKLLSLLCREDTFQSGAHVDFYDI |

However, besides mammalian origin, SPR from non-mammalian sources can also be used. One example is the SPR from silkworms (*Bombyx mori*; BmSPR UniprotKB accession number COSTP5) with 35% sequence identity compared to hSPR. Another example is the SPR from *Chlorobium tepidium* (BmSPR UniprotKB accession number Q8KES3), an anaerobic phototrophic thermophile bacterium, of which crystallographic data revealed a relative close structural fold compared to human and mouse SPR, but only 28% sequence identity (PDB: 2BDO; Supangat, et al., J Biol Chem. 2006 Jan. 27; 281(4):2249-56).

Hence, in one embodiment, the sensor comprises (i) a sepiapterin reductase (SPR; EC 1.1.1.153) or a mutant thereof as binding protein for the nicotinamide adenine dinucleotide analyte; (ii) a SPR ligand (SPR-L) capable of intramolecular binding to said active site of SPR or SPR mutant, wherein said binding selectively occurs only in the presence of the oxidized form of said nicotinamide adenine dinucleotide analyte; and (iii) at least one fluorophore. Analyte-dependent binding of said SPR-L to SPR or SPR mutant modulates the spectroscopic properties of the fluorophore or emission spectra of the sensor molecule. More in particular, SPR-L selectively binds to the active site of SPR or SPR mutant in the presence of the oxidized form of said analyte, i.e. in the presence of $NADP^+$ or $NAD^+$, and wherein the reduced form of the analyte (NADPH, NADH) can displace $NADP^+$ or $NAD^+$ from SPR or SPR mutant, thereby disabling binding of the intramolecular ligand. In the absence of the oxidized form of said analyte (presence of $NADP^+$ or $NAD^+$) no binding of the intramolecular ligand is observed.

The terms "functional fragment", "derivative" and "analog" mean proteins that retain substantially the same biological function or activity of the native SPR protein in the invention. Functional fragments, derivatives or analogs of SPR in the invention may be (i) proteins with one or more conservative or non-conservative amino acid substitution (preferably conservative), where the substituted amino acid residues may or may not be one encoded by the genetic code, or (ii) proteins containing substitutions of one or more amino acid residues having a substituent group, or (iii) proteins formed having the mature protein fused with another compound (such as compounds that extend half-life of the protein, for example, polyethylene glycol), or (iv) proteins formed by having said protein fused with additional amino acid sequence (such as leader sequence or secretory sequence, or sequence used for purification of the protein or proprotein sequence, or fusion protein formed with fragment of antigen IgG). In accordance with the teachings provided herein, these functional fragments, derivatives and analogs are well known to a person skilled in the art.

Hence, when referring to a SPR polypeptide or protein, this includes variants of the polypeptide or protein with the same function but differ in sequence. These variants, e.g. variants of SEQ ID NO:1, 2 or 3, include, but are not limited to, sequences obtained by deleting, inserting and/or substituting one or more (typically 1-30, preferably 1-20, more preferably 1-10, and most preferably 1-5) amino acid(s) in the sequence of the polypeptide or protein, and by adding one or more (usually less than 20, preferably less than 10, and more preferably within 5) amino acid(s) to its C-terminus and/or N-terminus. For example, in the art, substitution with amino acids of comparable or similar properties usually does not change the function of the polypeptide or protein. Amino acids with similar properties usually refer to a family of amino acids having similar side chains and have been clearly defined in the art. These families include amino acids with basic side chains (e.g., lysine, arginine, histidine), amino acids with acidic side chains (e.g., aspartate, glutamate), amino acids with uncharged polar side chain (e.g., asparagine, glutamine, serine, threonine, tyrosine, cysteine), amino acids with non-polar side chains (e.g., alanine, valine, leucine, isoleucine, proline, phenylalanine, methionine, tryptophan), amino acids with 6-branched side chains (e.g., threonine, valine, isoleucine), and amino acids with aromatic side chains (e.g., tyrosine, phenylalanine, tryptophan, histidine).

As another example, adding one or more amino acids to the C-terminus and/or N-terminus usually does not change the function of the polypeptide or protein either. As known to a person skilled in the art, genetic cloning process often requires design of suitable endonuclease sites, which will eventually introduce one or more irrelevant residues to the terminus of the polypeptide or protein to be expressed, but this does not affect the activity of the target polypeptide or protein. For another example, in order to construct a fusion protein, to promote the expression of a recombinant protein, to obtain a recombinant protein that can secrete itself into the extracellular environment of the host cells, or to facilitate the purification of a recombinant protein, it is often desirable to have the N-terminus, C-terminus, or other suitable regions of the protein added with some amino acids, for example, including, but not limited to, suitable connecting peptides, signal peptides, leader peptides, the terminal extensions, the glutathione S-transferase (GST), maltose E binding protein, Protein A, tags such as 6His or Flag, or protease cleavage sites, e.g. a factor Xa or thrombin or TEV protease or enterokinase protease cleavage site. Variants of SPR may include: homologous sequences, conservative variants, allelic variants, natural mutants, induced mutants, polypeptide or protein encoded by a DNA which could hybridize with the DNA for said polypeptide or protein under high or low stringent conditions, as well as the polypeptide or protein derived from antiserum against said polypeptide or protein. These variants may also comprise polypeptide or protein whose sequence is at least about 70%, at least about 75%, at least about 80%, at least about 85%, at least about 90%, at least about 95%, at least about 98%, at least about 99%, or 100% sequence identity with a polypeptide according to SEQ ID NO: 1, 2 or 3.

Preferably, the SPR for use in a sensor of the invention comprises the residues corresponding to Ser157, Tyr170, Lys 174, Asp257 in the human SPR (SEQ ID NO: 4). Preferably, the SPR comprises a Rossmann dinucleotide-binding domain, which is a well characterized fold (structural motif) formed by two repeats of ßαßαß and containing a glycine-rich pyrophosphate-binding loop sequence (GX1-3GX1-3G) See Bellamacina et al. FASEB J. 1996 Sep.; 10(11):1257-69, or Bottoms et al. Protein Sci. 2002 Sep.; 11(9):2125-37

In one embodiment, the SPR shows at least 80%, preferably at least 85%, more preferably at least 90% sequence identity with one of the above mammalian SPR sequences (SEQ ID NO: 1, 2 or 3), in particular with human SPR (SEQ ID NO: 4). The SPR preferably comprises at least 80%, preferably at least 85%, more preferably at least 90% sequence identity with the conserved residues identified based on sequence comparison of known (mammalian) SPRs.

The BP sensitive to nicotinamide adenine dinucleotide for use in a sensor of the present invention may have following characteristics:

(1) containing polypeptide derived from human SPR wherein the polypeptide may be encoded by the sequence (SEQ ID NO: 4)
MEGGLGRAVCLLTGASRGFGRTLAPLLASLLSPGSVLVLSARNDEALRQ

LEAELGAERSGLRVVRVPADLGAEAGLQQLLGALRELPRPKGLQRLLLI

NNAGSLGDVSKGFVDLSDSTQVNNYWALNLTSMLCLTSSVLKAFPDSPG

LNRTVVNISSLCALQPFKGWALYCAGDMLFQVLALEEPNVRVLNYAPGP

LDTDMQQLARETSVDPDMRKGLQELKAKGKLVDCKVSAQKLLSLLEKDE

Figure 2A:
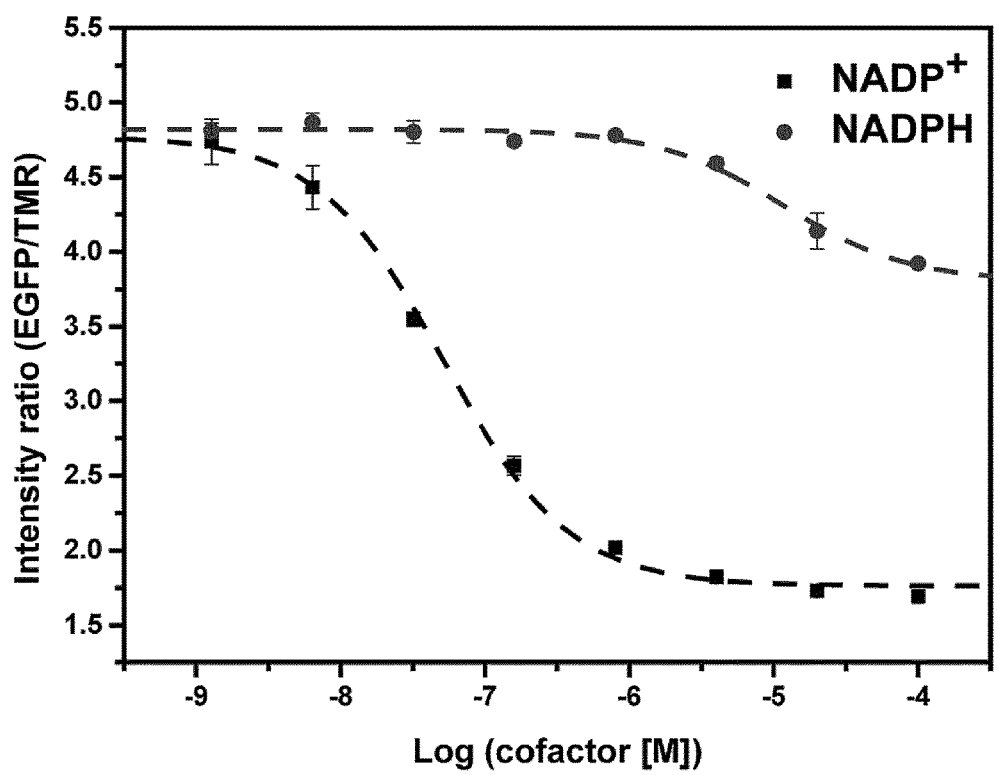

FKSGAHVDFYDK (2) a homologous or non-homologous sequence that is 95% identical to the sequence described in (1) in at least 85 amino acid residues;

(3) any homologous or non-homologous sequence that is 90% identical to the sequence described in (1) in at least 85 amino acid residues;

(4) any homologous or non-homologous sequence that is 70% identical to the sequence described in (1) in at least 85 amino acid residues;

(5) any homologous or non-homologous sequence that is 50% identical to the sequence described in (1) in at least 85 amino acid residues;

(6) any homologous or non-homologous sequence that is 40% identical to the sequence described in (1) in at least 85 amino acid residues; or (7) any homologous or non-homologous sequence that is 35% identical to the sequence described in (1) in at least 85 amino acid residues A sensor of the invention comprises a (tethered) SPR ligand (SPR-L) capable of selective intramolecular binding to said BP in the presence of the oxidized form of analyte. In one embodiment, SPR-L is any moiety that binds the complex of SPR with NAD(P)$^+$ with at least 20-times higher affinity than the complex of SPR with NAD(P)H or the complex of SPR without any cofactor bound. As can be seen in FIG. 2A, the sensor with sulfamethoxazole as tethered ligand closes at concentrations of NADP$^+$ of around 100 nM whereas it is closing at NADPH concentrations of only 10 μM or higher. Taking the 10-fold higher affinity of SPR for NADPH over NADP$^+$ into account, the difference in affinity of tethered sulfamethoxazole or sulfapyridine for SPR-NAD(P)$^+$ over SPR-NAD(P)H is thus at least two orders of magnitude. Furthermore, our data show that for the SPR-NADP$^+$ complex the tethered ligand favours the closed state (with intramolecular ligand bound) over the open state (with intramolecular ligand not bound) 100:1 whereas in the absence of cofactor the open state is favoured and the tethered ligand is not bound. Thus, the difference in affinity of tethered SPR-L for SPR-NAD(P)$^+$ over free SPR is at least two orders of magnitude.

For example, provided is a sensor wherein SPR-L selectively binds to the active site of (mutant) SPR in the presence of NADP$^+$ or NAD$^+$, and wherein the reduced form of the analyte (NADPH, NADH) can displace NADP$^+$ or NAD$^+$ from (mutant) SPR, thereby disabling binding of the intramolecular ligand. Furthermore, in the absence of the oxidized form of said analyte (presence of NADP$^+$ or NAD$^+$) no binding of the intramolecular ligand is observed.

As is exemplified herein below, the binding specificity of a sensor of the invention for either the redox pair NAD$^+$/NADH or the redox pair NADP$^+$/NADPH can be modulated by modulating SPR.

In one embodiment, the invention provide a sensor molecule for fluorescence or luminescence-based analyte detection, wherein analyte detection comprises detecting the concentration of NADP$^+$ or the NADPH/NADP$^+$ ratio, the sensor comprising a sepiapterin reductase capable of binding NADP$^+$. Said SPR preferably contains basic residues at positions 17 and 42 based on the human sequence of SEQ ID NO: 4. More preferably, a sensor for detecting NADP$^+$ or the NADPH/NADP$^+$ ratio comprises a sequence based on or derived from SPR wherein positions 17 and 42 are Arg. In a specific aspect, the NADP$^+$ sensor comprises wild-type SPR, preferably the amino acid sequence of SEQ ID NO:4.

In another embodiment, the invention provide a sensor molecule for fluorescence or luminescence-based analyte detection, wherein analyte detection comprises detecting the concentration of NAD$^+$ or the NADH/NAD$^+$ ratio, the sensor comprising a sepiapterin reductase capable of binding NAD$^+$. Said SPR preferably contains at position 41 (numbering based on the human SPR sequence of SEQ ID NO: 4) an Asp and/or at position 42 a hydrophobic residue such as Val, Ile or Trp. More preferably, the sensor comprises Asp41 and at position 42 a Val, Ile or Trp. For example, in a specific embodiment the sensor comprises mutant SPR with Asp at position 41 and Trp at position 42 (SPR (D41W42)).

Any SPR ligand capable of selectively binding to the active site of SPR in the presence of only the oxidized form of the analyte can be suitably used in a sensor of the invention. The ligand can be of proteinaceous or non-proteinaceous nature. The ligand can be a non-proteinaceous SPR inhibitor, or based thereon, i.e. the inhibitor can be functionalized or modified to allow for site-specific covalent attachment to the other sensor elements, e.g. via a protein self-labelling tag. Self-labelling protein tags are known in the art, such as SNAP-tag, CLIP-tag or Halo-Tag. Other methods for site-specifically attaching SPR-L to the protein such as those based on unnatural amino acids or cysteine residues are known to those skilled in the art.

In one aspect, SPR-L is (based on) a benzene sulfonamide or analog thereof, preferably selected from one of the following:

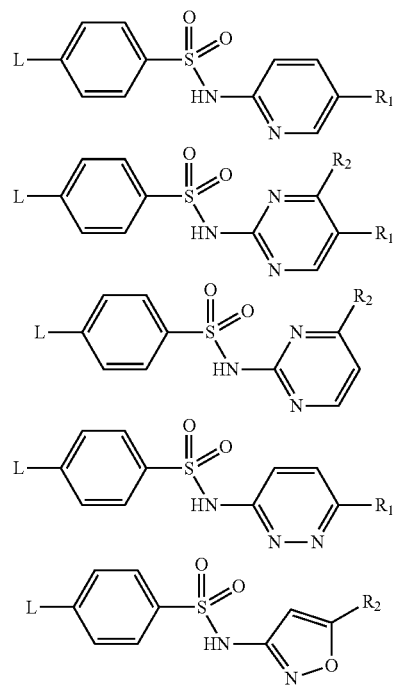

-continued

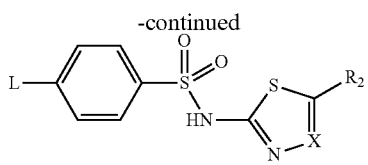

R1 = H, Me, OMe, Cl, Br
R2 = H, Me
X = C, N
L = Linker

The linker (L) for example contains a O⁶-benzylguanine (BG) or O⁴-benzyl-2-chloro-6-aminopyrimidine (CP) moiety for SNAP-tag labeling and a fluorophore.

Particularly useful SPR ligands for use in a sensor of the invention are those based on a benzenesulfonamide moiety that is shown to bind to SPR with a high specificity for NADP⁺. These include sulfasalazine, sulfathiazole, sulfamethoxazole, sulfamethizole, phthalylsulfathiazole, sulfapyridine, sulfadiazine, sulfamerazine, sulfachloropyridazine, sulfameter, chlorpropamide, glibenclamide, tolbutamide. Preferred SPR-ligands include sulfapyridine and sulfamethoxazole.

The expression "based on" in the context of the SPR-L definition is meant to indicate that, once being part of the sensor, the benzene sulfonamide structure is not present in its entirety, since part of structure will participate in covalent incorporation in the sensor molecule.

To allow for application of the sensor in the physiological pH-range (6.8-8.0), it is preferred that the SPR-L is a sulfonamide having a pKa below 6 or above 9. In one embodiment, the sulfonamide has a pKa below 6, for example sulfamethoxazole having a pKa of around 5.6.

In a preferred embodiment, the sensor comprises a self-labelling protein tag to which a synthetic molecule comprising the SPR-L and a fluorophore is attached. The synthetic molecule can be tethered via the appropriate reactive group to the remainder of the sensor, e.g. a proteinaceous part comprising SPR or a mutant thereof, and a fluorescent protein. In one embodiment, the self-labeling protein tag is based on a human O⁶-alkylguanine-DNA-alkyltransferase (hAGT) to which the synthetic molecule is tethered via a reactive group for hAGT. For example, the protein tag is a SNAP-tag or CLIP-tag. Preferably, the reactive group is a O⁶-benzylguanine (BG), O⁴-benzyl-2-chloro-6-aminopyrimidine (CP) or 02-benzylcytosine (BC) derivative. In another embodiment, the self-labeling protein tag is based on a modified haloalkane dehalogenase to which the synthetic molecule is tethered via a chloroalkane (Halo-Tag).

A sensor of the invention is characterized among others in that analyte-dependent binding of said SPR-L to BP modulates the spectroscopic properties of the fluorophore or emission spectra of the sensor molecule. This modulation results in a detectable signal, or a change in a detectable signal.

For example, in one embodiment the spectroscopic properties of the fluorophore sensor are modulated e.g. involving fluorescence anisotropy. To that end, the sensor may contain a synthetic fluorophore as part of the structure tethering the ligand to the sensor (see also Brun et al *J Am Chem Soc* 131, 5873-5884, 2009). Preferred fluorophores are rhodamine derivatives, Alexa dye derivatives, Bodipy derivatives or other fluorophores known to those skilled in the art.

In another embodiment, the emission spectra of the sensor molecule are modulated. For example, the sensor provides for resonance energy transfer (RET) based analyte detection. In a preferred aspect, the RET sensor comprises a segment A connected via a linker to a segment B, wherein each of segment A and segment B comprises a member of a RET pair comprising a donor moiety and an acceptor moiety, further characterized in that (i) segment A comprises the BP and (ii) segment B comprises the SPR-L, such that the donor moiety and the acceptor moiety are in a suitable juxtaposition to yield a RET signal when SPR-L is bound to BP, and wherein an analyte-induced change in SPR-L binding to BP results in a change in RET efficiency.

Thus, the SPR-L is capable of intramolecular binding to BP essentially only in the presence of the oxidized form of said nicotinamide adenine dinucleotide analyte, such that the donor moiety and the acceptor moiety are in a suitable juxtaposition to yield a RET signal when SPR-L is bound to BP in the presence of the oxidized form. The absence of sufficient concentrations of the oxidized form, or the replacement of the oxidized with the reduced form, alters said SPR-L binding to the BP, thereby inducing a conformational change of the sensor sufficient to modulate RET between the donor and acceptor moieties, thus resulting in a RET signal change.

In a specific aspect, the sensor provides for fluorescence resonance energy transfer (FRET) based analyte detection. FRET is a distance-dependent interaction between the electronic excited states of two dye molecules in which excitation is transferred from a donor molecule to an acceptor molecule without emission of a photon. The efficiency of FRET is dependent on the inverse sixth power of the intermolecular separation, making it useful to monitor an analyte-induced conformational change in a sensor molecule of the invention. In most applications, FRET can be detected by the appearance of sensitized fluorescence of the acceptor or by quenching of donor fluorescence. Primary conditions for FRET are that donor and acceptor molecules must be in close proximity (typically 10-100 Å) and that the absorption spectrum of the acceptor must overlap the fluorescence emission spectrum of the donor. In addition, donor and acceptor transition dipole orientations must be approximately parallel. For example, a sensor is provided wherein the A segment comprises a fluorescent acceptor and wherein the B segment comprises a fluorescent donor, or vice versa. Any FRET pair known in the art can be used. The criteria for choosing an appropriate FRET pair are the presence of a spectral overlap between the emission spectrum of the donor and the excitation spectrum of the acceptor and the good spectroscopic properties (e.g. brightness, photostability). A FRET fluorophore can be of proteinaceous nature or a chemical fluorophore. Fluorescent proteins for use in FRET-based sensors are well known in the art, like green fluorescent protein (GFP) and GFP variants that are derived from *Renilla reniformis* of *Aequorea*-based family or a member of the Anthozoa-based fluorescent protein family.

Exemplary chemical fluorophores comprise Alexafluor, Rhodamine, BODIPY, Tetramethylrhodamine, Cyanin dyes, Fluorescein, Quantum dots, IR dyes, FM dyes, ATTO dye. FRET pairs of known fluorophores can be established based on their light excitation and emission profile. Exemplary useful FRET pairs are: tetramethylrhodamine derivatives (TMR)/silicon-rhodamine (SiR); carbopyronine derivatives (CPY)/SiR; Cy3/Cy5; fluorescein/TMR; Alexa488/TMR; Alexa488/Alexa546; Alexa488/Alexa594; ATTO488/ATTO565; TT0565/ATTO647N; ATTO594/ATTO647N; CFP/YFP; EGFP/TMR; TagGFP2/TagRFP; mNeonGreen/mRuby2.

In one embodiment, the FRET pair is selected from (i) a fluorescent protein and a synthetic molecule containing a fluorophore that is site-specifically attached; (ii) a synthetic molecule containing a first fluorophore that is site-specifically attached, and a second fluorophore that forms a FRET pair with the first fluorophore and that is site-specifically attached to site different from the site to which the first fluorophore is attached; (iii) two fluorescent proteins.

In a specific aspect, the FRET pair is selected from (i) a fluorescent protein and a self-labelling tag (e.g. SNAP-tag, CLIP-tag or Halo-tag) tethered with a synthetic molecule containing a fluorophore; (ii) two orthogonal self-labelling tags, one for the attachment of the synthetic molecule containing a donor moiety, the other to attach an acceptor moiety fluorophore (for example SPR-Halo-p30-SNAP or SNAP-p30-CLIP-SPR); and (iii) two fluorescent proteins.

In a specific embodiment, the invention provides a ratiometric sensor for NAD(H) and NADP(H), composed of a fusion protein comprising (i) SPR or a mutant of SPR as cofactor-binding protein, (ii) a fluorescent protein or orthogonal self-labelling tag and (iii) SNAP-tag to which a synthetic molecule containing the SPR inhibitor sulfapyridine and a fluorophore is attached. Remarkably, the intramolecular SPR ligand sulfapyridine only binds to the active site of the SPR in the presence of the oxidized cofactor (NAD$^+$ or NADP$^+$) and does not bind in presence of the reduced cofactor (NADH, NADPH), or in the absence of cofactor, as monitored by the FRET ratio changes (FIG. 2A). The titration with free sulfamethoxazole shown in FIG. 2B results in a sensor that shows the same FRET ratio change as the sensor in the absence of cofactor, further demonstrating that in the absence of cofactor the sensor does not close. Furthermore, since the reduced and oxidized cofactor will compete for the same cofactor-binding site on SPR, the sensor is able to probe directly the ratio NADPH/NADP$^+$ or NADH/NAD$^+$.

A limitation of FRET is the requirement for external illumination to initiate the fluorescence transfer, which can lead to background noise in the results from direct excitation of the acceptor or to photobleaching. To avoid this drawback, a sensor of the invention can be based on Bioluminescence Resonance Energy Transfer (BRET). In BRET, the donor fluorophore of the FRET pair is replaced by a bioluminescent donor protein (BDP) which, in the presence of a substrate, excites the acceptor fluorophore through the same resonance energy transfer mechanisms as FRET.

Accordingly, in one embodiment the invention provides a BRET-based sensor wherein each of the segments A and B comprises a member of a BRET pair comprising a bioluminescent donor protein (BDP) and a fluorescent acceptor, both of which are well known in the art. Generally, the BDP is a luciferase, for example the luciferase from *Renilla reniformis*. Alternative BDPs that can be employed in this invention are enzymes which can act on suitable substrates to generate a luminescent signal. Specific examples of such enzymes are beta-galactosidase, alkaline phosphatase, beta-glucuronidase and beta-glucosidase. Synthetic luminescent substrates for these enzymes are well known in the art and are commercially available from companies, such as Tropix Inc. (Bedford, Mass., USA).

In a preferred embodiment, the BDP has luciferase activity. Luciferases, and nucleic acid constructs encoding them, are available from a variety of sources or by a variety of means. Examples of bioluminescent proteins with luciferase activity may be found in U.S. Pat. Nos. 5,229,285; 5,219,737; 5,843,746; 5,196,524; or 5,670,356. Preferred luciferases include NanoLuc luciferase, *Renilla* luciferase, firefly luciferase and *Gaussia* luciferase. Also encompassed are non-naturally occurring luciferases, e.g. a mutated luciferase.

In a particular embodiment, a sensor of the invention comprises the previously described NanoLuc™ Luciferase (Nluc), a 19.1 kDa, monomeric, ATP independent enzyme that utilizes a novel substrate to produce high intensity, glow-type luminescence. See WO 2012/061530 and Hall et al. ACS Chem Biol. 2012; 7(11):1848-57. The enzyme was generated using directed evolution from a deep-sea shrimp luciferase, creating a luciferase that is much brighter than other forms of luciferase, including both firefly (*Photinus pyralis*) and *Renilla reniformis*. The high intensity luminescence of the NanoLuc enzyme combined with low autoluminescence of the furimazine substrate allows the sensitive detection of low levels of luciferase. In a specific aspect, an extra protein domain is attached to the C-terminus of Nano-Luc to decrease unspecific interactions of NanoLuc with other molecules, e.g. biological molecules present in a biological sample. For example, very good results are obtained with attaching circular-permutated dihydrofolate reductase (cpDHFR), which is derived from wild-type *E. coli* DHFR by fusing the original N and C termini with a (glycine)5 linker and splitting between Asn23 and Leu24. In another embodiment, the extra protein is CLIP-tag.

The other BRET pair member, i.e. the fluorescent acceptor, can be a synthetic fluorophore or a fluorescent protein as mentioned above. Preferred BRET fluorescent acceptors include Cy3, TMR, Alexa488, Alexa546, ATTO488, ATTO565. See Example 8 herein below for a representative BRET-sensor and the use thereof in detecting NAD+ levels or an NAD+-consuming enzyme. In one embodiment, the BRET pair is formed by Cy3 and NanoLuc.

The skilled person will understand that many different sensor geometries are possible to achieve a functional sensor of the invention, i.e. a sensor that relies on the surprising specificity of SPR-L for BP bound to the oxidized redox form of the analyte. Sensor geometries can be optimized according to needs. Preferably, the geometry is one that minimizes the distance of the RET pair members in the closed state and maximizes the distance of the RET pair members in the open state. There are various ways to achieve this. In one embodiment, the SPR-L and BP are each located at the opposite termini of the sensor. This geometry typically enhances the analyte-induced modulation of the spectroscopic properties of the fluorophore or emission spectra of the sensor molecule as compared to a sensor comprising SPR-L and/or BP as "internal" elements flanked on both sides by other sensor elements.

The linker connecting segments A and B is designed to ensure that analyte-induced change in intramolecular binding of SPR-L to (mutant) SPR causes a sufficient change in the conformational state of the sensor. It can be a proteinaceous or non-proteinaceous linker. In a preferred aspect, it is a proteinaceous linker such as an artificial polypeptide sequence or a naturally occurring protein. Poly-L-proline linkers can be used as precise molecular rulers due to their well-defined property of forming a stable and rigid helical structure (the polyproline II helix) with a pitch of 3.1 Å per residue in aqueous solution. Accordingly, the linker moiety is preferably a helical linker rich in prolines, which leads to structural rigidity and isolation of the synthetic regulatory molecule from the attached luciferase. Very good results were obtained with a poly-L-Proline linker consisting of at least 15 Pro residues, for instance Pro15, or Pro30 or even longer. Brun et al. (2011) investigated polyproline linkers of varying length (0, 6, 9, 12, 15, 30, 60) that were inserted between SNAP- and CLIP-tag in the conventional SNIFIT-sensors. It was found that a length of 30 or 60 proline residues yielded an improved maximum ratio change of the sensor. Accordingly, in one embodiment the linker moiety consists of a poly-L-Pro linker comprising at least 15, preferably at least 20, more preferably at least 30, residues.

The sensor molecule may further comprise an organelle targeting means, preferably a targeting means for targeting the sensor to the mitochondria, nucleus, plasma membrane or ER. In one embodiment, the sensor comprises a nuclear localization signal or sequence (NLS) which 'tags' the sensor for import into the cell nucleus by nuclear transport. Typically, this signal consists of one or more short sequences of positively charged lysines or arginines exposed on the protein surface. For example, it comprises the prototype of the ubiquitous bipartite signal sequence KR[PAATKK-AGQA]KKKK (SEQ ID NO: 5), or the consensus sequence K-K/R-X-K/R for monopartite NLS (SEQ ID NO: 6). ER targeting can be achieved by using the human calreticulin ER targeting signal (in N-terminus) or the KDEL (SEQ ID NO: 7) ER retention peptide (in C-terminus). The 25 first amino acids of the human CoX8A (or tandem repeats of this sequence) are suitably used for mitochondrial targeting.

The invention also relates to a method for providing a sensor molecule of the invention. The proteinaceous moiety can be prepared using standard recombinant DNA techniques well known to those skilled in the art. For example, the SPR coding sequence or functional part thereof can be genetically introduced into the multiple cloning site of a bacterial expression vector comprising a fluorescent protein coding sequence. Other proteinaceous components, like a protein labeling tag and/or linker sequences, can also be incorporated using standard techniques. The DNA constructs for various configurations of the proteinaceous moiety of a sensor of the invention can be transfected/transformed in suitable cell lines (eukaryotic or prokaryotic) for its production. The various configurations of the fusion proteins produced in cells, are then purified or semipurified from the transfected/transformed cells. A convenient procedure to purify a proteinaceous moiety is by affinity chromatography e.g. using a His- and/or Strep-tag engineered in the DNA construct. Standard biochemical techniques can be also used alone or in combination with affinity chromatography to purify to various levels the various fusion proteins.

As is exemplified by the Examples, the elements of a sensor comprising a proteinaceous moiety and a synthetic molecule (or precursor thereof) comprising SPR-L are typically produced as separate entities, after which the synthetic molecule is tethered to the proteinaceous molecule using the appropriate coupling reaction. Finally, these purified fusion proteins can be also chemically or enzymatically modified before their tethering to the synthetic regulatory molecule. In another embodiment, the proteinaceous moiety is produced by a combination of in vivo and in vitro methods. First a fusion protein is genetically engineered and expressed in cells using recombinant techniques. The fusion protein is then purified or semi-purified before being modified by chemically or enzymatically attaching a further proteinaceous element, e.g. an element which can serve as a binding protein such as an antibody. Attachment of the further element can be peptide-based or chemically-based.

Another specific aspect of the invention relates to the use of ratiometric RET sensors for detecting the concentration of a nicotinamide adenine dinucleotide analyte, in particular for detecting the concentrations of $NAD^+$, $NADP^+$ and/or the ratios of the concentrations of $NAD^+/NADH$ and $NADP^+/NADPH$ in complex samples that absorb light at the emission wavelengths of the sensor, e.g. cell lysates, serum or other bodily fluids. Analysis of such samples is prone to artefacts and often leads to unreliable assay outcomes. Whereas sensors based on luciferases as an internal light source (i.e. BRET) would in theory reduce the fluorescent background problem and potentially increase sensitivity, no ratiometric BRET-based sensors have yet been introduced that are suitably used for the quantification of analytes in light-absorbing samples.

It was surprisingly found that by absorbing a BRET-based sensor of the invention to a solid carrier such as paper or by immobilizing the BRET sensors prior to measurement to a solid carrier such as a glass surface, interference from absorbance of the sample at the emission wavelength of the sensor is minimized. This then allows for analysis of complex samples, like serum.

In a specific aspect, the sensor molecule is immobilized or absorbed to a solid carrier, preferably glass, a transparent plastic, a gold surface, paper or a gel, more preferably to chromatography or filter paper. Also provided is an analytical device comprising a sensor molecule according to the invention, wherein the sensor molecule is arranged in such a manner that, when the device is in use for detecting an analyte of interest in a sample, the photons that are emitted from the sensor molecule and that are collected by a detector pass through the sample for a distance shorter than 330 μm. For example, the sensor molecule is immobilized or absorbed to a solid carrier, preferably a glass or transparent plastic. In one aspect, the sensor molecule is absorbed to a paper carrier or a gel, preferably to chromatography or filter paper. In another aspect, the sensor molecule is comprised in a thin film, or confined in a tube, capillary or (microfluidic) chamber.

Also provided herein is a method for fluorescence or luminescence-based in vitro (ex vivo) detection of the concentration of a nicotinamide adenine dinucleotide analyte, in particular for detecting the concentrations of $NAD^+$, $NADP^+$ and the ratios of the concentrations of $NAD^+/NADH$ and $NADP^+/NADPH$, in a sample, the method comprising (a) contacting the sample with a sensor molecule according to the invention under conditions allowing for an analyte-dependent binding of said SPR-L to BP (e.g. comprising SPR or mutant SPR) modulates the spectroscopic properties of the fluorophore or emission spectra of the sensor molecule; and (b) analyzing a change in a signal generated by modulation of the spectroscopic properties of the fluorophore or emission spectra of the sensor molecule, optionally further comprising relating the signal change to the concentration of a nicotinamide adenine dinucleotide analyte in the sample.

For example, the sample is a biological sample or a fraction thereof, preferably a bodily fluid, more preferably selected from the group consisting of blood, serum, saliva, urine, spinal fluid, pus, sweat, tears, breast milk. Typically, a sample to be analyzed in a method according to the invention comprises (i) an unknown concentration of NAD+, NADP+, NADH; (ii) an unknown ratio of the concentrations of NAD+/NADH or NADP+/NADPH, and/or (iii) an unknown concentration of an enzyme that generates or consumes NADP+ or NAD+.

Preferably, the sensor molecule is arranged in such a manner that, when the device is in use for detecting an analyte of interest in a sample, the photons that are emitted from the sensor molecule and that are collected by a detector pass through the sample for a distance shorter than 330 μm.

Also provided herein is a kit of parts comprising a sensor molecule according to the invention and a solid carrier, preferably wherein said solid carrier is paper or a transparent object, more preferably chromatography or filter paper, a glass or transparent plastic. In one embodiment, the kit comprises a BRET-based sensor, further comprising a luciferase substrate, preferably coelenterazine, furimazine or derivative thereof.

The skilled person will appreciate that a sensor, method or kit of the invention for detecting the concentration of a nicotinamide adenine dinucleotide analyte has a wide range of applications, ranging from scientific research and drug development to clinical analysis and diagnostic testing. Exemplary applications include detection of NADP(H) or NAD(H), detection of NADP(H) or NAD(H) in physiological state, detection of NADP(H) or NAD(H) at a subcellular level, in situ detection of NADP(H) or NAD(H), screening of drugs, diagnostics of diseases associated with NADP(H) or NAD(H) level.

Provided is the use of a sensor molecule according to the invention for the fluorescence or luminescence-based detection of a nicotinamide adenine dinucleotide analyte, for example detecting the concentrations of NAD+, NADP+ and/or the ratios of the concentrations of NAD+/NADH and NADP+/NADPH.

Hence, the invention also relates to the use of a sensor, method and/or kit according to the invention in one or more of the following: (i) ex vivo clinical or diagnostic testing, preferably performed in serum or bodily fluid; (ii) an ex vivo enzymatic assay that involves the formation or consumption of $NADP^+$ or $NAD^+$; (iii) ex vivo high-throughput screening, preferably for compounds that can modulate NADP(H) or NAD(H) in cells or for the validation of the toxicity profile of therapeutic drugs; (iv) ex vivo live cell measurements, preferably comprising the use of a widefield fluorescence microscope, confocal fluorescence microscope or a Fluorescence Lifetime Imaging Microscopy (FLIM) system with appropriate excitation and emission filters. In one embodiment, a sensor is used to detect ex vivo activity of a dehydrogenase, such as lactate dehydrogenase (LDH or LD). LDH is an enzyme found in nearly all living cells (animals, plants, and prokaryotes). LDH catalyzes the conversion of lactate to pyruvic acid and back, as it converts NADH to NAD+ and back. LDH has been of medical significance because it is found extensively in body tissues, such as blood cells and heart muscle. Because it is released during tissue damage, it is a marker of common injuries and disease such as heart failure.

DETAILED DESCRIPTION OF THE INVENTION

The numerous functions of the nicotinamide adenine nucleotides in cell metabolism and in vitro assays and the lack of reliable and precise methods for their quantification in vitro and in living cells, motivated us to develop a ratiometric NADP(H) biosensor taking advantage of the established SNIFITs design principle (M. Brun et al. J Am Chem Soc 131, 5873 (Apr. 29, 2009))

Human sepiapterin reductase (SPR) was chosen as a specific NADP binding protein to generate the sensor, taking advantage of information available concerning its structure and the description of different inhibitors. The initial sensor, composed of a fusion protein with a self-labeling protein (SNAP-tag), a fluorescent protein (EGFP) and the sepiapterin reductase (SPR) as NADP(H)-binding protein, is labelled with a molecule containing a SPR ligand and a fluorophore (tetramethylrhodamine, TMR) (FIG. 1A). Intramolecular binding of the attached ligand to SPR brings the fluorophore and the fluorescent protein in close proximity, producing a high Förster resonance energy transfer (FRET) efficiency. On contrary, when the ligand does not bind to SPR, the FRET pairs are separated by a greater distance, producing a low FRET efficiency.

The inventors now surprisingly found that when this fusion protein is labeled with a molecule containing the SPR ligand sulfapyridine and a fluorophore (tetramethylrhodamine, TMR), the attached ligand only binds to SPR in presence of $NADP^+$, bringing the fluorophore and the fluorescent protein in close proximity, thereby producing a high Förster resonance energy transfer (FRET) efficiency (FIG. 1A). On contrary, in the absence of $NADP^+$, the ligand is unable to bind to SPR, leading to greater distance between the FRET pairs, producing a low FRET efficiency. Furthermore, in presence of only NADPH, the ligand is unable to bind to SPR, leading to greater distance between the FRET pairs, producing a low FRET efficiency. Furthermore, in the presence of both cofactors but at concentrations of NADPH much higher than those of $NADP^+$ the ligand is unable to bind to SPR, leading to greater distance between the FRET pairs, producing a low FRET efficiency. It is thus the surprising specificity of the ligand for SPR-$NADP^+$ over SPR-NADPH and over free SPR that permits to construct a sensor for $NADP^+$ concentrations and $NADP^+$/NADPH ratios.

Figure 1B:
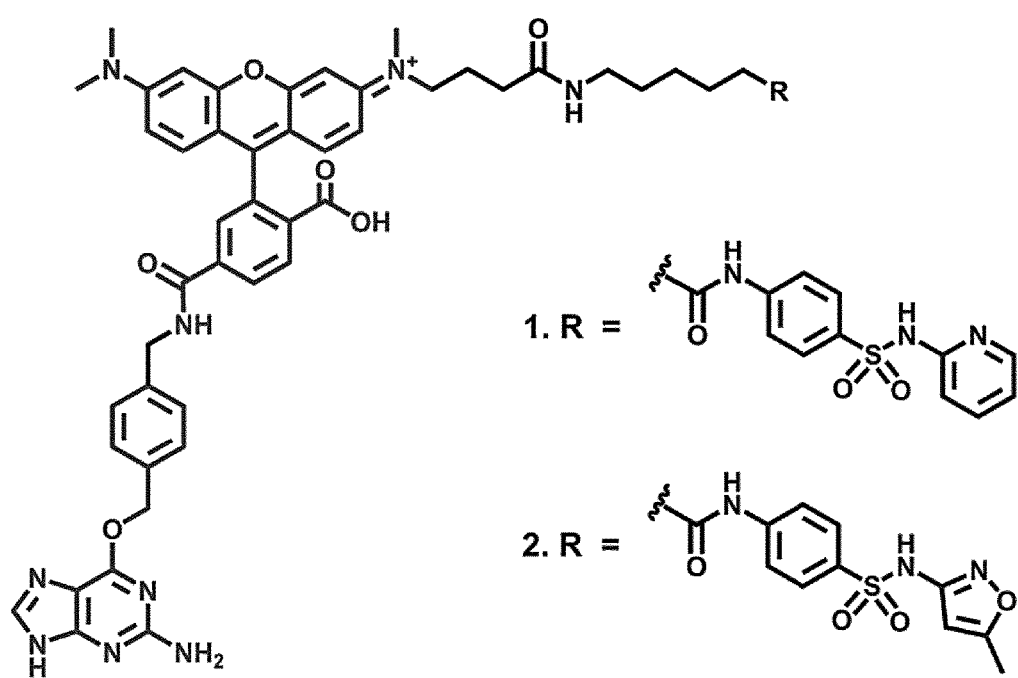

To decrease the FRET efficiency in the open state of the sensor and thereby increasing the observed total ration change of the sensor, as previously shown for other SNI-FITs, a poly-L-proline linker forming relatively stable and rigid helical structure (the polyproline II helix) was placed in the fusion protein between SNAP-tag and EGFP to increase the distance between the fluorophores. This resulted in the following protein: SNAP-p30-EGFP-SPR; p30 being a polyproline linker composed of 30 proline residues. To form functional sensor, a synthetic molecule containing a $O^6$-benzylguanine (BG) moiety for the specific covalent attachment to SNAP-tag, a tetramethylrhodamine (TMR) derivative and sulfapyridine (SPY), as SPR ligand was synthesized (BG-TMR-C6-SPY) (see FIG. 1B, Scheme 1).

Figure 1C:
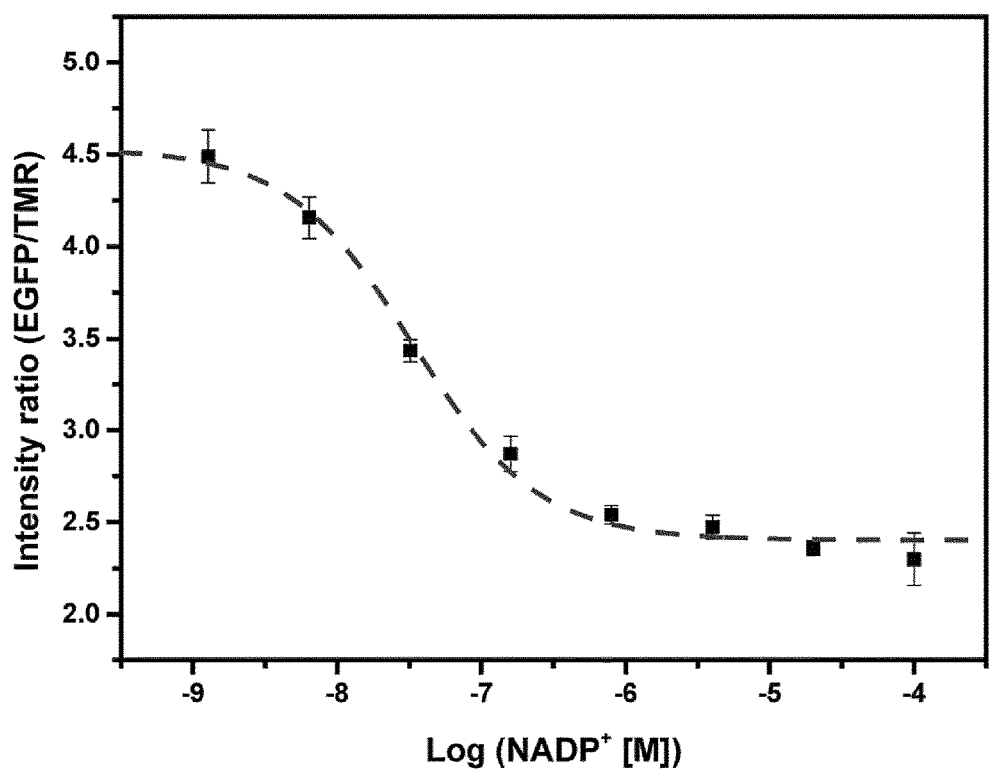
Figure 2B:
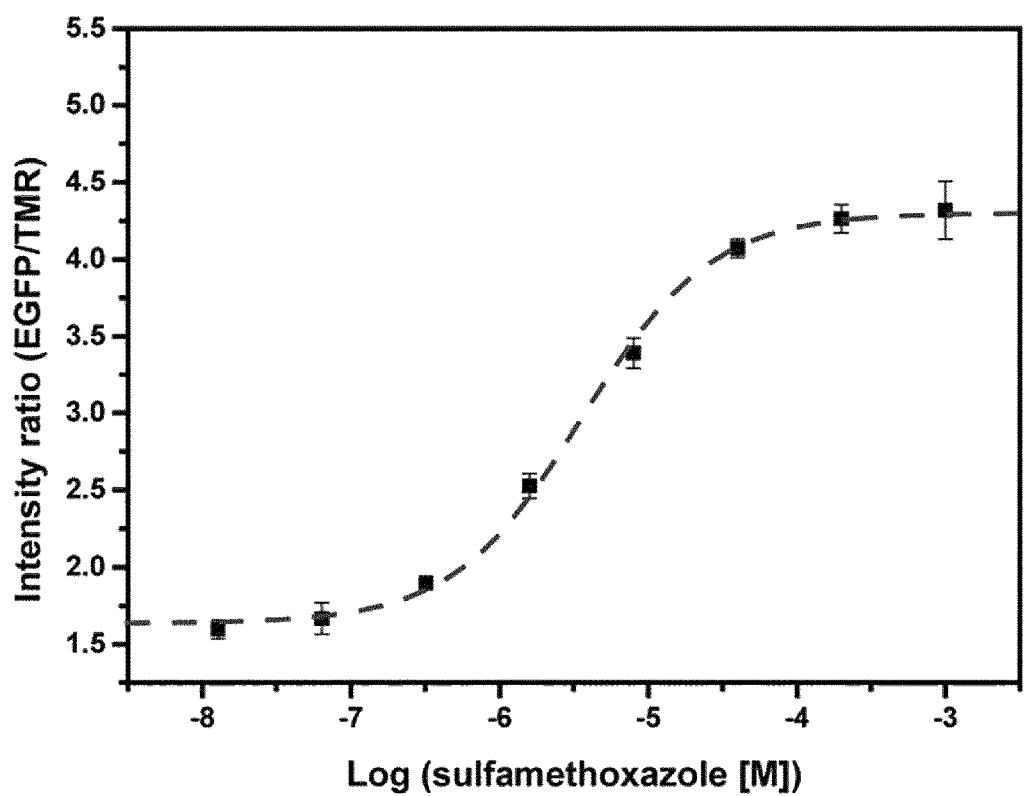
Figure 3A:
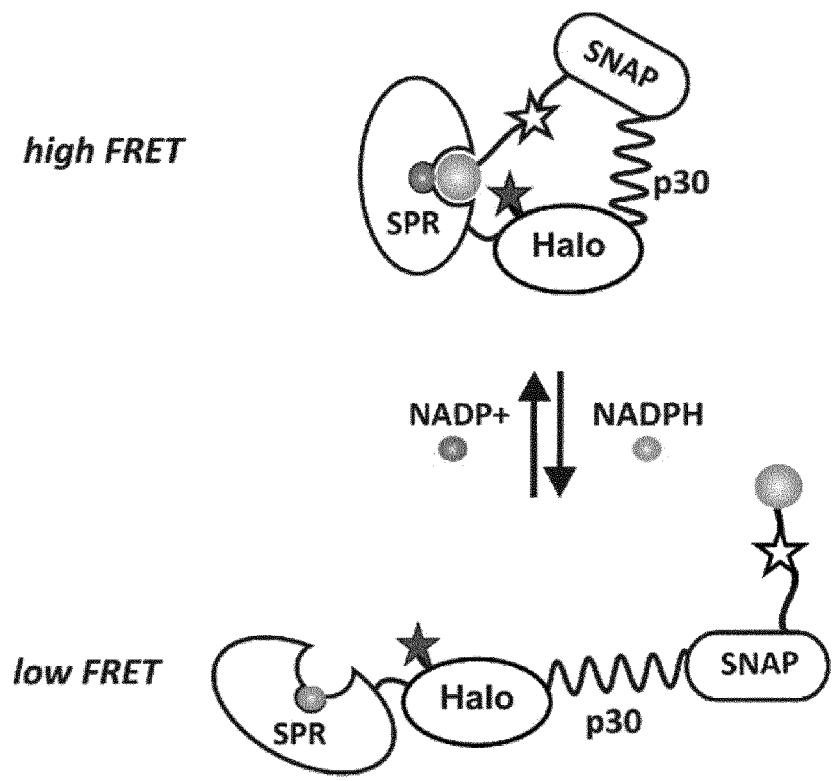

As stated above, it was found by performing titration experiments of the labelled SNAP-p30-EGFP-SPR with $NADP^+$ and NADPH (FIG. 1), that the intramolecular ligand (e.g. sulfapyridine) only binds to SPR together with the oxidized cofactor ($NADP^+$), as determined by the change in the FRET ratio. On the contrary, even at high concentration of NADPH (100 µM), the intramolecular ligand does not bind to SPR, determined by an unchanged FRET ratio (FIG. 2A). Furthermore, a similar FRET ratio is obtained if a high concentration of a free SPR ligand is added in presence of a fixed concentration of $NADP^+$ to compete with the intramolecular ligand and fully switch the sensor in an open conformation (FIG. 2B). Thus, the measured FRET ratio correlates with the ratio of NADPH and $NADP^+$ in the solution (FIG. 1A, 3A). In addition, it has been found that the affinity of the ligand for SPR in presence $NADP^+$ is suitable to monitor the physiological range of NADPH/$NADP^+$ ratio (1-100) (e.g. in lysate or living cells).

pH Sensitivity

Figure 1D:
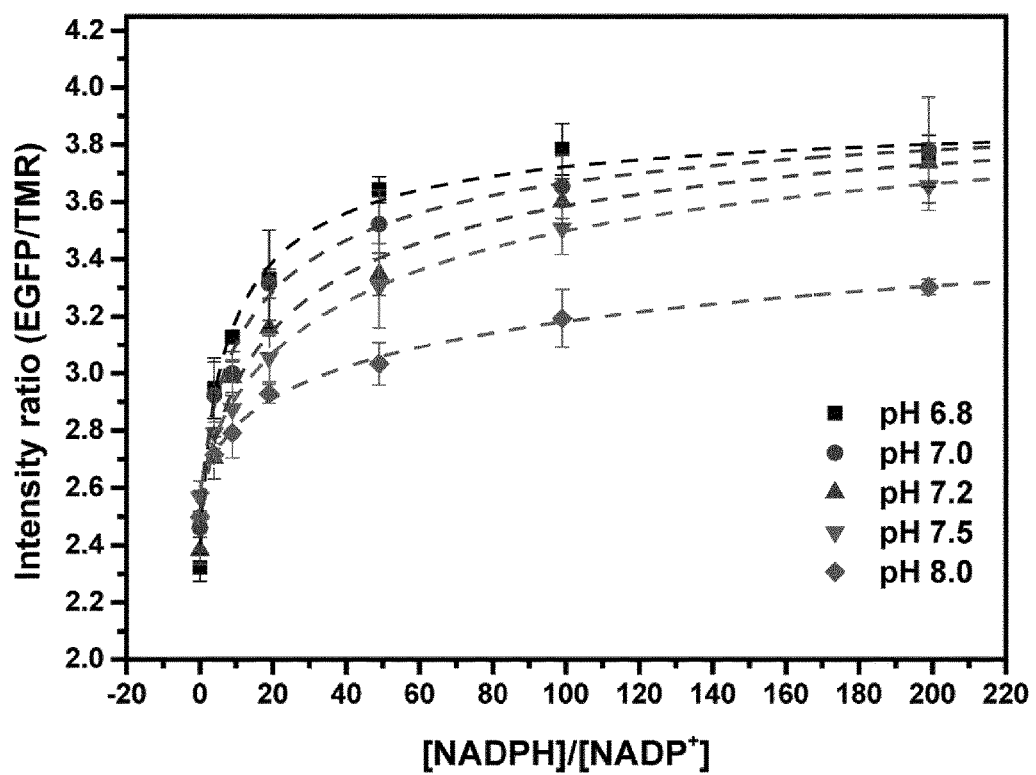
Figure 1E:
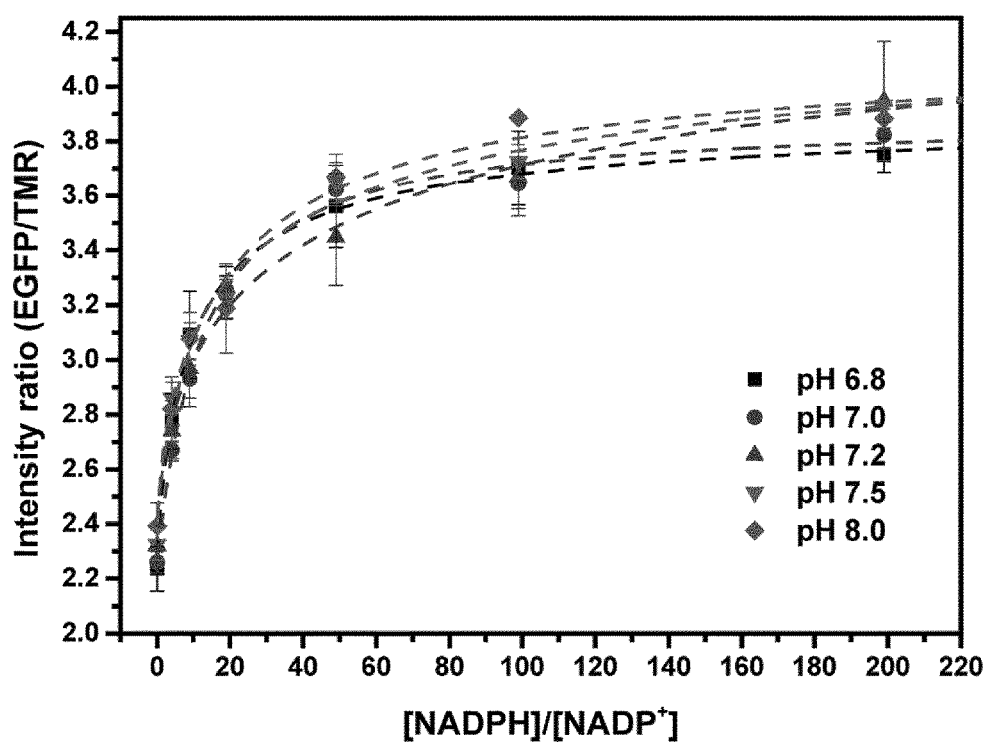

However, it was found that the sensor response using sulfapyridine (SPY) as intramolecular ligand was affected by pH variations (6.8-8.0) decreasing its usefulness for cofactor quantification (FIG. 1D). For example, using the same sensor to monitor the cofactor ratio inside the cytosol and mitochondria would not be possible as these organelles have different pH, respectively 7.2-7.4 and 8.0. We hypothesized that the apparent change in the affinity of the intramolecular ligand could be due to the pKa of the sulfonamide moiety. For sulfapyridine, the pKa of the sulfonamide proton is 8.4 with a higher affinity for the anionic form of the sulfonamide. Using another sulfonamide with a pKa below 6 should solve the pH sensitivity of the sensor in the physiological pH range (6.8-8.0). We chose the sulfamethoxazole (SMX) since it has a sulfonamide pKa around 5.6 and a relatively similar affinity. The titration of the sensor labelled with BG-TMR-C6-SMX with NADPH/NADP$^+$ showed pH-independent responses (FIG. 1E).

Sensor Specificity

Figure 2C:
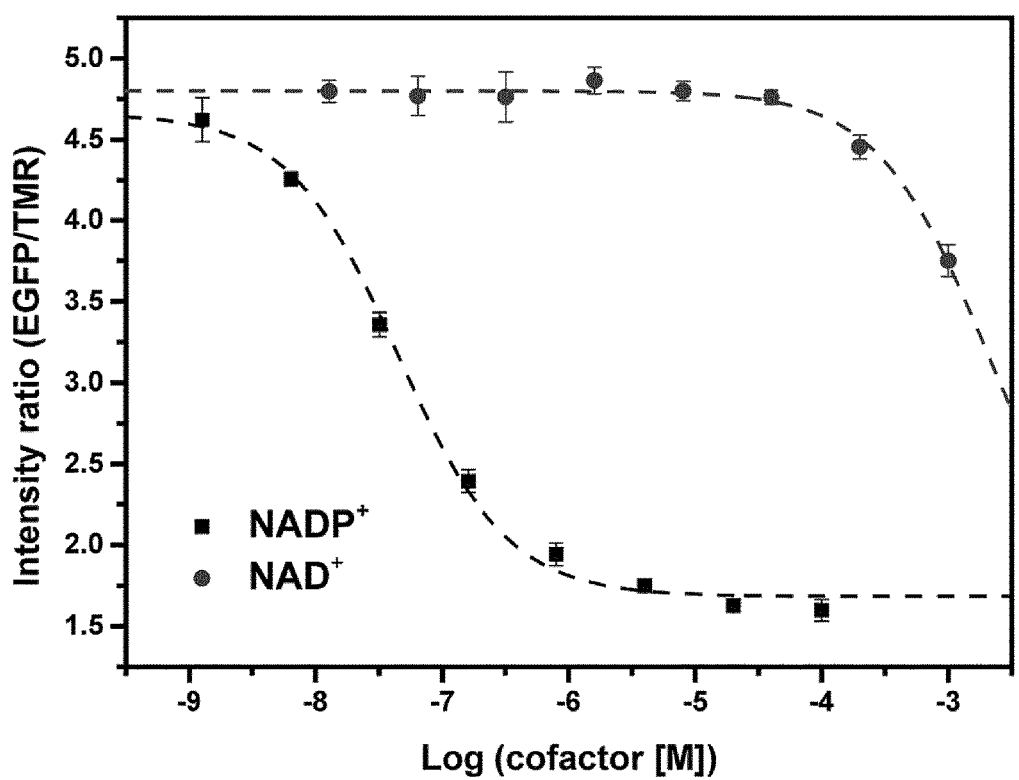

The specificity of the sensor is a crucial parameter in a complex sample (e.g. lysate, serum) or in cells where several nucleotides are structurally close to NADP(H) and could potentially influence the sensor's response. To test the specificity, the sensor was titrated with known and structurally close nucleotides up to concentration physiologically relevant (or even higher): NAD$^+$, NADH, ADP, GTP and ATP (FIG. 2C,D). Overall, the sensor displays high specificity for NADP$^+$, even compared to very close relatives such as NAD$^+$. Only NAD$^+$ was able to slightly close the sensor at the highest concentration (1 mM). However, this concentration would be too high to occur in an in vitro assay or in cells and additionally NAD would not be able to compete with NADP$^+$.

FRET Ratio Change Optimization

The initial sensor SNAP-p30-EGFP-SPR showed a maximal FRET ratio change of 1.8 between the open and closed state (FIG. 1C). The geometry of the sensor was optimized to maximize the FRET ratio change and to obtain a sensor with improved sensitivity for in vitro and cellular applications. The strategy was to decrease the distance between the two FRET pairs in the closed state by linking the fluorescent protein directly at the C-terminus of SPR close to the binding site of the intramolecular ligand. For this purpose two different constructs SPR-EGFP-p30-SNAP and SNAP-p30-SPR-EGFP were cloned, expressed in E. Coli and purified. Following the labelling of the constructs with the intramolecular ligand (BG-TMR-C6-SMX), titration experiments were performed with NADP$^+$ in order to quantify the FRET ratio change (FIG. 2C). The results showed significant improvement of the FRET ratio change of the new sensors by increasing the FRET efficiency in the closed state (ΔRmax: 2.8 and 3.5, respectively).

Having a sensor that could be used to measure the NADPH/NADP$^+$ ratio in complex light-absorbing sample such as serum or lysate are required for reliable and sensitive measurements in enzymatic assays (e.g. routine clinical tests).

However, it has been determined that the GFP/TMR FRET pair is not ideal due to the absorbance and autofluorescence of diverse metabolites (e.g. bilirubin, flavins, etc.) at this wavelengths. To solve this problem and to further optimize the FRET ratio change of the NADP-sensor, we chose to replace EGFP by Halo-tag (SPR-Halo-p30-SNAP) (FIG. 3A). Halo-tag is another self-labelling tag allowing specific covalent attachment of chloroalcane derivatised molecules. Since, the binding site of Halo-tag is closer to its N-terminus, we were able to further decrease the distance of the fluorophores in the closed state. The Halo-tag was labelled with a silicon-rhodamine (SiR) fluorophore functionalized with a chloroalcane moiety (SiR-Halo) providing a more red-shifted FRET pair, thus more sensitive in serum or lysates. Using Halo-tag has several advantageous features such as the fast labelling kinetics, the improved geometry of the construct and the high cell-permeability of the derivatised fluorophore. The sensor SPR-Halo-p30-SNAP performed well in titrations displaying a high FRET ratio change between the closed and open state (ΔRmax: 8.0) (FIG. 3C).

As alternative to increase the sensitivity and avoid interference in complex samples, a bioluminescent version of the best sensor could be produced by replacing the Halo-Tag by a luciferase (e.g. NanoLuc; SPR-NLuc-p30-SNAP). Similarly to LUCIDs, the sensor can then be placed on a solid support such as a paper strip to reduce the light path through the sample and reduce the effect on the emitted light ratio.

NAD-Sensor

Figure 4:
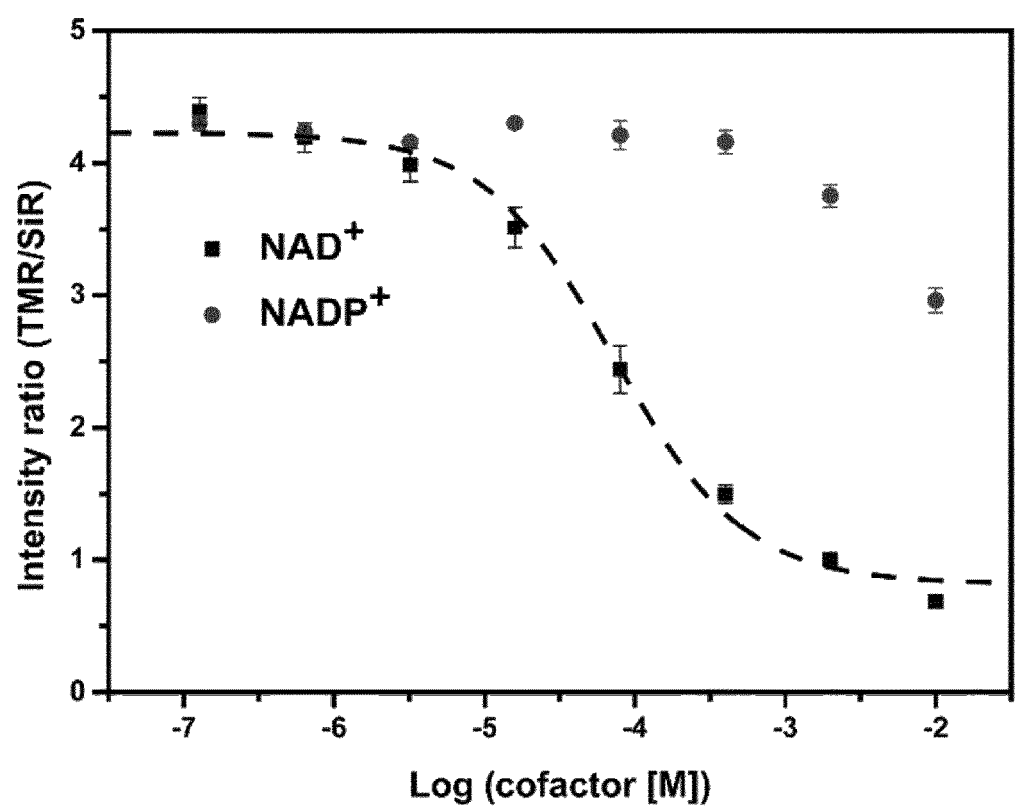

A sensor for NAD(H) was developed by switching the specificity of SPR by site-directed mutagenesis. For SPR, two arginines (Arg$^{17}$ and Arg$^{42}$ in the human SPR sequence) are crucial for the specificity of NADP(H) as they interact directly with the additional 2'-phosphate. All the NADP-dependent enzymes of the short-chain dehydrogenase/reductase family have a highly conserved arginine (Arg$^{42}$) and another conserved arginine or lysine (Arg$^{17}$ or Lys$^{17}$). However, the NAD-dependent enzymes of the same family have no conserved residue in position 42 or 17, but a highly conserved aspartic acid (Asp$^{41}$). Information from crystal structures showed that this specific aspartate is able to bind the 2'-hydroxyl group of NAD(H) in a bidentate manner. In addition, the negative charge of the aspartate would repel the negative charges of a potential phosphate yielding a high specificity for NAD(H) over NADP(H). As initial trial, the SPR mutant with Asp$^{41}$ and Ala$^{42}$ results in a sensor with low affinity, but high specificity for NAD$^+$. To increase the affinity of the cofactor, it was found that at the position 42, the presence a hydrophobic residue like valine, isoleucine or tryptophan are common as they can do hydrophobic interactions with the adenine moiety. The presence of a Trp$^{42}$ seems to increase the affinity of NAD by forming an effective π-stacking with the adenine. Therefore, we produced SPR(D41W42)-Halo-p30-SNAP by site-directed mutagenesis and titrated the sensor with NADP$^+$ and NAD$^+$ after the labelling with BG-TMR-C6-SMX. We could observe a complete switch of the specificity of the mutated sensor compared to wild-type and an increase affinity for NAD$^+$ compared to previous SPR mutant (FIG. 2C, 4). In this case, the NAD-based FRET sensor can be easily transformed to a BRET sensor by exchanging the Halo-Tag by a luciferase (e.g. NanoLuc; SPR(D41W42)-NLuc-p30-SNAP).

Several strategies can be exploited to modulate the affinity of the sensor for the analyte. One possibility is to perform mutations at the cofactor binding site or at the ligand binding site to change the sensor affinity. Another possibility is to use a sulfonamide ligand of suitable affinity.

Sensor Kinetic

The sensor kinetic is relatively fast. The closing kinetic of the sensor (SPR-Halo-p30-SNAP) observed by addition of NADP$^+$ (5 mM) without the presence of NADPH gave half-times ($t_{1/2}$) around 1 s (or less). However to measure the rate of opening, the sensor is first closed with low concentration of NADP$^+$ (20 μM) and an high concentration of NADPH (5 mM) is injected at the start of the measurement. The added NADPH competes with the cofactor binding site of SPR and open the sensor with half-times of around 5 s. We can conclude that the sensor should possess fast enough kinetic to follow the enzymatic activity measured in routine clinical tests (e.g. lactate dehydrogenase).

Different Sensors for FRET and BRET

As shown above, sensors comprising different FRET and BRET pairs can be produced. For NAD(P)H and NAD(H) sensor based on FRET, the FRET pairs can be composed by the following combinations: (i) a fluorescent protein and a self-labelling tag (e.g. SNAP-tag, CLIP-tag or Halo-tag) tethered with a synthetic molecule containing a fluorophore and the ligand (for example SPR-EGFP-p30-SNAP), (ii) two orthogonal self-labelling tags, one for the attachment of the synthetic molecule containing a fluorophore and the ligand, the other to attach a second fluorophore (for example SPR-Halo-p30-SNAP or SNAP-p30-CLIP-SPR), (iii) two fluorescent proteins; in that case the self-labelling tag is only used to attach the intramolecular ligand which does not contain a fluorophore (for example SPR-TagGFP2-p30-SNAP-TagRFP). It general, any method that permits site-specific labeling of proteins (unnatural amino acids, cysteine labeling, peptides labeled by enzymes) can be employed to construct suitable sensors. For the NAD(P)H and NAD(H) sensor based on BRET, the BRET pairs has to be composed of a luciferase and a fluorescent acceptor. Among others, the used luciferase can be firefly luciferase, *Renilla* luciferase, *Gaussia* luciferase or preferably NanoLuc™ (NLuc) luciferase, as this latter is brighter than other luciferases and has a greater signal half-life. The fluorescent acceptor can be a synthetic fluorophore or a fluorescent protein.

The criteria for choosing appropriate FRET or BRET pairs are the presence of a spectral overlap between the emission spectrum of the donor and the excitation spectrum of the acceptor and the good spectroscopic properties (e.g. brightness, photostability). For FRET, among others good FRET pairs are: tetramethylrhodamine derivatives (TMR)/silicon-rhodamine (SiR); carbopyronine derivatives (CPY)/SiR; Cy3/Cy5; fluorescein/TMR; Alexa488/TMR; Alexa488/Alexa546; Alexa488/Alexa594; ATTO488/ATTO565; ATTO565/ATTO647N; ATTO594/ATTO647N; EGFP/TMR; TagGFP2/TagRFP; mNeonGreen/mRuby2. Appropriate BRET fluorescent acceptor could be among others: Cy3, TMR, Alexa488, Alexa546, ATTO488, ATTO565.

Applications

A. Enzymatic Assays

The developed sensors for NADP(H) and NAD(H) can be use virtually in any enzymatic assays that follow generally the formation or consumption of NADPH or NADH by the absorbance at 340 nm to characterize the enzyme activity. This could not only be useful for the applications in the research field (e.g. the characterization directly or indirectly of numerous enzymes activity) but also in routine clinical tests, where the activity of diverse enzymes, metabolites or other molecules are measured for diagnostic purposes. As example, the following enzyme activity assay, measuring concentration changes of NADPH or NADH by absorbance, are routinely performed in serum or other body fluids in clinical labs: lactate dehydrogenase LDH (liver function, carcinoma, myocardial infarction, meningitis/encephalitis, acute pancreatitis), creatine kinase CK (muscle inflammation, Rhabdomyolysis, heart attack), fraction MB of the creatine kinase CK-MB (heart attack), aspartate aminotransferase AST (liver disorder), alanine aminotransferase ALT (liver disorder) glucose-6-phosphate dehydrogenase (drug-induced hemolytic anemia, megaloblastic anemia). The following molecules are also routinely measured in serum or other body fluids (urine and LCR) by enzymatic coupled assays relying on NADPH or NADH absorbance in clinical labs: glucose (diabetis), urea (kidney disease or disorder), ammonia (liver disorder, Reye's syndrome, hepatic encephalopathy), ethanol (ethanol intoxication or poisoning).

B. High-Throughput Screening

The developed sensors have sufficient sensitivity, reliability and stability to be used in high-throughput screening that would measure $NADP^+$, NADPH, $NAD^+$, NADH or their ratios. Samples could generally come from cell lysates, serum or other body fluids. As example, the sensors could be used for the high-throughput screening of large library of compounds in order to find therapeutics that are known to modulate NADP(H) or NAD(H) in cells. Targeting the NAD metabolism with therapeutic drugs has been recently considered as new strategy for cancer treatment. It is known that a decrease availability of $NAD^+$ caused by an inhibition of its synthesis will hinder the activities of $NAD^+$-dependent signaling pathways (e.g. DNA repair) and would additionally exhaust the energetic resources for proliferation. This is why the development and use of specific inhibitors of enzymes (like the nicotinamide phosphoribosyltransferase and mononucleotide adenylyltransferases) involved in the biosynthesis of $NAD^+$ are under scrutiny to evaluate their potential in cancer therapy (Chiarugi et al. Nat Rev Cancer. 2012 Nov.; 12(11):741-52). In another example, the sensors could be used in high-throughput screening for the validation of the toxicity profile of therapeutic drugs. Therapeutic drugs altering significantly the levels of NAD(H) or NADP (H), as side-effects, may possess severe cytotoxicity.

C. Live Cell Measurements

Another interesting feature of these sensors is that the different synthetic molecules are cell permeable, thereby allowing the use of NADP/NAD-sensors in (isoalated) living cells. Following cell transfection with the appropriate vector, the fusion protein construct (e.g. SPR-EGFP-p30-SNAP, SPR-Halo-p30-SNAP or SPR-TagGFP2-p30-SNAP-TagRFP) can be expressed in common cell culture (e.g. HEK293, U2OS). Simple addition of the synthetic molecules in the culture medium allows the intracellular labelling of the fusion protein forming the active sensor.

Figure 6A:
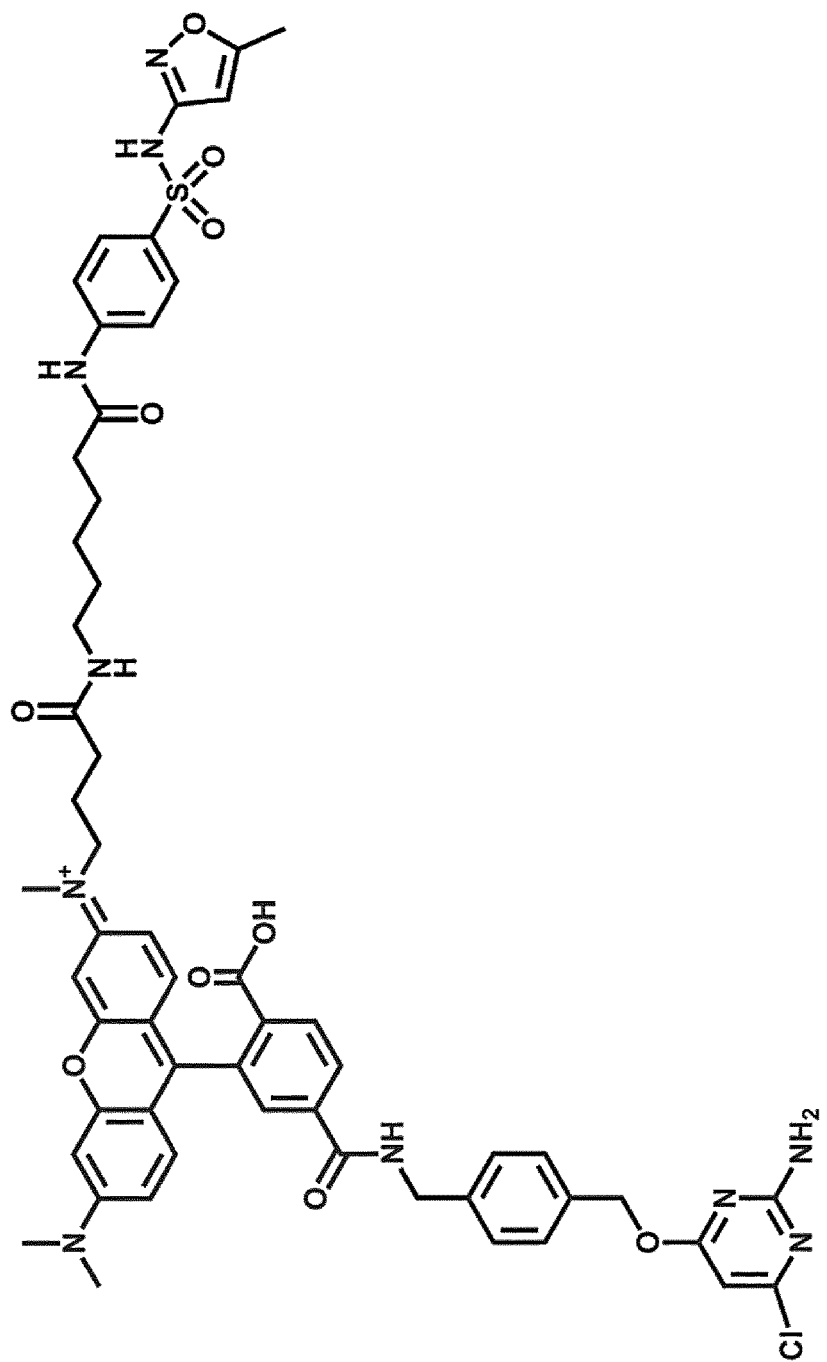
Figure 6B:
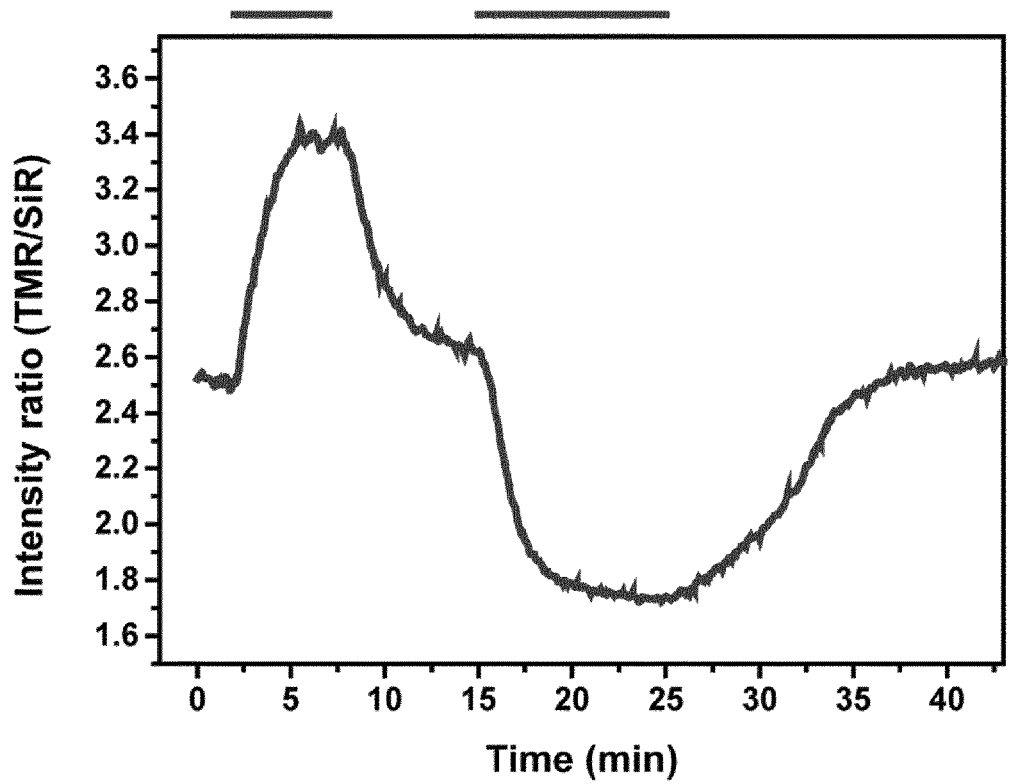

The ratio of TMR/SiR can then be measured using a widefield fluorescence microscope, confocal fluorescence microscope or a FLIM system with appropriate excitation and emission filters for TMR and SiR. As example, several experiments were performed, where the perfusion of reagents (e.g. $H_2O_2$) were added to alter the interacellular ratio of $NADPH/NADP^+$, and when the compound is removed and washed out, the cells recovered their basal level of $NADPH/NADP^+$ (FIG. 6B).

The changes relative to cofactor ratios can be measured in real time. In addition, by adding the appropriate localization sequence to the construct, the fusion protein can be targeted to different subcellular compartments like mitochondria, nucleus, endoplasmic reticulum to measure in living cells their specific ratio of $NADPH/NADP^+$ and $NADH/NAD^+$.

Kits

The sensors are advantageously provided as a commercial kit for in vitro applications. Exemplary kits may contain the following: the sensor molecule lyophilized or dissolved in a buffer and the appropriate standards for the quantification of ratios i.e. different ratios of $NAD(P)/NAD(P)^+$ and/or solution with $NADP^+$ or $NAD^+$. For live cell applications, the kit preferably also contains the appropriate plasmids for mammalian expression (for transient and/or stable transfection), the chosen subcellular localization (cytosol, mitochondria, nucleus, endoplasmic reticulum) and/or the different synthetic molecules for the intracellular labelling. Different cell-permeable synthetic molecules can be provided depending of the different FRET pairs desired.

LEGEND TO THE FIGURES

FIG. 1. (A) Schematic description of the structure and sensing mechanism of a NADP-specific FRET sensor based on the human sepiapterin reductase as binding protein. (B) Chemical structure of the synthetic molecule BG-TMR-C6-SPY (1) and BG-TMR-C6-SMX (2) (SPY: sulfapyridine; SMX: sulfamethoxazole) used for the SNAP-tag labelling. The $O^6$-benzylguanine moiety for the SNAP-tag, the tetramethylrhodamine fluorophore and SPR ligands are depicted in green, red and blue, respectively. (C) Response curve of the sensor (SNAP-p30-EGFP-SPR labelled with BG-TMR-C6-SMX) titrated with $NADP^+$. The FRET ratio change of this sensor is 1.8-fold between its closed and open state. (D) Response curves of the sensor (SNAP-p30-EGFP-SPR labelled with BG-TMR-C6-SPY) titrated with ratios of $NADPH/NADP^+$. The results show pH sensitive responses. (E) Response curves of the sensor (SNAP-p30-EGFP-SPR labelled with BG-TMR-C6-SMX) titrated with ratios of $NADPH/NADP^+$. Using sulfamethoxazole as intramolecular ligand produces a sensor insensitive to pH changes.

FIG. 2. (A) Response curves of the sensor (SPR-EGFP-p30-SNAP labelled with BG-TMR-C6-SMX) titrated first with $NADP^+$, then $NADP^+$ is enzymatically converted to NADPH and as shown by the observed ratio, the ligand is not able to bind in presence of NADPH, but only with $NADP^+$. The FRET ratio change of this sensor is 2.8-fold between its closed and open state. (B) Response curve of the sensor (SPR-EGFP-p30-SNAP) labeled with BG-TMR-C6-SMX titrated with sulfamethoxazole in presence of 10 µM $NADP^+$. (C) Response curves of the sensor titrated with $NADP^+$ and $NAD^+$, showing the high specificity of the sensor for $NADP^+$ compared to $NAD^+$. (D) Titrations of the sensor with different structurally close nucleotides (NADH, ATP, ADP, GTP), confirming the high specificity of the sensor.

FIG. 3. (A) Schematic description of the structure of an optimized version of the NADP-specific FRET-based sensor (SPR-Halo-p30-SNAP). By attaching the sepiapterin reductase by its C-terminus, which is in close proximity to the ligand binding site, to Halo-tag having its binding site close to its N-terminus, the two FRET pairs will be in close proximity in the closing state. In addition, a more red-shifted FRET pairs can be used increasing the reliability of the sensor in light-absorbing samples. (B) Structure of SiR-Halo, containing the chloroalkane moiety reacting specifically with Halo-tag. (C) Response curve of SPR-Halo-p30-SNAP (labelled with BG-TMR-C6-SMX and SiR-Halo) titrated with $NADP^+$. The FRET ratio change of this sensor is 8.0-fold between its closed and open state, which is significantly higher that the previous versions. (D) Emission spectrum changes of the sensor during the titration.

FIG. 4. Response curves of the NAD-specific sensor (SPR(D41W42)-Halo-p30-SNAP labelled with BG-TMR-C6-SMX), using an engineered SPR mutant developed by site-directed mutagenesis. As it can be observed, there is a complete switch of the natural specificity of SPR with measured apparent $K_d$ of 73 µM. Very high concentration of $NADP^+$ (10 mM) are necessary to even start closing the sensor.

Figure 5A:
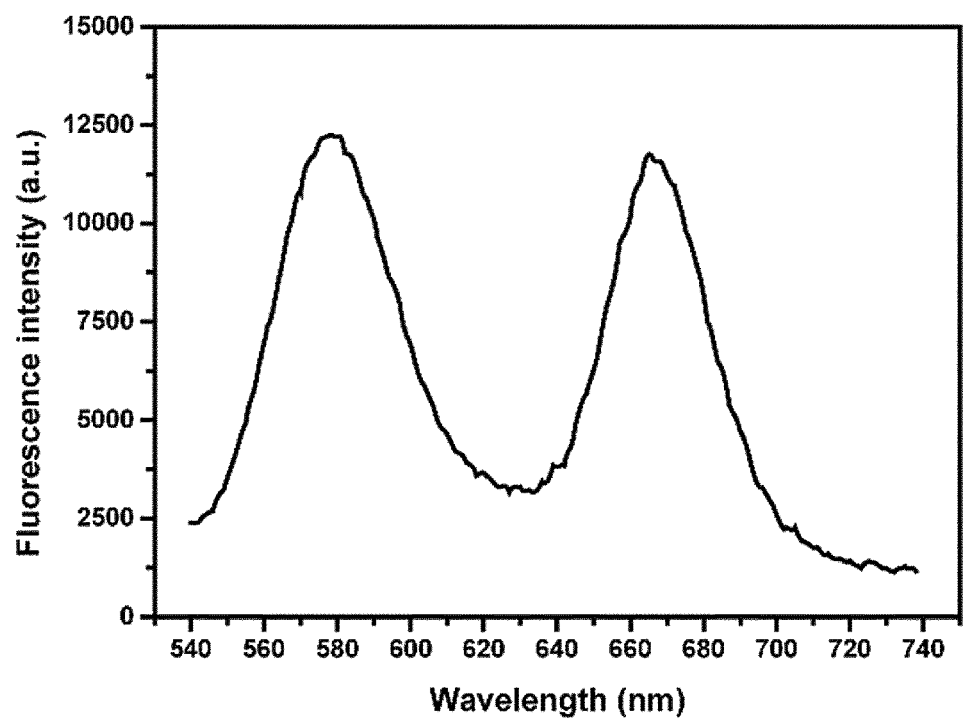
Figure 5B:
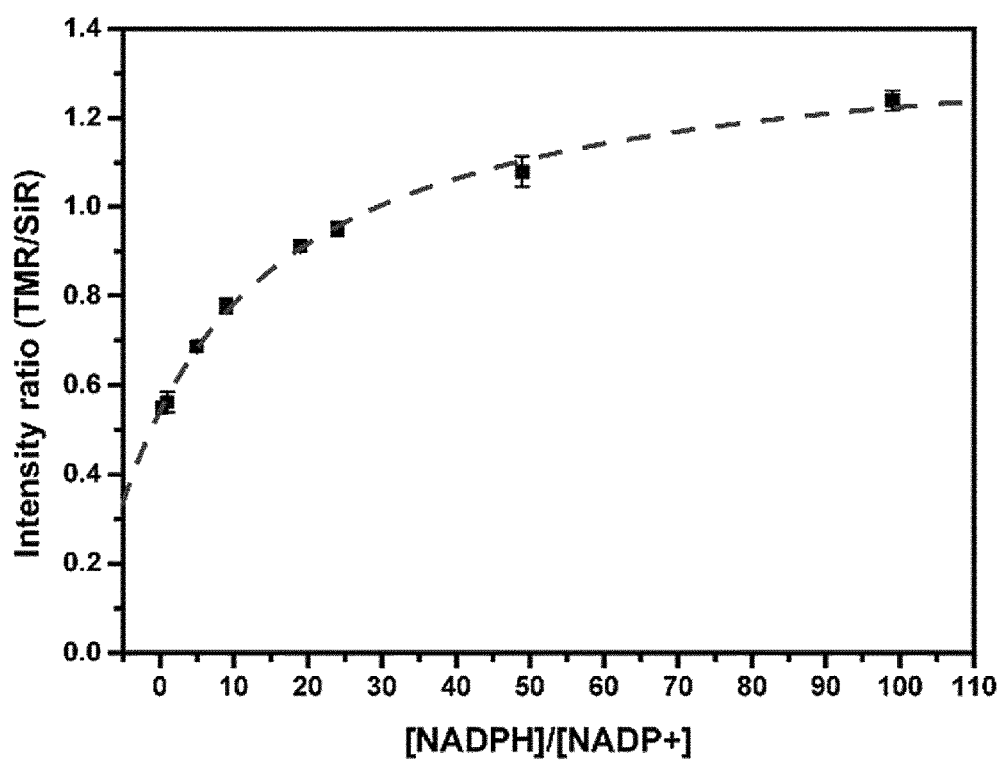

FIG. 5. (A) Emission spectrum measured for SPR-Halo-p30-SNAP (labelled with BG-TMR-C6-SMX) in concentrated HEK293 lysate. The measured ratio TMR/SiR is of 1.06. (B) Calibration curve produce by titrating the sensor in buffer with defined ratios of $NADPH/NADP^+$. The total cofactor concentration is kept at 100 µM. Correlating these data with the measurement in lysate, we can calculate that the free ratio of $NADPH/NADP^+$ in the lysate is around 40.

Figure 6C:
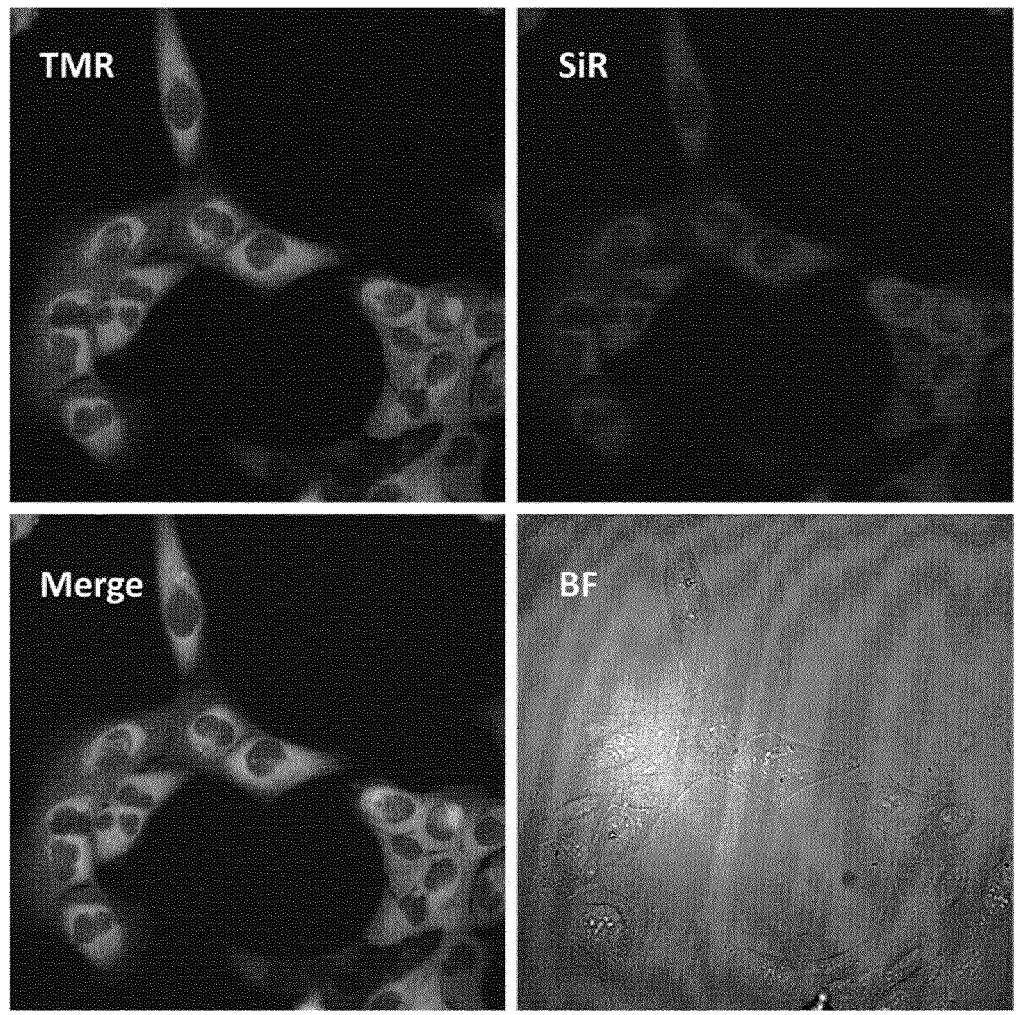

FIG. 6. (A) Structure of the synthetic molecule (CP-TMR-C6-SMX) used for the labelling of SNAP-tag in living cells. The $O^4$-benzyl-2-chloro-6-aminopyrimidine (CP) moiety for the SNAP-tag, the tetramethylrhodamine fluorophore and sulfamethoxazole as SPR ligand are depicted in green, red and blue, respectively. (B) Time-resolved trace of a perfusion experiment done on living U2OS cells after the labelling of the sensor (SPR-Halo-p30-SNAP labelled with CP-TMR-C6-SMX) expressed in the cytosol. A t=2 min, 2 mM sulfapyridine are perfused on the cells placed in a flow chamber. The sulfapyridine can compete directly with the intramolecular sulfamethoxazole. As result, it will open the sensor as observed in the increased ratio TMR/SiR. At t=7 min, HBSS is perfused to wash out the added sulfapyridine, as result the sensor returns to its basal level. At t=15 min, 100 µM $H_2O_2$ are perfused which significantly increase the oxidative stress of the cells and depletes their NADPH, the closing of the sensor is then correlated with a decreased $NADPH/NADP^+$ ratio. At t=25 min, only HBSS is perfused and the cells recover their basal $NADPH/NADP^+$ levels (the perfusion events and their length are indicated with red bars). (C) Images of the U2OS cells that were used for the perfusion experiment. The different images shown are: TMR (TMR excitation/emission filter), FRET (TMR excitation, Cy5 emission filter), a merge of the TMR and FRET channels and BF (transmission channel). The sensor has a proper cytosolic localization. For the time-course experiments, only the TMR and FRET channels are monitored in order to have faster time points and to avoid photobleaching.

FIG. 7. (A) Schematic description of the structure of a NADP-specific FRET sensor based on two fluorescent proteins (SPR-TagGFP2-p30-SNAP-TagRFP); FP1: TagGFP2, FP2: TagRFP. (B) Chemical structure of the synthetic molecule BG-Suc-C6-SMX (SMX: sulfamethoxazole, Suc: succinic acid linker) used for SNAP-tag labelling. The $O^6$-benzylguanine moiety for the SNAP-tag and the SPR ligand are depicted in green and blue, respectively. (C) Response curve of the sensor (SPR-TagGFP2-p30-SNAP-TagRFP labelled with BG-Suc-C6-SMX) titrated with $NADP^+$. The FRET ratio change of this sensor is 1.5-fold between its closed and open state.

FIG. 8. (A) Schematic drawing of the exemplary SPR-L molecule BG-Peg11-Cy3-sulfamethoxazole (B) Response curve of the NAD-specific sensor SNAP_P30_hSPR (D41W42)_NLuc_cpDHFR labelled with BG-Peg11-Cy3-sulfamethoxazole. The measured apparent $K_d$ of $NAD^+$ is 19 µM. (C) The sensor ratio change over time measured in the assay for lactate dehydrogenase activity. (D) LDH level measured by the sensor plot against the result obtained by the absorbance assay.

EXPERIMENTAL SECTION

The examples below described the design and construction of different SPR-based sensors for NADP(H) and NAD(H).

All chemical reagents and dry solvents for synthesis were purchased from commercial suppliers (Sigma-Aldrich, Fluka, Acros, Calbiochem) and were used without further purification or distillation. Peptide couplings were performed by activation of the respective carboxylic acid with N,N,N',N'-Tetramethyl-O-(N-succinimidyl)uronium tetrafluoroborate (TSTU) or N,N,N',N'-Tetramethyl-O-(1H-benzotriazol-1-yl)uronium hexafluorophosphate (HBTU) in the presence of N,N-diisopropylethylamine (DIPEA) as base in anhydrous dimethylsulfoxide (DMSO) at room temperature. Preparative HPLC was performed on a Waters 600 controller and with a Waters 2487 dual absorption detector using a SunFire™ Prep C18 OBD™ 5 µm 19×150 mm Column.

Example 1: SNAP-p30-EGFP-SPR

This example describes the design and construction of the initial FRET-based sensor capable of sensing the concentration of NADP(H). The sensor comprises the human sepiapterin reductase (SPR) as NADP(H)-specific binding protein and sulfapyridine or sulfamethoxazole as intramolecular ligand. EGFP and TMR form respectively the FRET donor and acceptor (FIG. 1A,B).

A synthetic molecule containing an $O^6$-benzylguanine (BG) moiety for the specific labelling of SNAP-tag, the flurophore tetramethylrhodamine (TMR) and sulfapyridine (SPY) as intramolecular SPR ligand was synthesized according to Scheme 1.

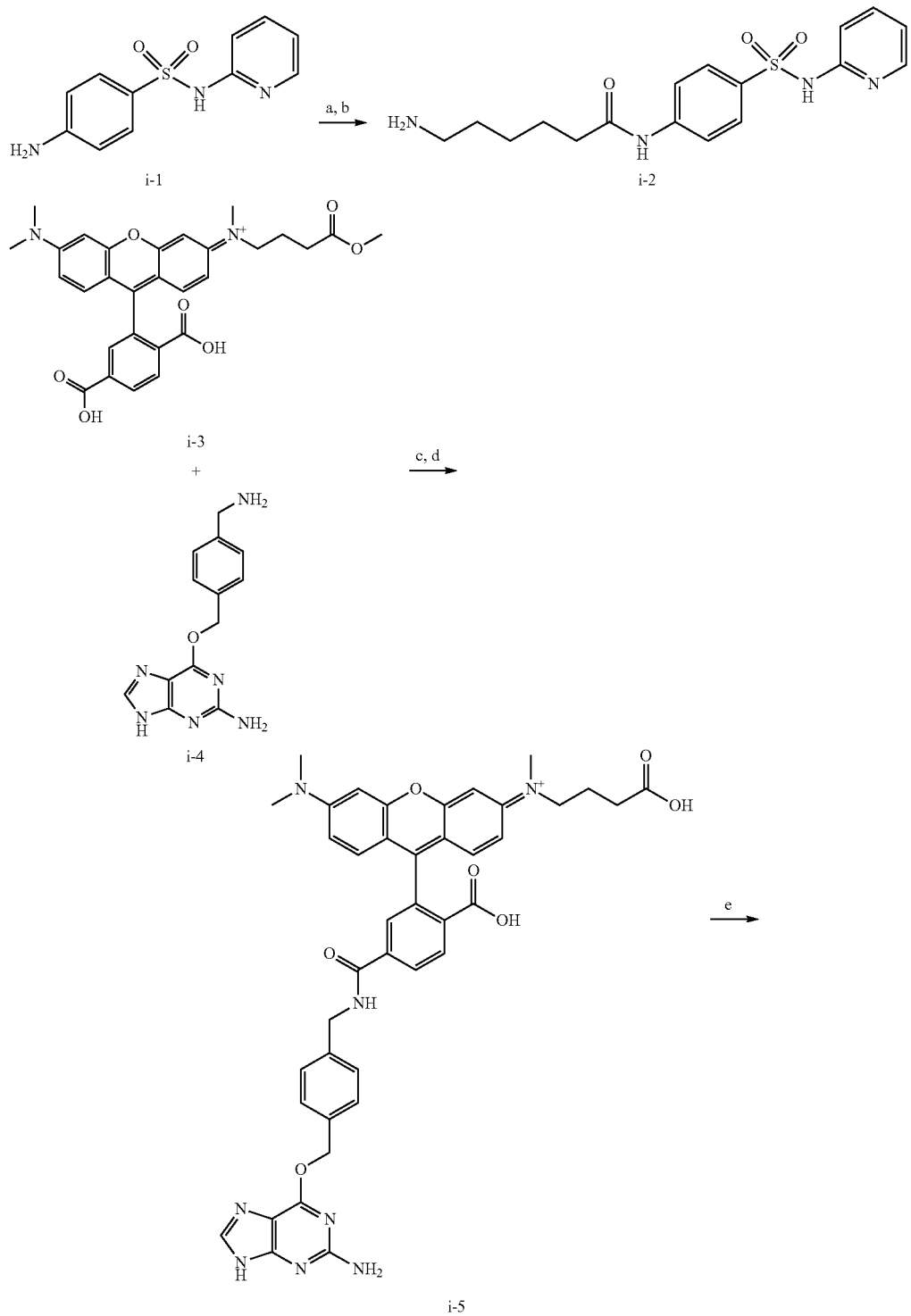

Scheme 1 | Schematic representation of the synthesis of BG-TMR-C6-SPY.

-continued

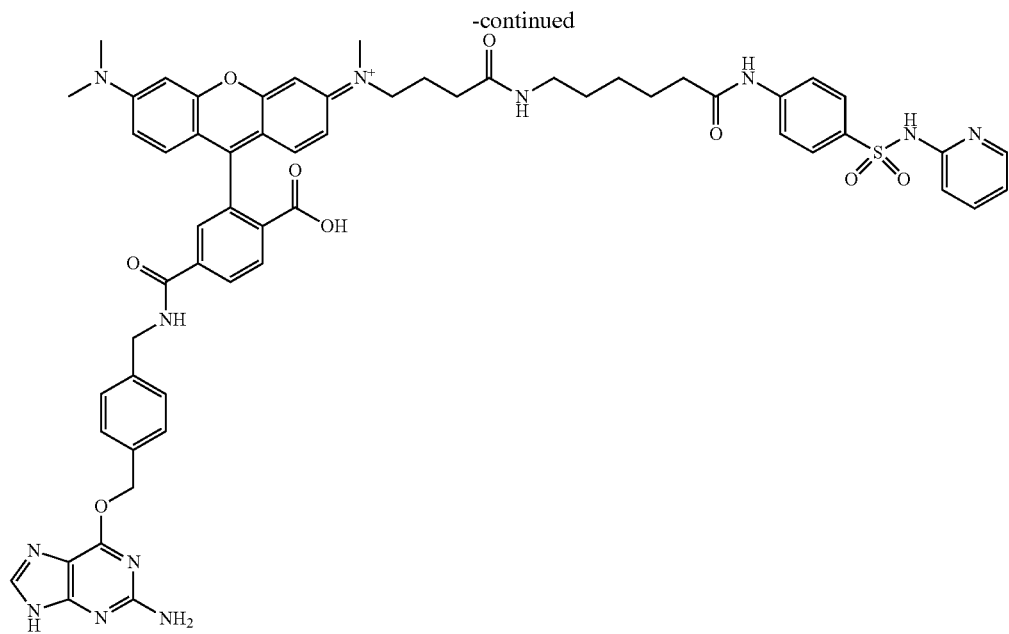

i-6

Reactions and conditions: (a) HBTU, DIPEA, DMSO, rt., 2 h; (b) 20% piperidine, ACN, rt., 1 h; (c) HBTU, DIPEA, DMSO, rt., 15 min; (d) 0.5M NaOH aq., rt., 15 min; (e) TSTU, DIPEA, DMSO, rt., 1 h.

6-amino-N-[4-(pyridin-2-ylsulfamoyl)phenyl] hexanamide (i-2)

To a solution of Fmoc-6-aminohexanoic acid (100 mg, 0.28 mmol, 1 eq.) in dry DMSO (1.0 mL, 280 mM), DIPEA (52 µL, 0.31 mmol, 1.1 eq.) and sulfapyridine (i-1) (200 mg, 0.8 mmol, 2.9 eq.) were added. HBTU (130 mg, 0.34 mmol, 1.2 eq.) was added to the reaction mixture and stirred for 2 h at RT. Then, 200 µL H$_2$O was added to the reaction mixture and stirred for 30 min. Finally, the reaction was quenched with 80 µL AcOH, purified by HPLC and lyophilized to yield a white solid (64.6 mg, 39%).

The fmoc-protected product was dissolved in 1 mL of a solution mixture of piperidine 20% in acetonitrile. The reaction mixture was stirred 1 h at RT, quenched with 0.2 mL AcOH, evaporated under reduced pressure, purified by preparative HPLC and lyophilized to yield a white solid (39.8 mg, quant.). TMR(6)-COOMe (i-3) was synthesized accordingly to the previously described procedure (Masharina et al., J Am Chem Soc. 2012 Nov. 21; 134(46):19026-34). BG-NH$_2$ (i-4) was synthesized accordingly to the previously described procedure (Keppler et al Nat Biotechnol. 2003 Jan.; 21(1):86-9.).

BG-TMR(6)-COOH (i-5)

To a solution of TMR(6-isomer)-COOMe (i-3) (6.1 mg, 11.8 µmol, 1 eq.) in dry DMSO (200 µL), DIPEA (20 µL, 115 µmol, 10 eq.) and HBTU (5.2 mg, 13.6 µmol, 1.15 eq.) were added. After 5 min, BG-NH$_2$ (i-4) was added to the reaction mixture. The reaction was stirred 15 min at RT. Then, 200 µL 1M NaOH was added and the reaction was stirred for another 15 min. 50 µL AcOH were added and the reaction was purified by HPLC and lyophilized to yield a red solid (4 mg, 45%).

BG-TMR-C6-SPY (i-6)

To a solution of BG-TMR(6)-COOH 1 eq. in dry DMSO, 10 eq. DIPEA and 1.2 eq. TSTU were added successively. The activation was checked by TLC (80/20 v/v ACN/H$_2$O). After ~5 min activation, i-2 was added and the reaction was allowed to stir for 1 h at RT. The reaction mixture were treated with H$_2$O (100 µL) and stirred for another 20 min to hydrolyze the remaining NHS ester. Then, the reaction was quenched with AcOH, purified by HPLC and lyophilized to yield a red solid.

A synthetic molecule containing an O$^6$-benzylguanine (BG) moiety for the specific labelling of SNAP-tag, the flurophore tetramethylrhodamine (TMR) and sulfamethoxazole (SMX) as intramolecular SPR ligand was synthesized according to Scheme 2.

Scheme 2 | Schematic representation of the synthesis of BG-TMR-C6-SMX.

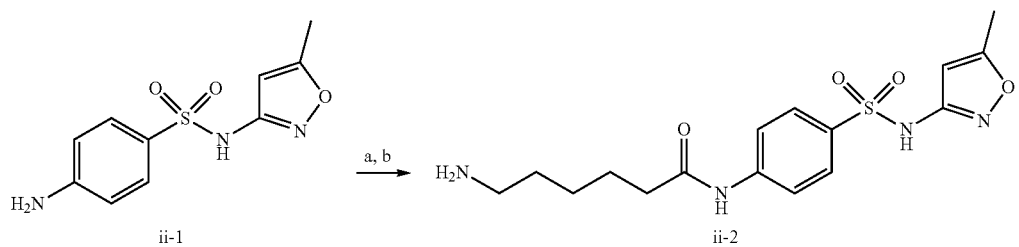

-continued
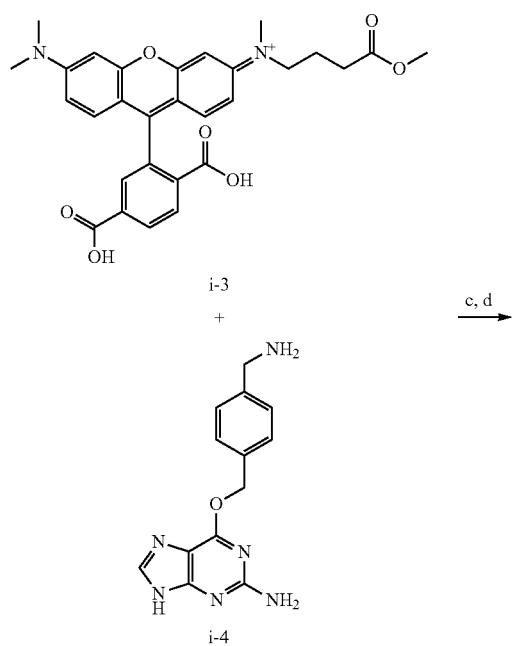
i-3
+
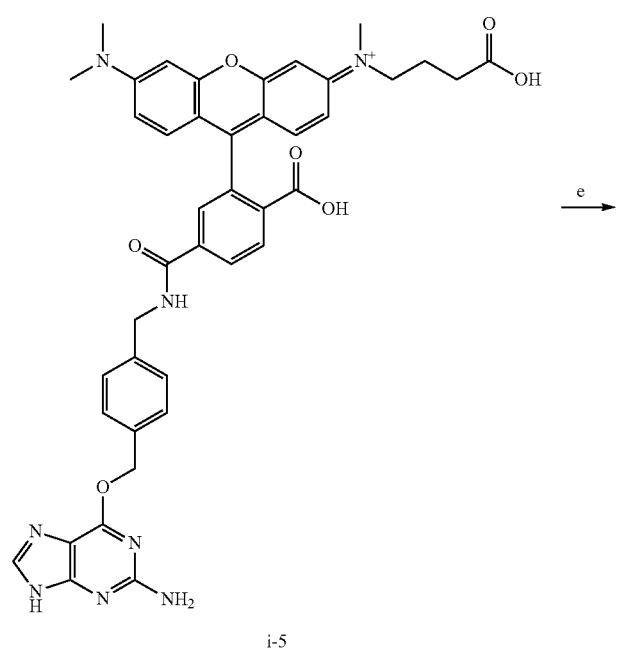
i-5

-continued

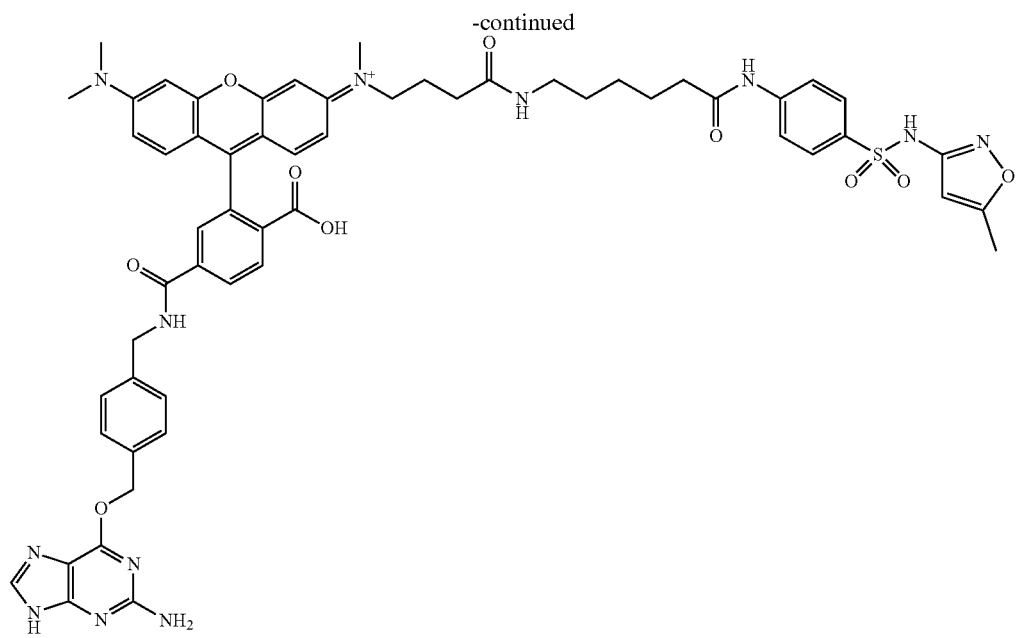

ii-6

Reactions and conditions: (a) HBTU, DIPEA, DMSO, rt., 2 h; (b) 20% piperidine, ACN, rt., 1 h; (c) HBTU, DIPEA, DMSO, rt., 15 min; (d) 0.5M NaOH aq., rt., 15 min; (e) TSTU, DIPEA, DMSO, rt., 1 h.

The synthesis of i-8, i-4 and i-5 is already described in the aforementioned example.

6-amino-N-{4-[(5-methyl-1,2-oxazol-3-yl)sulfamoyl]phenyl}hexanamide (ii-2)

To a solution of Fmoc-6-aminohexanoic acid (100 mg, 0.28 mmol, 1 eq.) in dry DMSO (1.0 mL, 280 mM), DIPEA (52 µL, 0.31 mmol, 1.1 eq.) and sulfamethoxazole (215 mg, 0.85 mmol, 3 eq.) were added. HBTU (130 mg, 0.34 mmol, 1.2 eq.) was added and the reaction was stirred 2 h at RT. Then, 200 µL $H_2O$ was added to the reaction mixture and stirred for 30 min. Finally, the reaction was quenched with 80 µL AcOH, purified by HPLC, lyophilized to yield a white solid (54 mg, 33%).

The fmoc-protected product was dissolved in 1 mL of a solution mixture of piperidine 20% in acetonitrile. The reaction mixture was stirred 1 h at RT, quenched with 0.2 mL AcOH, evaporated under reduced pressure, purified by preparative HPLC and lyophilized to yield a white solid (33.5 mg, quant.).

BG-TMR-C6-SMX (ii-6)

To a solution of BG-TMR(6)-COOH (220 µL, 0.58 µmol, 1 eq.) in dry DMSO (2.9 mM), DIPEA (4 µL, 12 µmol, 41 eq.) and TSTU (7 µL, 0.7 µmol, 1.2 eq.) were added successively. The activation was checked by TLC (80/20 v/v ACN/$H_2O$). After ~5 min activation, ii-2 (34 µL, 2.32 µmol, 4 eq.) was added and the reaction was allowed to stir for 1 h at RT. The reaction mixture were treated with $H_2O$ (100 µL) and stirred for another 20 min to hydrolyze the NHS ester. Then, the reaction was quenched by the addition of 20 µL of AcOH, purified by HPLC and lyophilized to yield a red solid (0.4 µmol, 70%).

The fusion protein comprising of SNAP-tag, a 30-proline linker, EGFP and sepiaterin reductase (SPR), was constructed by first replacing the coding sequence of HCA in the previously described sensor SNAP-p30-CLIP-HCA (Brun et al. J Am Chem Soc. 2011; 133(40): 16235-42) by the coding sequence of SPR using standard cloning techniques yielding SNAP-p30-CLIP-SPR. In a second cloning step, the CLIP-tag was replaced by the coding sequence of EGFP using standard cloning techniques yielding SNAP-p30-EGFP-SPR. The fusion protein was expressed in the E. coli strain Rosetta-Gami™ 2 (DE3)pLysS (Novagen, Merck KGaA, Darmstadt, Germany) and purified using a C-terminal His-tag as well as an N-terminal Strep-tag II to obtain the full construct.

The purified fusion protein SNAP-p30-EGFP-SPR (5 µM) was labelled with 2 eq. of BG-TMR-C6-SPY or BG-TMR-C6-SMX (10 µM) in a buffer (50 mM HEPES, 150 mM NaCl, pH 7.5) for 1 h at room temperature. After the incubation, the excess of ligand was removed by three washing steps (3×400 µL) with the aforementioned buffer using a centrifugal filter spin column with a 50 kDa cut-off membrane (Amicon Ultra-0.5 Centrifugal Filter, Merck KGaA, Darmstadt, Germany). The purified sensor is then diluted to a concentration of 5 µM in HEPES buffer (in 50 mM HEPES, 150 mM NaCl, pH 7.5).

To evaluate the performance of the sensor, titrations experiments were performed with different concentrations of $NADP^+$. The labelled sensor was diluted to a concentration of 50 nM in 100 µL of HEPES buffer (50 mM HEPES, 150 mM NaCl, 0.5 mg/mL BSA, pH 7.5) containing defined concentrations of $NADP^+$ and NADPH in black non-binding 96-well plates (Greiner Bio-One, Kremsmünster, Austria).

The solutions were incubated at room temperature for at least 15 minutes to ensure that the sensor had reached equilibrium. Fluorescence measurements were done on an Infinite M1000 spectrofluorometer (TECAN). Excitation was carried out at 450 nm with a bandwidth of 10 nm and spectra were recorded from 480 to 610 nm using a step size of 1 nm and bandwidths of 10 nm.

As shown in FIG. 1C, the sensor is able to monitor changes in the $NADP^+$ concentration with an overall FRET ratio change of 1.8 between a closed conformation (low $NADP^+$ concentration) and an open conformation (high $NADP^+$ concentration). In addition, the measured apparent $K_d$ of the sensor is 33 f 6 nM in presence of $NADP^+$. In fact, the affinity is so strong that we directly measure the sensor concentration (~50 nM). Therefore, such a sensor would be more useful in directly measuring ratio of cofactors rather than only $NADP^+$.

Another titration was performed using the aforementioned procedure, where the labelled sensor was diluted in buffer containing different ratio of $NADPH/NADP^+$ with a fixed total concentration of cofactors (100 µM) and a fixed concentration of N-acetylserotonin as competitive SPR ligand to tune the sensor response. We observed that the sensor can be efficiently use to measure ratio of $NADPH/NADP^+$ but when labelled with sulfapyridine as intramolecular ligand, the sensor is sensitive to pH variations (FIG. 1D). Using the same fusion protein labelled with a sulfamethoxazole as intramolecular ligand, which has an appropriate pKa, allow us to resolve the pH-sensitivity (FIG. 1E).

Example 2: SPR-EGFP-p80-SNAP

This example describes an alternative optimized geometry of the previously described FRET sensor.

As before, the sensor contains the same FRET pair (EGFP and TMR). SNAP-tag is labelled with the synthetic molecule BG-TMR-C6-SMX previously described. The fusion protein comprising of SPR, EGFP, a 30-proline linker and SNAP-tag was constructed by first replacing the coding sequence of RLuc8 in a previous plasmid SPR-RLuc8-SNAP by the coding sequence of EGFP using standard cloning techniques yielding SPR-EGFP-SNAP. In a second cloning step, an annealed 30-proline oligonucleotides was inserted between EGFP and SNAP using standard cloning techniques yielding SPR-EGFP-p30-SNAP. The fusion protein was expressed in the *E. coli* strain Rosetta-Gami™ 2 (DE3)pLysS (Novagen, Merck KGaA, Darmstadt, Germany) and purified using a C-terminal His-tag as well as an N-terminal Strep-tag II to obtain the full construct.

The purified fusion protein SPR-EGFP-p30-SNAP (5 µM) was labelled with 2 eq. of BG-TMR-C6-SMX or BG-TMR-C6-SPY (10 µM) in a buffer (50 mM HEPES, 150 mM NaCl, pH 7.5) for 1 h at room temperature. After the incubation, the excess of ligand was removed by three washing steps (3×400 µL) with the aforementioned buffer using a centrifugal filter spin column with a 50 kDa cut-off membrane (Amicon Ultra-0.5 Centrifugal Filter, Merck KGaA, Darmstadt, Germany). The purified sensor is then diluted to a concentration of 5 µM in HEPES buffer (in 50 mM HEPES, 150 mM NaCl, pH 7.5).

To evaluate the performance of the sensor, titrations experiments were performed with different concentrations of $NADP^+$ and NADPH using the enzyme glucose-6-phosphate dehydrogenase (Baker yeast, type IX, Sigma) and its substrate glucose-6-phosphate to convert the $NADP^+$ measured in 96-well plate into NADPH. This enzyme cycling method was performed to assure that there is almost no remaining $NADP^+$ present in the solution but only NADPH. Indeed, it was found that the commercially available NADPH contains traces of $NADP^+$ up 2%. The labelled sensor was diluted to a concentration of 50 nM in 100 µL of HEPES buffer (50 mM HEPES, 150 mM NaCl, 0.5 mg/mL BSA, pH 7.5 and 1 mM glucose-6-phosphate) containing defined concentrations of $NADP^+$ in black non-binding 96-well plates (Greiner Bio-One, Kremsmünster, Austria). The solutions were incubated at room temperature for at least 15 minutes to ensure that the sensor had reached equilibrium. Fluorescence measurements were done on an Infinite M1000 spectrofluorometer (TECAN). Excitation was carried out at 450 nm with a bandwidth of 10 nm and spectra were recorded from 480 to 610 nm using a step size of 1 nm and bandwidths of 10 nm. After this first measurement, 1 µL of glucose-6-phosphate dehydrogenase from baker's yeast (Type IX, Sigma) reaching a final concentration of 26 nM. The solutions were incubated for 1 h at room temperature to ensure the maximal conversion of $NADP^+$ into NADPH. The result shows clearly that the intramolecular ligand can only bind to SPR in presence of $NADP^+$ and not in presence of NADPH (FIG. 2A).

The slight decrease of the FRET ratio at the highest concentration of cofactor is due to the inhibition of the glucose-6-phosphate dehydrogenase by the high concentration of NADPH, which cannot reach complete conversion (FIG. 2C). Additionally, the titration curve showed that we were able to optimize the geometry of the sensor so that the FRET ratio improved from 1.8 for SNAP-p30-EGFP-SPR to 2.8 for SPR-EGFP-p30-SNAP.

Figure 2D:
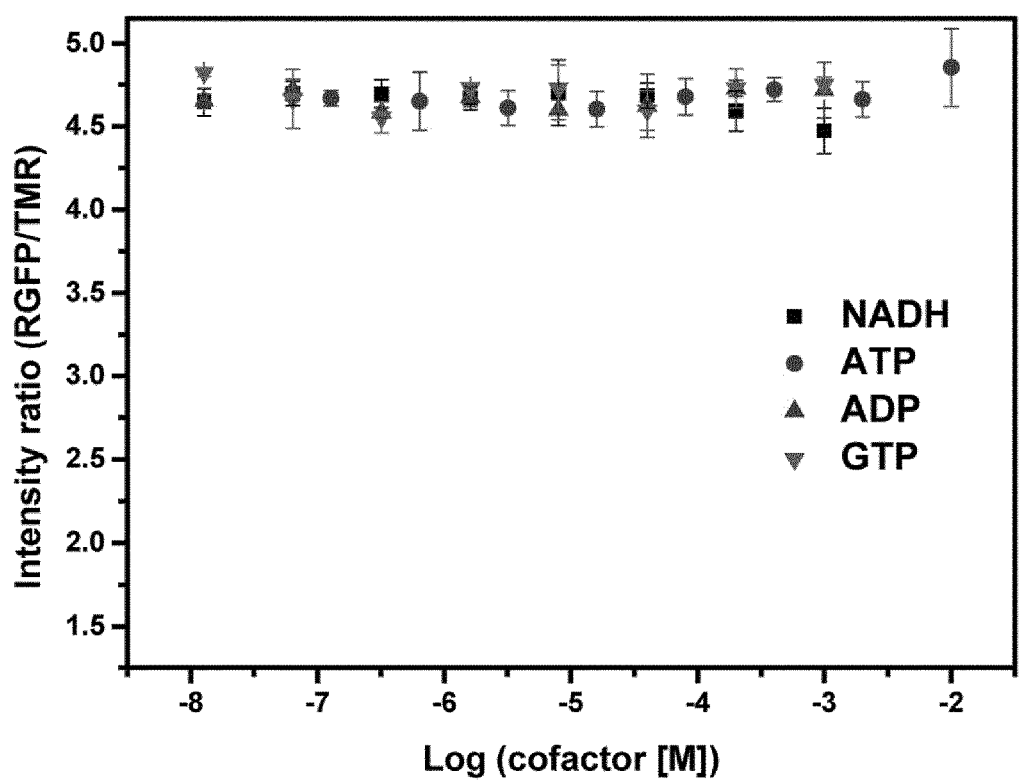

In another titration, the sensor's specificity was tested by diluting the labelled sensor to a concentration of 50 nM in 100 µL of HEPES buffer (50 mM HEPES, 150 mM NaCl, 0.5 mg/mL BSA, pH 7.5) containing defined concentration of different nucleotides structurally close to $NADP^+$: $NAD^+$, NADH, ATP, ADP, GTP (FIG. 2D). As it can be observed, the sensor is highly specific for $NADP^+$ and cannot close with other nucleotides. Only at the highest concentration of $NAD^+$, a slight closing of the sensor can be observed. However, these values are outside of the physiological range and due to the very high difference of affinity between $NADP^+$ and $NAD^+$ ($10^4$-fold difference), $NAD^+$ would not be able to compete with $NADP^+$.

Example 3: SPR-Halo-p30-SNAP

This example describes the design and construction of an optimized FRET-based sensor capable of sensing the concentration of NADP(H). The sensor comprises the human sepiapterin reductase (SPR) as NADP(H)-specific binding protein and sulfamethoxazole as intramolecular ligand. Halo-tag, another self-labelling tag, is used for the specific labelling of the fluorophore SiR (FIG. 3A). TMR and SiR form respectively the FRET donor and acceptor. SNAP-tag is labelled with the synthetic molecule BG-TMR-C6-SMX previously described (see FIG. 1B, Scheme 2).

Figure 3B:
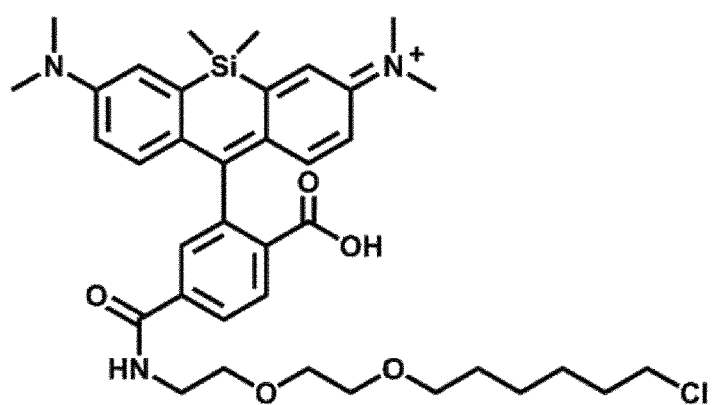
Figure 3C:
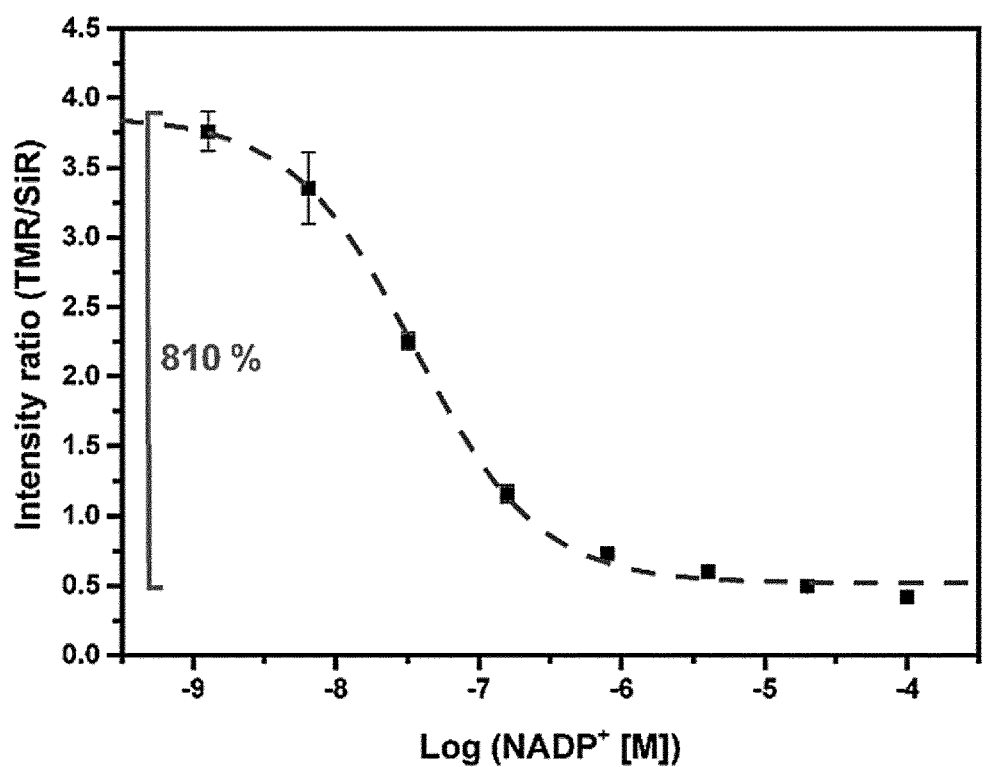
Figure 3D:
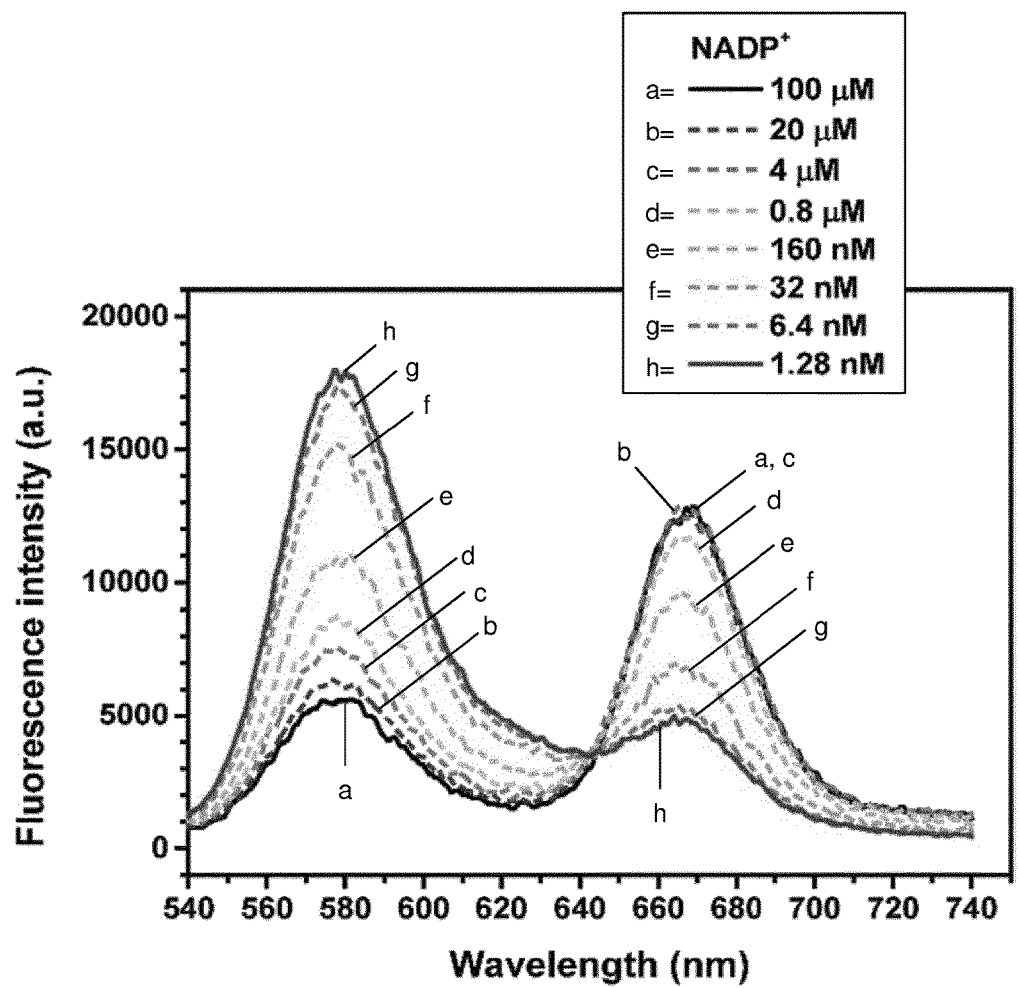

For the labelling of Halo-tag, a molecule containing a chloroalcane group linked to the fluorophore silicon-rhodamine was synthesized accordingly to the described procedure (Lukinavicius et al, Nat Chem. 2013 Feb.; 5(2):132-9) (FIG. 3B). The fusion protein comprising of SPR, Halo-tag, a 30-proline linker and SNAP-tag was constructed by replacing the coding sequence of EGFP in a previous construct SPR-EGFP-p30-SNAP by the coding sequence of Halo-tag (Promega, Fitchburg, Wis.) using standard cloning techniques yielding SPR-Halo-p30-SNAP. The fusion protein was expressed in the *E. coli* strain Rosetta-Gami™ 2 (DE3)pLysS (Novagen, Merck KGaA, Darmstadt, Germany) and purified using a C-terminal His-tag as well as an N-terminal Strep-tag II to obtain the full construct. The purified fusion protein SPR-Halo-p30-SNAP (5 µM) was labelled with 2 eq. of BG-TMR-C6-SMX (10 µM) in a buffer (50 mM HEPES, 150 mM NaCl, pH 7.5) for 1 h at room temperature. After the incubation, the excess of ligand was removed by three washing steps (3×400 µL) with the aforementioned buffer using a centrifugal filter spin column with a 50 kDa cut-off membrane (Amicon Ultra-0.5 Centrifugal Filter, Merck KGaA, Darmstadt, Germany). The purified sensor is then diluted to a concentration of 5 µM in HEPES buffer (in 50 mM HEPES pH, 150 mM NaCl, pH 7.5).

To evaluate the performance of the sensor, titrations experiments were performed with different concentrations of $NADP^+$. The labelled sensor was diluted to a concentration of 50 nM in 100 µL of HEPES buffer (50 mM HEPE, 150 mM NaCl, 0.5 mg/mL BSA, pH 7.5) containing defined concentrations of $NADP^+$ in black non-binding 96-well plates (Greiner Bio-One, Kremsmünster, Austria). The solutions were incubated at room temperature for at least 15 minutes to ensure that the sensor had reached equilibrium. Fluorescence measurements were done on an Infinite M1000 spectrofluorometer (TECAN). Excitation was carried out at 520 nm with a bandwidth of 10 nm and spectra were recorded from 540 to 740 nm using a step size of 1 nm and bandwidths of 10 nm. As seen in FIG. 3C,D, the FRET ratio change (8.0-fold) is significantly above the previous sensor versions. Furthermore, using a more red-shifted FRET pairs, this sensor has a higher sensitivity and therefore is more reliable in lysate or serum measurements (FIG. 5A,B).

Example 4: SPR(D41W42)-Halo-p30-SNAP

This example describes the design and construction of an optimized FRET-based sensor capable of sensing the concentration of NAD(H). The sensor comprises a mutant of SPR as NAD(H)-specific binding protein and sulfamethoxazole as SPR-L. Halo-tag, another self-labelling tag, is used for the specific labelling of the fluorophore SiR. TMR and SiR form respectively the FRET donor and acceptor pair. SNAP-tag is labelled with the synthetic molecule BG-TMR-C6-SMX previously described and SiR-Halo is used for the specific labelling of Halo-tag. The fusion protein comprising of a mutant of SPR(D41W42), Halo-tag, a 30-proline linker and SNAP-tag was constructed by using PCR site-directed mutagenesis using designed primers to performed several point mutations in order to change two bases; namely the following mutations A41D and R42W to yield SPR (D41W42)-Halo-p30-SNAP. The fusion protein was expressed in the *E. coli* strain Rosetta-Gami™ 2 (DE3) pLysS (Novagen, Merck KGaA, Darmstadt, Germany) and purified using a C-terminal His-tag as well as an N-terminal Strep-tag II to obtain the full construct.

The purified fusion protein SPR(D41W42)-Halo-p30-SNAP (5 µM) was labelled with 2 eq. of BG-TMR-C6-SMX (10 µM) in a buffer (50 mM HEPES, 150 mM NaCl, pH 7.5) for 1 h at room temperature. After the incubation, the excess of ligand was removed by three washing steps (3×400 µL) with the aforementioned buffer using centrifugal filter spin column with a 50 kDa cut-off membrane (Amicon Ultra-0.5 Centrifugal Filter, Merck KGaA, Darmstadt, Germany). The purified sensor is then diluted to a concentration of 5 µM in HEPES buffer (in 50 mM HEPES, 150 mM NaCl, pH 7.5).

In order to evaluate, that these mutations were sufficient to fully switch the specificity of the cofactor binding site of SPR from NADP(H) to NAD(H), we prepared titration experiments according to the similar procedure explained herein (example 3). The labelled sensor were diluted in buffer solution containing defined concentrations of $NAD^+$ and $NADP^+$ and measure with the fluorimeter (TECAN) (FIG. 4).

The titration curves revealed that SPR mutant has a complete reverse cofactor specificity as seen for the wild-type (see FIG. 4 by comparison with FIG. 2C representing the wild-type SPR). However, the apparent Kd of the sensor is 73-13 µM for $NAD^+$ showing a significant lower affinity compared to the initial SPR for $NADP^+$. Different strategies can be used to tune the sensor if necessary. For example, the cofactor binding site can be further engineered (mutated) to increase the affinity for $NAD^+$ while keeping the adequate specificity. As well, the ligand binding site of SPR can be mutated to increase its affinity for SPR while keeping the high specificity for one of the two redox state. An alternative approach is to use SPR inhibitors based on the sulfonamide scaffold that have higher affinity for SPR in presence of $NAD(P)^+$.

Example 5: Lysate Measurement

For the measurement in lysate, SPR-Halo-p30-SNAP was labelled with BG-TMR-C6-SMX and SiR-Halo as described in the example No. 3.

HEK293 cells in suspension were grown (37° C., 5% $CO_2$, 100 rpm) in 15 mL Ex-cell 293 medium supplemented by GlutaMax for 4 days reaching typically $2 \times 10^6$ cells/mL, $3 \times 10^7$ total cells with viability >97% (trypan blue test). The cells were pellet by centrifugation (5 min, 750 rpm, 4° C.), The supernatant was removed and the cells were resuspended in 1 mL cold PBS. The cells were lyzed by freeze-thaw cycle (2 min in $N_2$ liq., 2 min in a water bath at 37° C.) and shortly vortex. The cells debris were centrifuge at 13'000 rpm, 5 min, 4° C. and the supernatant was filtered through centrifugal filter spin column with a 10 kDa cut-off membrane (Amicon Ultra-0.5 Centrifugal Filter, Merck KGaA, Darmstadt, Germany). The labelled sensor was then diluted to 50 nM in 100 µL lysate and the ration was measured with a fluorimeter (TECAN) using the same parameter than described in the example 3. In parallel, a titration of the labelled sensor in solution containing defined ratio of NADPH/$NADP^+$ was performed as calibration (total cofactor concentration: 100 µM). Additionally, the lysate was also measured in a UV-Vis spectrophotometer to get a rough estimation of the concentration of [NADPH]+[NADH] giving an absorbance 1.1-1.7 at 340 nm (l=1 cm, ε=6'220 $M^{-1}$ $cm^{-1}$) correlated to a concentration of 180-270 µM. The lysate is therefore sufficiently concentrated for the sensor measurement to be reliable.

Comparing the results that we obtained with the lysate measurement (ratio TMR/SIR=1.06) with the calibration curve, we obtained a ratio of NADPH/$NADP^+$=40 (FIG. 5A,B). This value is in accordance with the reported ratio of free NADPH/$NADP^+$ of 26.8 to 57.8 relative to the concentration of glucose (3 mM to 20 mM) (Hedeskov et al., Biochem J. Jan. 1, 1987; 241(1): 161-167.).

Example 6: Live Cells Measurement

SPR-Halo-p30-SNAP was expressed in U2OS cells and labelled with CP-TMR-C6-SMX and SiR-Halo. CP-TMR-C6-SMX (FIG. 6A) was synthesized according to the same synthetic scheme as BG-TMR-C6-SMX, only starting with the $CP-NH_2$. The $O^4$-benzyl-2-chloro-6-aminopyrimidine (CP) is another specific reactive moiety for SNAP-tag labelling, which has been found to lead to more cell-permeable compounds. $CP-NH_2$ was synthesized accordingly to the previously described procedure (Srikun et al., J Am Chem Soc. 2010 Mar. 31; 132(12):4455-65).

Semi-stable U2OS (SPR-Halo-p30-SNAP cloned in a pEBTet vector; see Bach et al. FEBS J. 2007 Feb.; 274(3): 783-90 for the description of pEBTet) freshly trypsinated are diluted 5-fold with DMEM GlutaMax+10% FBS and 1

μg/mL puromycin. They are plated (2 mL) in previously sterilized and poly-L-ornithine coated (1 h incubation) glass coverslips (20×20 mm, VWR) in 12-well plate (TPP). On day 2, the expression is induced by 100 ng/mL doxycycline for ~24 h. On day 3, the cells are labelled with 1 μM CP-TMR-C6-SMX and 1 μM SiR-Halo with 10 μM (+/−)-verapamil overnight. On day 4, the cells are washed 3 times with DMEM GlutaMax+10% FBS without phenol red (10 min incubation, 37° C., 5% $CO_2$ between each step). After 30 min of incubation, the cells are ready for imaging.

Glass coverslips with labelled U2OS cells were transferred to a Cytoo chamber (44×34×10 mm). Gravity fed perfusion of the chamber was performed at a flow rate of 1 mL/min. Time-course experiments of sensor imaging were performed using a Leica LAS AF 7000 wide-field microscope equipped with a 63× plan Apochromat 1.40 NA oil immersion objective lens. A xenon arc lamp was used for imaging of the U2OS cells. For each frame, the two channels (donor and FRET) were measured consecutively with an interval of 10 s between the two emission channels. The filter set Cy3/Cy5 was used for FRET ratio imaging with excitation at 530/35 and emission at 580/40 (Cy3) as well as excitation at 635/30 and emission at 700/72 (Cy5). If not indicated otherwise, the image size was 194 μM×194 μM. The reagent perfused during the experiment ($H_2O_2$, SPY) were dissolved in HBSS (Lonza). HBSS solution was continuously perfused during the other time point of the experiment.

As a control for the sensor functionality, 2 mM of sulfapyridine (SPY) is perfused on the cells. The sulfapyridine, once entered in the cytosol, competes with the intramolecular ligand sulfamethoxazole and open the sensor. The concentration of sulfapyridine is sufficient to fully open the sensor and thus have a calibration point to quantify changes in NADPH/$NADP^+$. Then, the sulfapyridine is wash out by HBSS and we can observe that the intracellular sensor goes back to its initial ratio (TMR/SiR). Then, a solution of hydrogen peroxide was perfused and as result a sharp decrease of the ratio can be monitored. The addition of $H_2O_2$ caused an oxidative stress activating the cellular oxidative system. This system comprises the glutathione peroxidase, which oxidizes the glutathione to decompose the hydrogen peroxide. The oxidized pool of glutathione will then be reduced by the activity of the glutathione reductase depleting the NADPH, thus decreasing the ratio NADPH/$NADP^+$ and closing the sensor. Interestingly, we can observe that the cells are able to quickly return to their basal level of NADPH/$NADP^+$ once the addition of $H_2O_2$ is stopped and washed out.

It has to be noted that with the microscope, the purified sensor has a slightly reduced FRET ratio change between the open and closed conformation (ΔRmax=6). Due to the relatively high free ratio of NADPH/$NADP^+$ in living cells, the sensor cannot be seen in a fully closed conformation, explaining the smaller FRET ratio changes observed in live cells compared to the in vitro experiments.

To summarize, the sensor is very useful for live cell imaging. Especially, it can be used to quantity the different ratio NADPH/$NADP^+$ in the different subcellular compartments (cytosol, mitochondria, nucleus, reticulum endoplasmic).

Example 7: SPR-TagGFP2-p30-SNAP-TagRFP

Figure 7A:
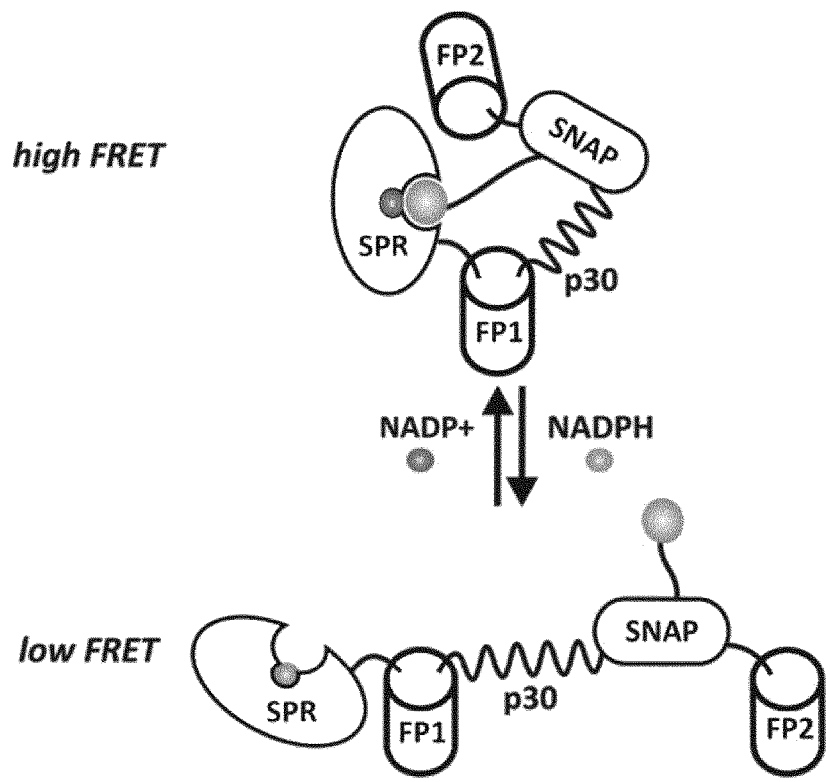
Figure 7B:
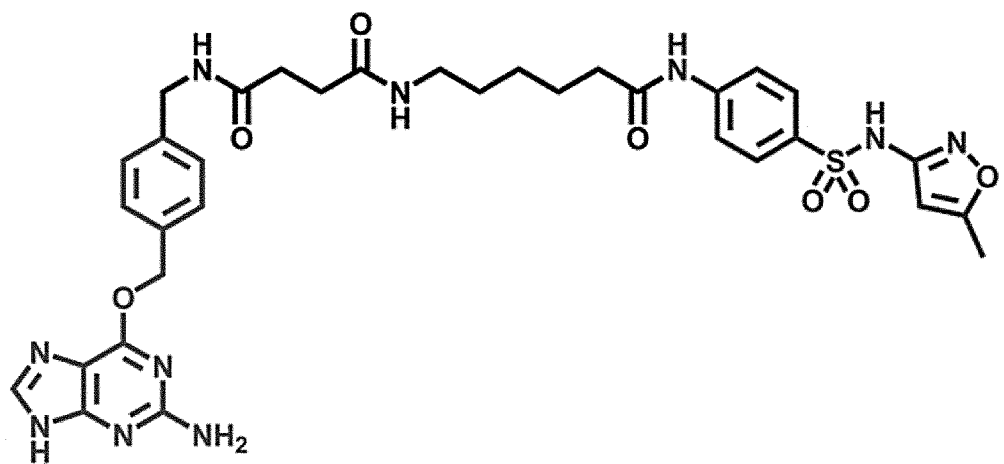

This example describes the design and construction of a FRET-based sensor using two fluorescent proteins capable of sensing the concentration of $NADP^+$ and ratio of NADPH/$NADP^+$. The sensor comprises the human SPR as NADP(H)-specific binding protein and sulfamethoxazole as intramolecular ligand. TagGFP2 and TagRFP form respectively the FRET donor and acceptor (FIG. 7A). A synthetic molecule containing an $O^6$-benzylguanine (BG) moiety for the specific labelling of SNAP-tag, an alkyl linker and sulfamethoxazole (SMX) as intramolecular SPR ligand was synthesized according to Scheme 3 (FIG. 7B).

Scheme 3 | Schematic representation of the synthesis of BG-Suc-C6-SMX (iii-2).

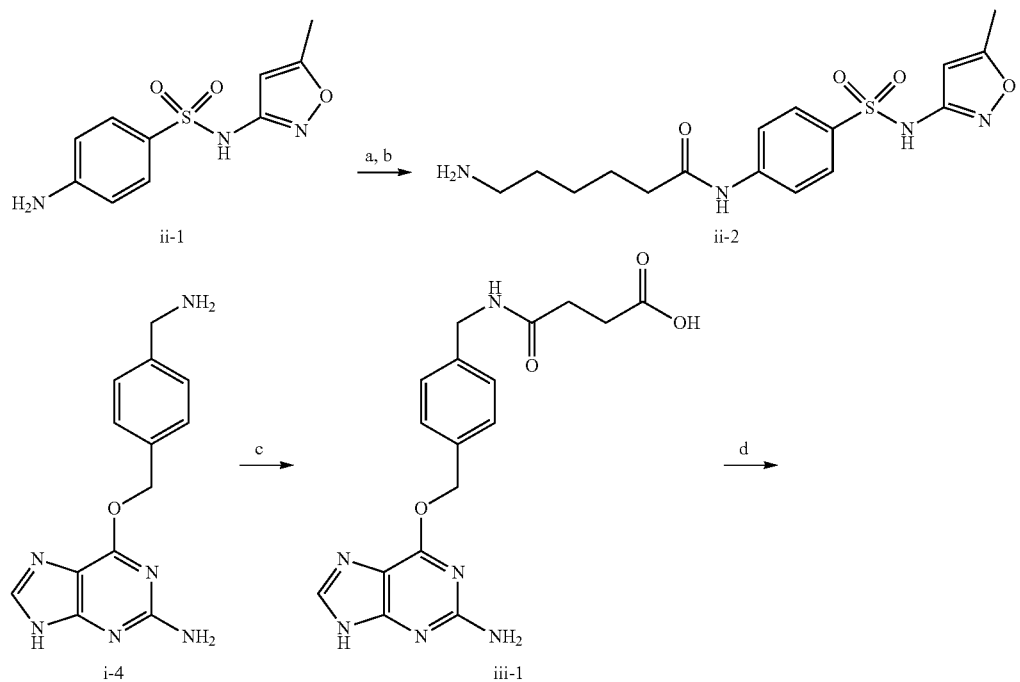

-continued

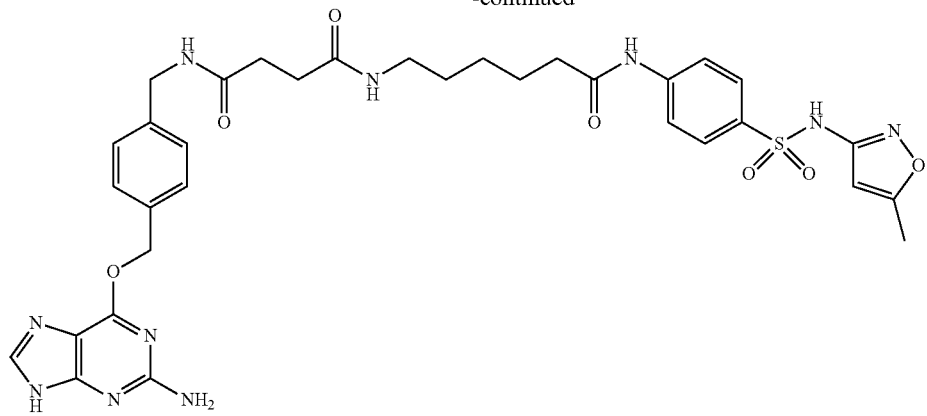

iii-2

Reactions and conditions: (a) EDC HCl, HOBt, DIPEA, DMF, rt., overnight; (b) 100% TFA, rt., 30 min; (c) succinic anhydride, DIPEA, DMSO, rt., 1 h; (d) TSTU, DIPEA, DMSO rt., 5 min; ii-2, rt., 30 min.

6-amino-N-{4-[(5-methyl-1,2-oxazol-3-yl)sulfamoyl]phenyl}hexanamide (ii-2)

To a solution of Boc-6-aminohexanoic acid (150 mg, 0.65 mmol, 1 eq.) in DMF (2.0 mL), EDC HCl (140 mg, 0.72 mmol, 1.1 eq.) and HOBt (98 mg, 0.72 mmol 1.1 eq.) were added under stirring. After full dissolution of the reagents, sulfamethoxazole (494 mg, 1.9 mmol, 3 eq.) was added followed by DIPEA (0.11 mL, 0.65 mmol, 1 eq.). The reaction was stirred overnight at RT. Finally, the reaction was acidified with acetic acid (0.2 mL), purified by HPLC and lyophilized to yield a white solid (182.1 mg, 0.39 mmol, 59%).

The Boc-protected product (60 mg, 0.128 mmol, 1 eq.) was dissolved in TFA (0.5 mL) and stirred for 30 min. TFA was then evaporated under reduced pressure. The product was dissolved in 0.5 mL DMSO, purified by HPLC and lyophilized to yield a white solid (30.1 mg, 81.9 μmol, 64%).

$BG-NH_2$ (i-4) was synthesized accordingly to the previously described procedure (Keppler et al Nat Biotechnol. 2003 Jan.; 21(1):86-9.).

4-[(4-{[(2-amino-9H-purin-6-yl)oxy]methyl}benzyl)amino]-4-oxobutanoic acid (iii-1)

To a suspension of BG-NH2 (300 mg, 1.1 mmol, 1 eq.) in dry DMSO (6 mL) were added DIPEA (0.4 mL, 2.4 mmol, 2.2 eq.) and succinic anhydride (133 mg, 1.3, 1.2 eq.) under stirring. The reaction mixture clarified during the process of the reaction. After 1 h, the reaction was shown to be complete. 1 mL H₂O was added to the reaction mixture to hydrolyze the succinic anhydride. Finally, the reaction was quenched with 0.5 mL acetic acid, purified by HPLC and lyophilized to yield a white solid (388 mg, 1.05 mmol, 95%). BG-Suc-C6-SMX (iii-2)

To a solution of compound iii-1 (19.5 mg, 52.7 μmol, 1 eq.) in dry DMSO (0.6 mL), DIPEA (17.5 μL, 105.4 μmol, 2 eq.) and TSTU (23.8 mg, 79 μmol, 1.5 eq.) in 200 μL DMSO were added. After 5 min, the formation of the NHS-ester was checked by TLC (9/1 DCM/MeOH) and LC-MS. Then, the amine ii-2 (300 μl, 63.2 μmol, 1.2 eq.) with DIPEA (17.5 μL, 105.4 μmol, 2 eq.) was added and stirred for 30 min. Finally, the reaction was quenched first with 200 μL H₂O (15 min) and then with 50 μL AcOH. The product was purified by HPLC and lyophilized to yield a white solid (7.1 mg, 9.9 μmol, 19%).

The fusion protein comprising of the human SPR, Tag-GFP2, a 30-proline linker, SNAP-tag and TagRFP was constructed by replacing the coding sequence of Halo-tag in a previous construct SPR-Halo-p30-SNAP by the coding sequence of TagGFP2 (Evrogen, Moscow, Russia) and inserting TagRFP (Evrogen, Moscow, Russia) at the end of the construct using Gibson Assembly (NEB, Ipswich, England) yielding SPR-TagGFP2-p30-SNAP-TagRFP. The fusion protein was expressed in the *E. coli* strain Rosetta-Gami™ 2 (DE3)pLysS (Novagen, Merck KGaA, Darmstadt, Germany) and purified using a C-terminal His-tag as well as an N-terminal Strep-tag II to obtain the full construct.

The purified fusion protein SPR-TagGFP2-p30-SNAP-TagRFP (5 μM) was labelled with 2 eq. of BG-Suc-C6-SMX (10 μM) in a buffer (50 mM HEPES, 150 mM NaCl, pH 7.5) for 1 h at room temperature. After the incubation, the excess of ligand was removed by three washing steps (3×400 μL) with the aforementioned buffer using centrifugal filter spin column with a 50 kDa cut-off membrane (Amicon Ultra-0.5 Centrifugal Filter, Merck KGaA, Darmstadt, Germany). The purified sensor is then diluted to a concentration of 5 μM in HEPES buffer (in 50 mM HEPES, 150 mM NaCl, pH 7.5).

To evaluate the performance of the sensor, titrations experiments were performed with different concentrations of NADP⁺. The labelled sensor was diluted to a concentration of 50 nM in 100 μL of HEPES buffer (50 mM HEPES, 150 mM NaCl, 0.5 mg/mL BSA, pH 7.5) containing defined concentrations of NADP⁺ in black non-binding 96-well plates (Greiner Bio-One, Kremsmünster, Austria). The solutions were incubated at room temperature for at least 15 minutes to ensure that the sensor had reached equilibrium. Fluorescence measurements were done on an Infinite M1000 spectrofluorometer (TECAN). Excitation was carried out at 450 nm with a bandwidth of 10 nm and spectra were recorded from 480 to 630 nm using a step size of 1 nm and bandwidths of 10 nm.

Figure 7C:
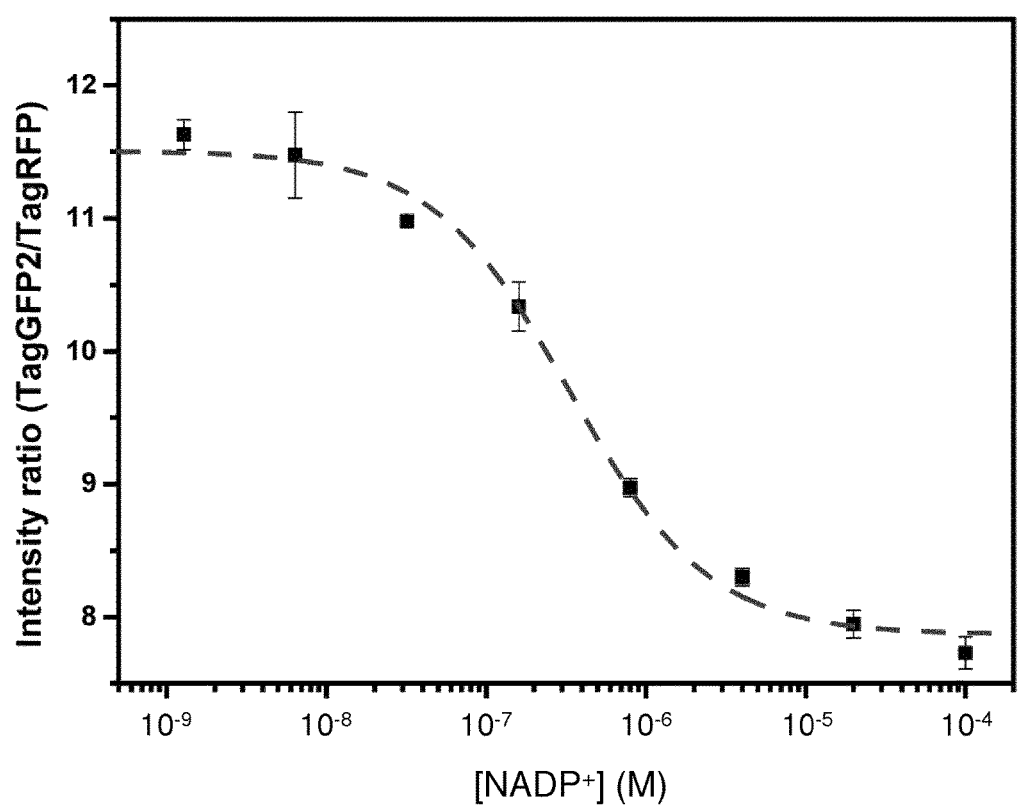

As shown in FIG. 7C, the sensor is able to monitor changes in the NADP+ concentration with an overall FRET ratio change of 1.5 between a closed conformation (low NADP⁺ concentration) and an open conformation (high NADP⁺ concentration). In addition, the measured apparent Kd of the sensor is 337±59 nM in presence of NADP⁺. Although the overall change is significantly lower compared to the previously described sensors, using a more efficient FRET pairs in term of spectral overlap (between the emission of the donor and excitation of the acceptor) and brightness will certainly improve the sensitivity of sensors based on two fluorescent proteins.

One advantage of the sensors for NADP and NAD based on two fluorescent proteins is the use of a synthetic labelling molecule (containing the SPR ligand) with improved cell permeability since it does not contain a synthetic fluorophore. Furthermore, the synthetic scheme is significantly shorten and simplified. The same molecule functionalized with $O^4$-benzyl-2-chloro-6-aminopyrimidine (CP) can also be used for the labelling of SNAP-tag and might further improve the cell permeability.

Example 8:
SNAP_P30_hSPR(D41W42)_NLuc_cpDHFR

Figure 8A:
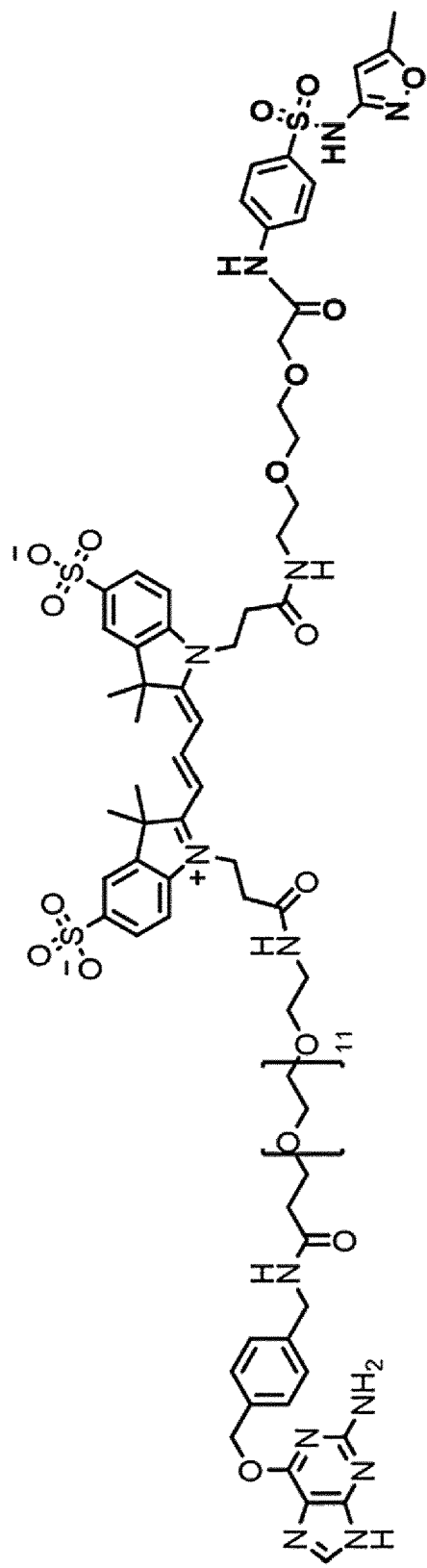

This example describes the design and construction of an optimized BRET-based sensor capable of sensing the concentration of $NAD^+$. The sensor comprises a mutant of SPR as NAD(H)-specific binding protein and BG-Peg11-Cy3-sulfamethoxazole as SPR-L. NanoLuc is used as the luciferase which forms a BRET pair with Cy3. SNAP-tag is labelled with the synthetic molecule BG-Peg11-Cy3-sulfamethoxazole (FIG. 8A).

The fusion protein SNAP_P30_hSPR(D41W42)_NLuc_cpDHFR comprising of a mutant of SPR(D41W42), Nano-Luc (NLuc), a 30-proline linker, SNAP-tag and circular-permutated dihydrofolate reductase (cpDHFR) was constructed using standard procedures as described above. cpDHFR is derived from wild-type *E. coli* DHFR by fusing the original N and C termini with a (glycine)$_5$ linker and splitting between Asn23 and Leu24. It was found that the attachment of an extra protein domain to the C terminus of NanoLuc decreased unspecific interactions of NanoLuc with other molecules. The fusion protein was expressed in the *E. coli* strain Rosetta-Gami™ 2 (DE3)pLysS (Novagen, Merck KGaA, Darmstadt, Germany) and purified using a C-terminal His-tag as well as an N-terminal Strep-tag II to obtain the full construct.

Figure 8B:
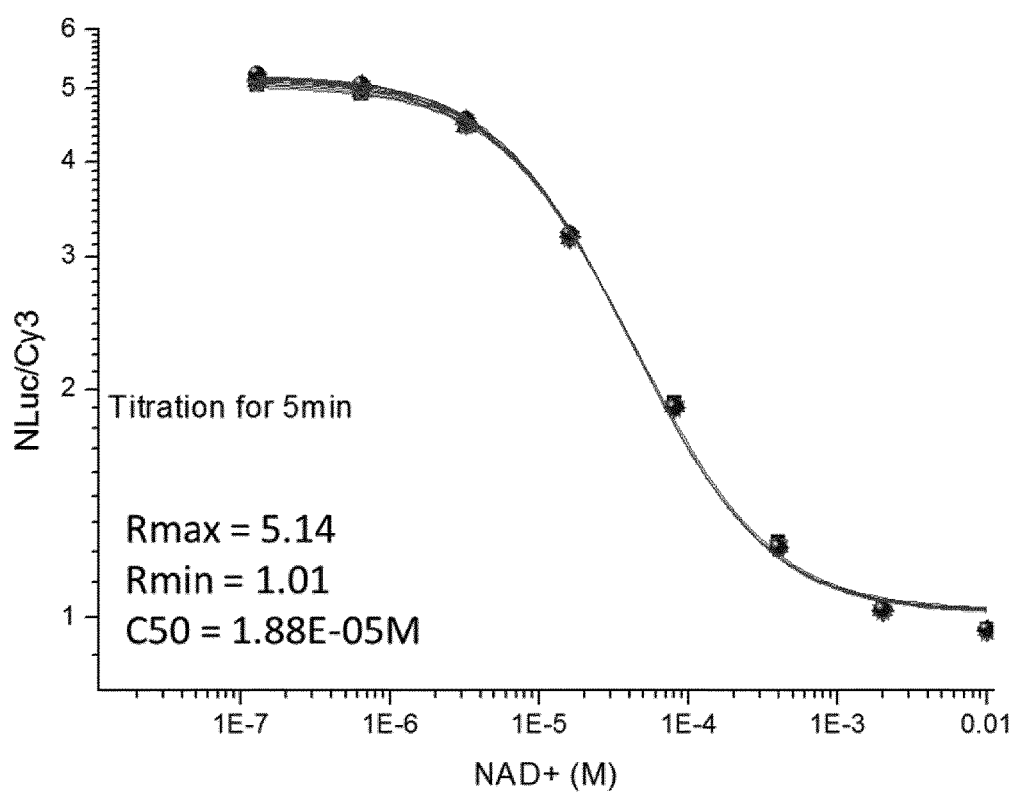

The purified fusion protein SPR(D41W42)-Halo-p30-SNAP (5 μM) was labelled with 2 eq. of BG-Peg11-Cy3-sulfamethoxazole (10 μM) in a buffer (50 mM HEPES, 150 mM NaCl, pH 7.5) for 1 h at room temperature. After the incubation, the excess of ligand was removed by three washing steps (3×400 μL) with the aforementioned buffer using centrifugal filter spin column with a 50 kDa cut-off membrane (Amicon Ultra-0.5 Centrifugal Filter, Merck KGaA, Darmstadt, Germany). The following conditions were used for titration of the sensor with $NAD^+$: 2.5 nM sensor was added to a buffer (500 mM HEPES, 500 mM NaCl, 10 mg/mL BSA, pH 7.5) containing NAD+ at various concentrations and 1000-fold diluted NanoLuc substrate. The assay was analyzed by recording the light emitted at 486 nm (from NanoLuc) and at 595 nm (from Cy3) and calculating the ratio of the two intensities. Measurements were done on an EnVision Multilabel Reader (Perkin Elmer). The apparent Kd of the sensor for NAD+ is 19 μM. The observed ratio change when going from the open to the closed form of the sensor is fivefold (FIG. 8B).

Figure 8C:
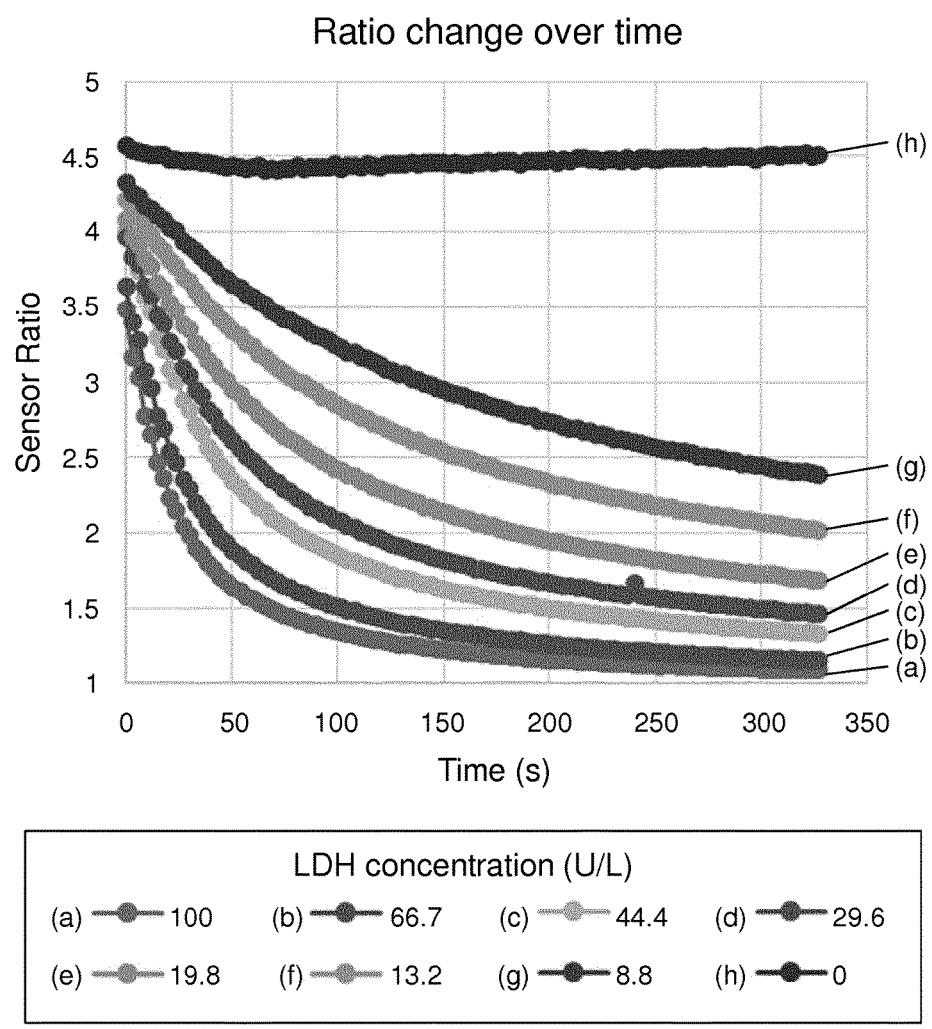
Figure 8D:
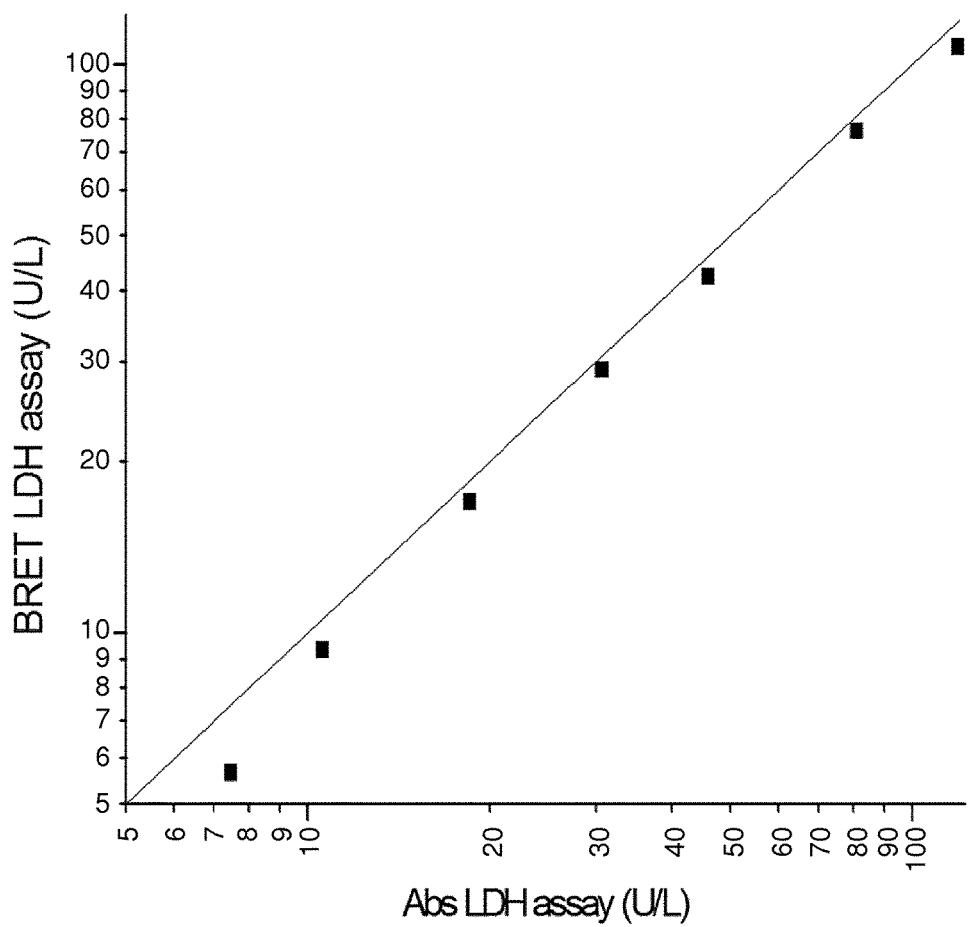

The sensor can also be used to measure the activity of lactate dehydrogenase (LDH) (FIGS. 8C and D). LDH catalyzes the conversion of lactate to pyruvic acid and back, as it converts NADH to NAD+ and back. 5 nM sensor was prepared in 50 uL buffer (500 mM HEPES, 500 mM NaCl, 10 mg/mL BSA, pH 7.5) containing 2 mM pyruvate and 1 mM NADH. Another 50 μL buffer (500 mM HEPES, 500 mM NaCl, 10 mg/mL BSA, pH 7.5) containing 500-fold diluted NanoLuc substrate and LDH at various levels was added before starting the measurement. The emitted light was measured over 5 min (FIG. 8C). The $NAD^+$ production rate was obtained by calculating the concentration of NAD+ at each time point based on the ratio and the titration curve as shown in FIG. 8B. To calculate the units of LDH in the sample, the following definition was used: 1 U/L LDH corresponds to 1.67E-8 M/s in NAD+ production rate. The LDH level measured using the sensor was plot against the result obtained by a standard absorbance assay for the same sample (FIG. 8D). The assays described above can also be done on filter paper as described in Griss et. al. Nature Chemical Biology, 2014. 10(7): p. 598-603.

The invention claimed is:

1. A sensor molecule for fluorescence or luminescence-based detection of a nicotinamide adenine dinucleotide analyte, in particular for detecting the concentration of NADP$^+$ or the ratio of the concentrations of NADP$^+$ and NADPH, NADP$^+$/NADPH, the sensor comprising
   (i) a binding protein (BP) for the nicotinamide adenine dinucleotide analyte, the BP being sepiapterin reductase (SPR), wherein the SPR is human sepiapterin reductase (hSPR) according to SEQ ID NO:4, rat sepiapterin reductase according to SEQ ID NO:3, mouse sepiapterin reductase according to SEQ ID NO:2, or a variant thereof having at least 95% sequence identity with SEQ ID NO:4, SEQ ID NO: 3 or SEQ ID NO:2, provided that the variant comprises the residues corresponding to Ser157, Tyr170, Lys174, and Asp257 in hSPR;
   (ii) an SPR ligand (SPR-L) capable of intramolecular binding to said BP in the presence of the oxidized form of said analyte, wherein said SPR-L is based on a benzenesulfonamide; and
   (iii) at least one fluorophore.

2. Sensor molecule according to claim 1, for resonance energy transfer (RET) based analyte detection, the sensor comprising a segment A connected via a linker to a segment B, wherein each of segment A and segment B comprises a member of a RET pair comprising a donor moiety and an acceptor moiety, further characterized in that
   (i) segment A comprises the BP
   (ii) segment B comprises the SPR-L such that the donor moiety and the acceptor moiety are in a suitable juxtaposition to yield a RET signal when SPR-L is bound to BP, and wherein an analyte-induced change in SPR-L binding to BP results in a change in RET efficiency.

3. Sensor molecule according to claim 1, wherein said BP is human sepiapterin reductase (hSPR) having the amino acid sequence of SEQ ID NO:4 or a variant thereof having at least 98% sequence identity with SEQ ID NO:4, provided that the variant comprises the residues corresponding to Ser157, Tyr170, Lys174, and Asp257 in hSPR.

4. Sensor molecule according to claim 1, wherein said BP comprises an amino acid sequence showing at least 99%, sequence identity with SEQ ID NO: 4, SEQ ID NO: 2 or SEQ ID NO:3.

5. Sensor molecule according to claim 1, wherein BP comprises an SPR wherein the residues corresponding to positions 17 and 42 of SEQ ID NO:4 are basic residues.

6. Sensor molecule according to claim 1, wherein said SPR-L is a benzenesulfonamide having a pKa below 6 or above 9.

7. Sensor molecule according to claim 2, wherein the RET pair is a FRET pair.

8. Sensor molecule according to claim 2, wherein the RET pair is a BRET pair, and wherein the BRET pair comprises a luciferase and a fluorescent acceptor.

9. Sensor molecule according to claim 8, wherein the luciferase is NLuc luciferase that is provided at its C-terminus with a circular-permutated dihydrofolate reductase (cpDHFR).

10. Sensor molecule according to claim 2, wherein the linker is a proteinaceous linker.

11. Sensor molecule according to claim 1, wherein the sensor molecule is immobilized or absorbed to a solid carrier.

12. A method for fluorescence or luminescence-based in vitro detection of the concentration of a nicotinamide adenine dinucleotide analyte in a sample, the method comprising
   (a) contacting the sample with a sensor molecule according to claim 1 under conditions allowing for an analyte-dependent binding of said SPR-L to SPR or SPR mutant modulates the spectroscopic properties of the fluorophore or emission spectra of the sensor molecule; and
   (b) analyzing a change in a signal generated by modulation of the spectroscopic properties of the fluorophore or emission spectra of the sensor molecule and relating the signal change to the concentration of a nicotinamide adenine dinucleotide analyte in the sample.

13. Method according to claim 12, wherein the concentration of NADP$^+$ or the NADP$^+$/NADPH ratio in the sample is detected.

14. Method according to claim 12, wherein the sample is a biological sample or a fraction thereof.

15. Method according to claim 12, wherein the sample comprises
   (i) an unknown concentration of $NADP^+$ or NADPH
   (ii) an unknown ratio of the concentrations of $NADP^+$ and NADPH, or
   (iii) an unknown concentration of an enzyme that generates or consumes $NADP^+$.

16. Kit of parts comprising a sensor molecule according to claim 1 and a solid carrier.

17. Kit according to claim 16, comprising a BRET-based sensor, further comprising a luciferase substrate.

18. The sensor molecule according to claim 1, wherein said SPRL based on a benzenesulfonamide is selected from the group consisting of sulfasalazine, sulfathiazole, sulfamethoxazole, sulfamethizole, phthalylsulfathiazole, sulfapyridine, sulfadiazine, sulfamerazine, sulfachloropyridazine, sulfameter, chlorpropamide, glibenclamide and tolbutamide.

19. The sensor molecule according to claim 7, wherein the FRET pair is selected from
   (i) a fluorescent protein and a self-labelling tag tethered with a synthetic molecule containing a fluorophore;
   (ii) two orthogonal self-labelling tags, one for the attachment of the synthetic molecule containing a donor moiety, the other to attach an acceptor moiety fluorophore; and
   (iii) two fluorescent proteins.

20. The sensor molecule according to claim 11, wherein the sensor is immobilized or absorbed to glass, a transparent plastic, a gold surface, paper or a gel.

21. Method according to claim 12, wherein
   (i) ex vivo clinical or diagnostic testing is performed;
   (ii) an ex vivo enzymatic assay that involves the formation or consumption of $NADP^+$ is performed;
   (iii) ex vivo high-throughput screening is performed for compounds that can modulate NADP(H) in cells or for the validation of the toxicity profile of therapeutic drugs; or
   (iv) live cell measurements are performed comprising the use of a widefield fluorescence microscope, confocal fluorescence microscope or a Fluorescence Lifetime Imaging Microscopy (FLIM) system with appropriate excitation and emission filters.

22. A sensor molecule for fluorescence or luminescence-based detection of a concentration of $NAD^+$ or an $NAD^+$/NADH ratio, the sensor comprising
   (i) a binding protein (BP) capable of binding $NAD^+$, the BP being a variant of sepiapterin reductase (SPR) having at least 95% sequence identity with SEQ ID NO:4, SEQ ID NO: 3 or SEQ ID NO:2, provided that the variant comprises residues corresponding to Ser157, Tyr170, Lys174, and Asp257 of SEQ ID NO:4, and provided that a residue corresponding to position 41 of SEQ ID NO: 4 is Asp or a residue corresponding to position 42 of SEQ ID NO:4 is Val, Ile, or Trp;
   (ii) an SPR ligand (SPR-L) capable of intramolecular binding to said BP in the presence $NAD^+$, wherein said SPR-L is based on a benzenesulfonamide; and
   (iii) at least one fluorophore.

* * * * *